US005616135A

United States Patent [19]

Thorne et al.

[11] Patent Number: 5,616,135
[45] Date of Patent: Apr. 1, 1997

[54] SELF RETRACTING MEDICAL NEEDLE APPARATUS AND METHODS

[75] Inventors: Gale H. Thorne, Bountiful; David L. Thorne, Kaysville; Charles V. Owen, Highland, all of Utah

[73] Assignee: Specialized Health Products, Inc., Bountiful, Utah

[21] Appl. No.: 565,881

[22] Filed: Dec. 1, 1995

Related U.S. Application Data

[63] Continuation-in-part of Ser. No. 455,514, May 31, 1995, Pat. No. 5,549,708, which is a continuation of Ser. No. 370,728, Jan. 10, 1995, Pat. No. 5,480,385, Ser. No. 436, 976, May 8, 1995, Pat. No. 5,487,734, and Ser. No. 484,533, Jun. 7, 1995, Pat. No. 5,542,927, each is a continuation-in-part of Ser. No.370,728, Jan. 10, 1995, Pat. No. 5,480,385.

[51] Int. Cl.⁶ .................................................. A61M 5/00
[52] U.S. Cl. ......................... 604/192; 604/263; 128/763
[58] Field of Search ................................... 604/192, 187, 604/198, 263, 195; 128/763–765, 919

[56] References Cited

U.S. PATENT DOCUMENTS

| | | | |
|---|---|---|---|
| 3,587,575 | 6/1971 | Lichenstein | 128/128 |
| 4,676,783 | 6/1987 | Jagger | 604/171 |
| 4,813,936 | 3/1989 | Schroeder | 604/195 |
| 4,850,374 | 7/1989 | Diaz-Ramos | 128/763 |
| 4,892,525 | 1/1990 | Hermann, Jr. | 604/263 |
| 4,909,794 | 3/1990 | Haber | 604/195 |
| 4,936,830 | 6/1990 | Verlier | 604/110 |
| 4,946,446 | 8/1990 | Vadher | 604/198 |
| 4,955,870 | 9/1990 | Ridderheim | 604/195 |
| 4,966,593 | 10/1990 | Lennox | 604/198 |
| 4,978,340 | 12/1990 | Terrill | 604/195 |
| 4,985,021 | 1/1991 | Straw | 604/198 |
| 4,986,816 | 1/1991 | Steiner | 604/192 |
| 4,988,339 | 1/1991 | Vadher | 604/197 |
| 4,994,034 | 2/1991 | Botich | 604/110 |
| 4,995,870 | 2/1991 | Baskas | 604/110 |
| 5,092,853 | 3/1992 | Couvertier | 604/195 |
| 5,098,402 | 3/1992 | Davis | 604/195 |
| 5,114,404 | 5/1992 | Paxton | 604/110 |
| 5,147,303 | 9/1992 | Martin | 604/110 |
| 5,180,370 | 1/1993 | Gillespie | 604/110 |
| 5,188,599 | 2/1993 | Botich | 604/110 |
| 5,193,552 | 3/1993 | Columbus et al. | 128/760 |
| 5,195,983 | 3/1993 | Boese | 604/192 |
| 5,195,985 | 3/1993 | Hall | 604/195 |
| 5,205,823 | 4/1993 | Zdeb | 604/110 |
| 5,205,824 | 4/1993 | Mazur | 604/110 |
| 5,209,739 | 5/1993 | Talslay | 604/195 |
| 5,215,533 | 6/1993 | Robb | 604/195 |
| 5,246,428 | 9/1993 | Falknor | 604/198 |
| 5,254,099 | 10/1993 | Kuracina | 604/198 |
| 5,256,153 | 10/1993 | Hake | 604/198 |
| 5,267,976 | 12/1993 | Guerineau | 604/198 |
| 5,320,606 | 6/1994 | Jore | 604/110 |
| 5,356,392 | 10/1994 | Firth et al. | 128/763 X |
| 5,374,250 | 12/1994 | Dixon | 604/110 |

OTHER PUBLICATIONS

Patricia Seremet, "Small Tolland Company Takes Jab at Safety Needle Market," *The Hartford Courant*, Sep. 13, 1995, pp.: F1 and F3.

*Primary Examiner*—John D. Yasko
*Attorney, Agent, or Firm*—Gale H. Thorne

[57] ABSTRACT

Method and apparatus associated with safe retraction of medical needles after use. Embodiments are disclosed for self-retracting needle systems for both blood draw, syringe and catheter insertion systems. Invention manufacture requires only a minimal number and complexity of parts such that a projected manufacturing cost is potentially low enough to permit the apparatus to be cost competitive with contemporary non-self retracting needle systems. Methods for making and assembling each of the disclosed the embodiments is also disclosed. One blood draw embodiment can be made with as few as three molded parts. Energy-storing, needle-retracting mechanisms comprise elastic tubing and vacuum generating piston parts. In an elastic tubing embodiment, selective, constrictive control of stretched tubing volumes effectively inhibits regurgitant flow from the needle. In all embodiments, needle retraction is a single handed operation permitting a technicians other hand to be used in wound care. Use of frangible parts permits the apparatus housing to be attached to a needle cover, which, in combination, are used as a transport container to further reduce apparatus costs.

62 Claims, 36 Drawing Sheets

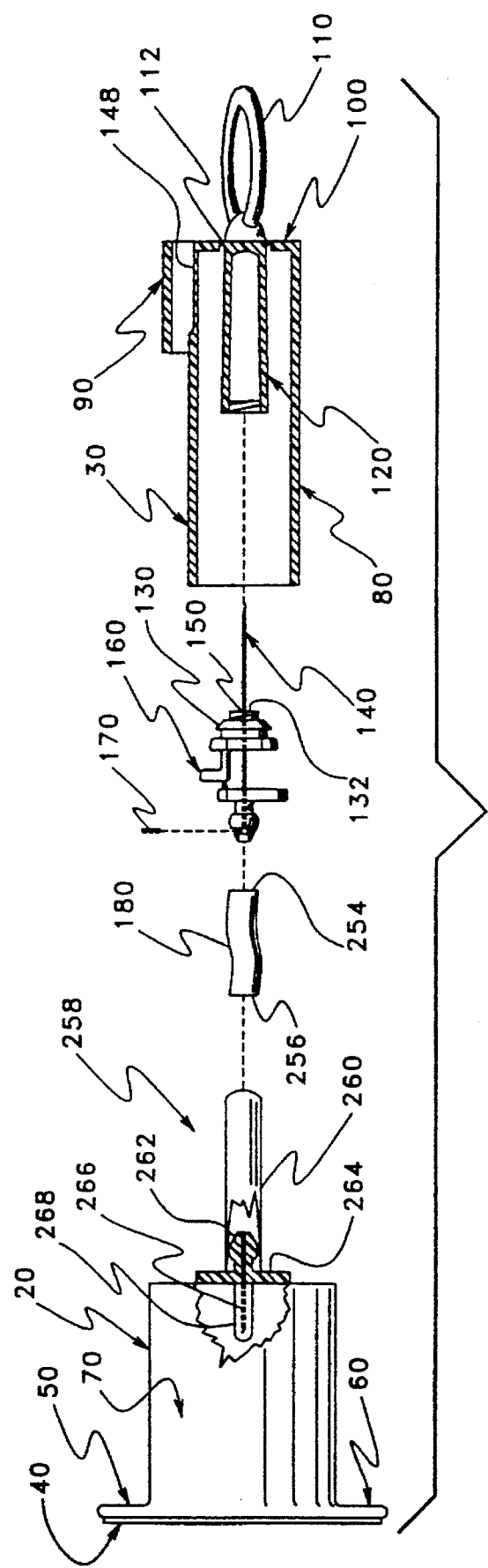

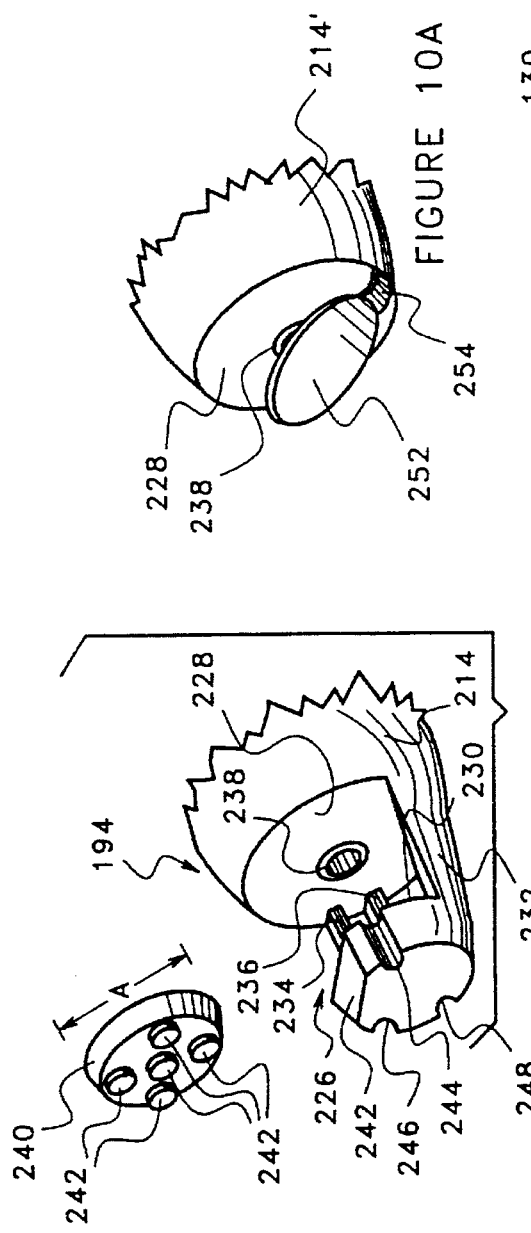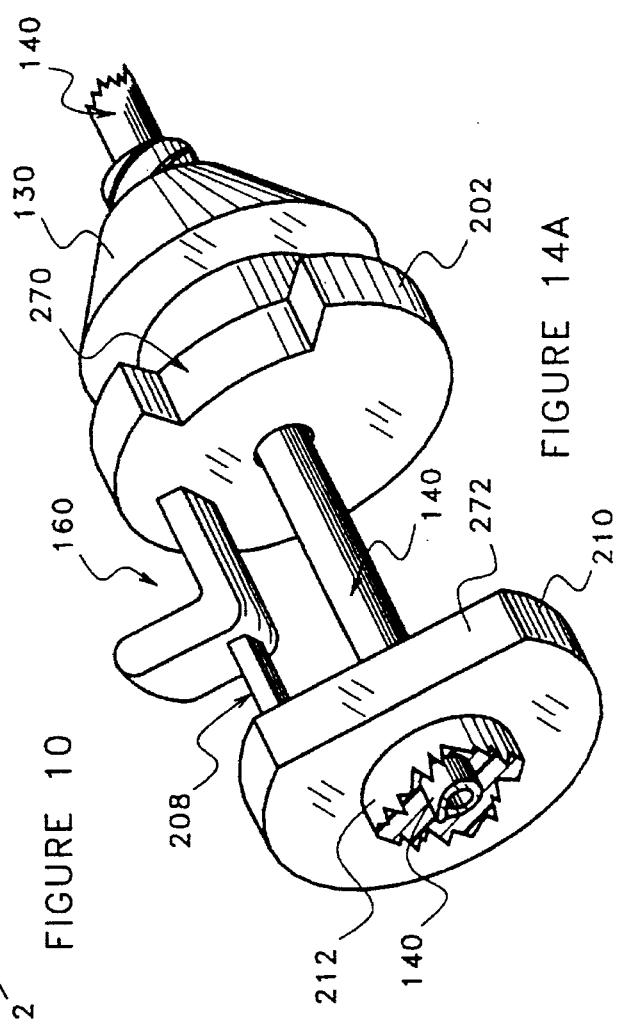

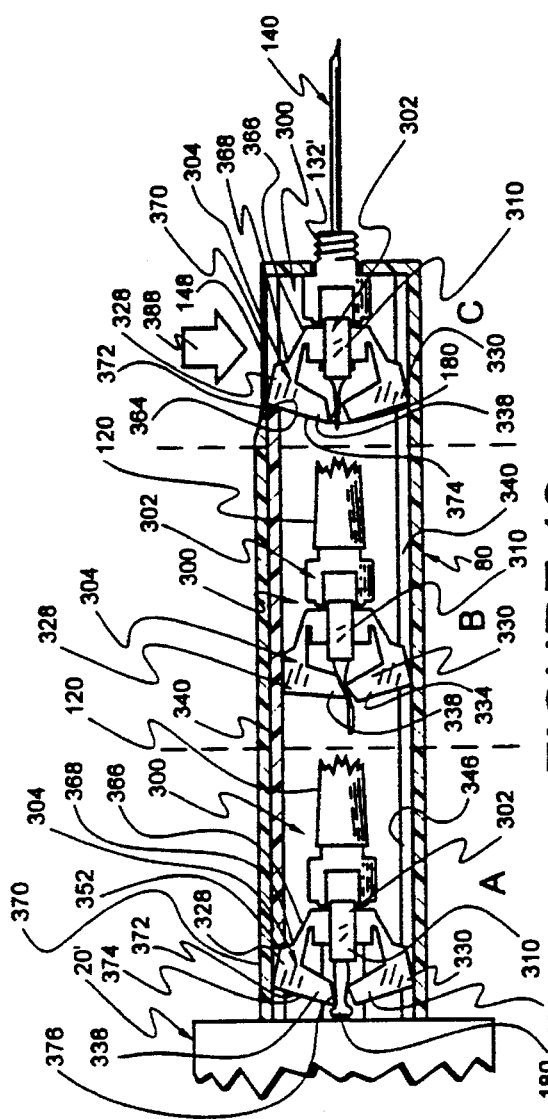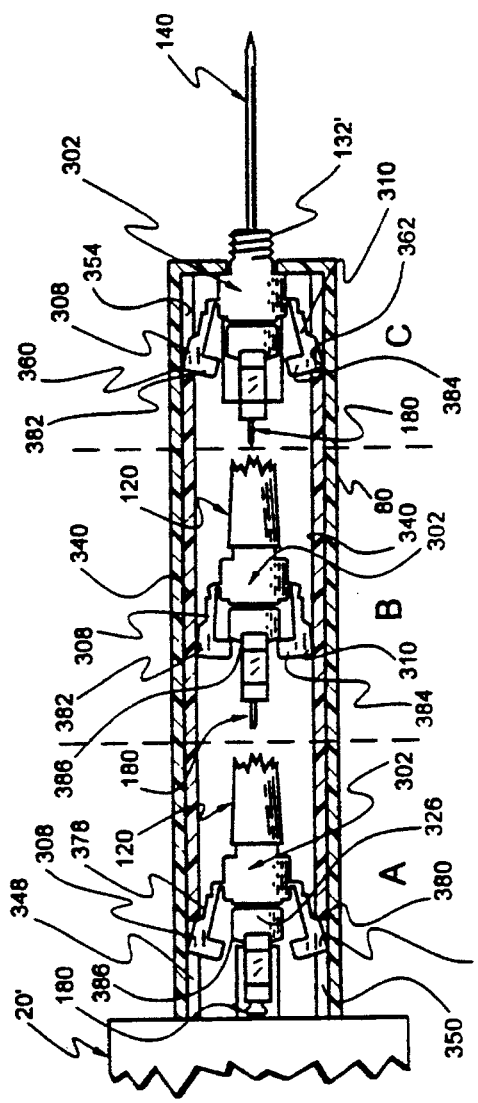

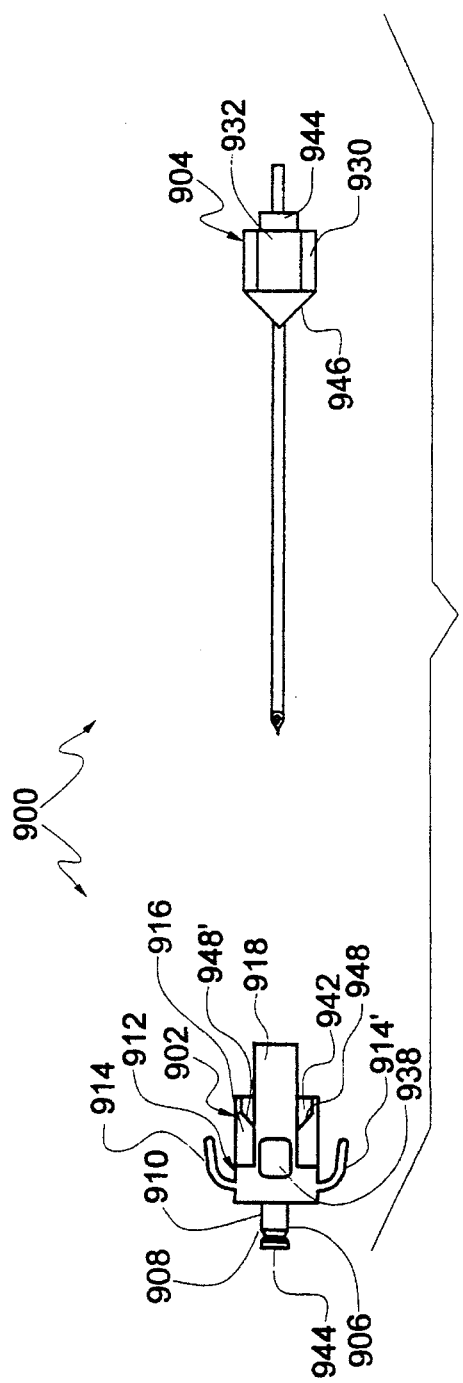
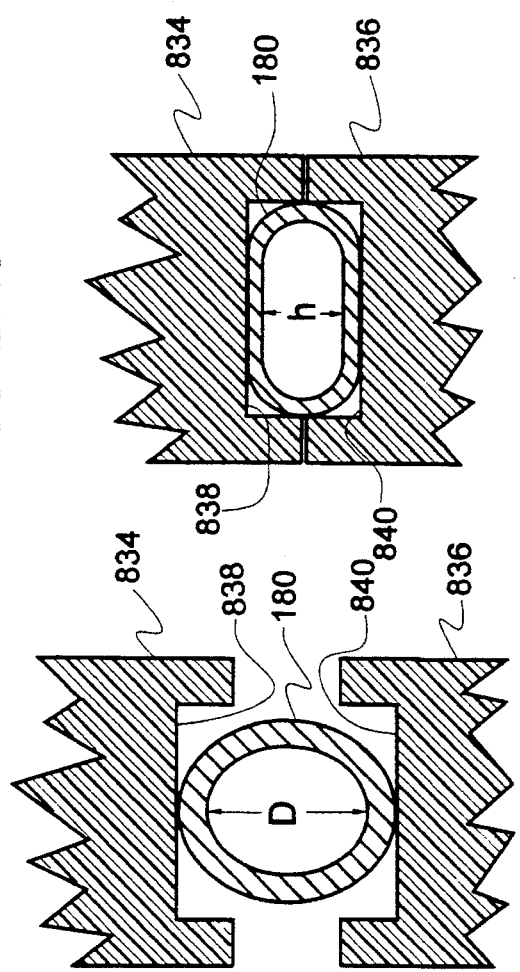
FIGURE 48
FIGURE 41
FIGURE 42

SELF RETRACTING MEDICAL NEEDLE APPARATUS AND METHODS

CONTINUATION

This application for patent is a continuation-in-part of U.S. patent application Ser. No. 08/455,514 filed May 31, 1995, now U.S. Pat. No. 5,549,708 which is a continuation of U.S. patent application Ser. No. 08/370,728 filed Jan. 10, 1995, now U.S. Pat. No. 5,480,385 and U.S. patent application Ser. No. 08/436,976 May 8, 1995, now U.S. Pat. No. 5,487,734 and U.S. patent application Ser. No. 08/484,533 filed Jun. 7, 1995, now U.S. Pat. No. 5,542,927 and are continuations-in-part of U.S. patent application Ser. No. 08/370,728 filed Jan. 10, 1995 now U.S. Pat. No. 5,480,385.

FIELD OF THE INVENTION

This invention relates generally to medical needle apparatus and methods and particularly to apparatus comprising medical needles which are self-retracting from an extended position at which the needle is used to a retracted position where the needle is fully withdrawn and encased within a housing for safe disposal. Further, the invention is related to medical products which may only be used once to eliminate cross contamination from one patient to another and to those medical products which have sterile parts inherently protected from contamination without need of additional packaging apparatus.

PRIOR ART

Problems associated with inadvertent needle sticks are well known in the art of blood withdrawal, transdermal medication injection, catheter emplacement and other medical procedures involving uses of medical needles. Ever increasing attention is being paid to needle stick problems due to the contemporary likelihood of being exposed to AIDS and Hepatitis.

Commonly, procedures involving needle withdrawal require a technician to use one hand to place pressure at the wound site where a needle is being withdrawn while removing the needle apparatus with the other hand. It is common practice for a tending technician to give higher priority to care for the wound than is given to disposal of a needle. Such priority either requires an available sharps container within ready reach or another means for safe disposal without leaving the patient's side. Providing adequate care is often compounded by patient condition and mental state (e.g. in burn units and psychiatric wards). Under such conditions, it is often difficult, if not impossible, to take appropriate procedures to properly dispose of a used, exposed needle while caring for a patient.

Widespread knowledge and history associated with needle care and disposal problems have resulted in conception and disclosure of a large number of devices each of which represents an attempt to provide not only a solution to the problem of needle sticks, but a device which is commercially viable (i.e. cost and price competitive with currently used non-self retracting devices). Though some devices describe application in the area of blood withdrawal (see U.S. Pat. Nos. 4,850,374 (Nydia Diaz-ramos) and 5,195,985 (Hall)), most contemporary related arc is directed toward syringes and like devices. Broadly, related art may be classified into two categories, devices which operate manually and devices which comprise self-contained needle retraction.

Examples of manually operated medical needle devices are provided in U.S. Pat. Nos. 4,676,783 (Jagger et al.), 4,83,936 (Schroeder), 4,909,794 (Haber), 4,978,340 (Terrill et al.), 4,995,870 (Baskas), 5,098,402 (Davis), 5,180,370 (Gellespie), 5,188,599 (Botich et al.), 5,195,985 (Hall), 5,205,823 (Zdeb), 5,205,824 (Mazur), 5,215,533 (Robb), and 5,256,153 (Hake). Manual withdrawal is generally a two-handed procedure, making wound care a secondary step or requiring an added medical technician.

Examples of self-retracting devices are found in U.S. Pat. Nos. 4,946,446 (Vadher), 4,955,870 (Ridderheim et al.), 4,966,593 (Lennox), 4,988,339 (Vadher), 4,994,034 (Botich et al.), 5,114,404 (Paxton et al.), 5,147,303 (Martin), 5,092,853 (Couvertier), 5,246,428 (Falknor), 5,254,099 (Karacina), and 5,267,976 (Guerineau et al.). Guerineau et al. discloses self-retraction resulting from a vacuum force while others disclosed above generally disclose self-retraction resulting from release of a cocked or biased spring.

Generally, other than acceptance of the type of operation offered by such devices, commercial viability is dependent upon manufacturing cost. Purchase decisions in the area in which these devices are used are very cost sensitive. If gains in either improvement in safety or in labor savings are not found to make a device sufficiently competitive with contemporary competitive items, those devices are usually not found to be commercially viable. Motivation for providing a cost competitive self-retracting needle apparatus coupled with improved safety of use of the apparatus resulted in conception of the instant inventions disclosed herein.

BRIEF SUMMARY AND OBJECTS OF THE INVENTION

In brief summary, each novel invention disclosed herein dramatically diminishes known major problems resulting from injury-related needle sticks which occur when needle tips are bared as medical needles are withdrawn from a patient at the end of a needle insertion procedure. In preferred embodiments, operation of each invention involves elongating a medical needle apparatus and providing access a medical needle which is enclosed by a cover prior to use. The act of elongating the apparatus energizes a force storing memory element and cocks a releasable latch. Generally the needle is made available for a medical procedure by physically separating the needle cover from the rest of the apparatus immediately prior to use. Once the cover is removed, the needle is used in a medical procedure (e.g. for acquiring a blood sample or for catheter insertion).

In a preferred embodiment, when the medical procedure is complete, a simple distortion of a portion of the housing, preferably by squeezing the housing by the thumb and forefinger of one hand, retracts the needle safely into the housing. It is important to note that the needle can be removed directly from a patient and safely encased in the housing by a simple action of a single hand of an attending technician, leaving the technician's other hand free for other concurrent medical procedures, such as care of the wound site from which the needle is retracted. After retraction, the needle is fully enclosed and contained, permitting the needle apparatus to be laid aside without fear of an inadvertent needle stick while full attentive care is provided to the patient.

Generally, this novel invention is for a self-retracting medical needle apparatus which is employed in transporting, using and retracting a medical needle into safe containment within a housing after use. The apparatus comprises the housing into which the medical needle is retracted at the end of a medical procedure.

In a preferred method, the apparatus is triggered by a technician causing the needle to be retracted by the apparatus directly from a patient and, in a continuing motion, to be deposited into the housing. In addition to the housing, the apparatus comprises a needle cover, a medical needle assembly, a needle support catch and a linear motion energy storage member.

The housing is characterized by an elongated, generally cylindrical shape having an opening at one end wherethrough the medical needle passes. To prepare the apparatus for use, the apparatus is elongated to an extended state by moving the one end apart from an opposing end of the housing. In this manner, the medical needle which is most closely associated with the one end is also moved apart from the opposing end. To assure that the medical needle is affixed in a stable condition relative to the housing, the housing comprises a catch for a latch which secures the apparatus in the extended state.

When the apparatus is in the extended state, a medical needle assembly associated with the medical needle is cocked, ready to be triggered to thereby retract the medical needle into the housing. A predetermined portion of the housing is dedicated to communicating a releasing action upon a trigger which disengages the needle assembly, thereby causing the medical needle to be retracted into the housing. The dedicated housing portion is preferably a deformable section of the housing which when deformed communicates with the trigger, but at other times provides a physical barrier to protect the medical needle from contamination and harm from sources external to the apparatus. In a preferred embodiment, an easily removed shield is used to cover the dedicated, communicating portion of the housing to prevent inadvertent triggering and subsequent premature retraction of the needle from the patient.

Before use, at least a portion of the needle cover generally extends outwardly from the one end of the housing. The needle cover and housing, in combination, commonly provide a measure of protection for maintaining sharpness and sterility of the medical needle. Further, in a preferred embodiment, the cover provides a handle which is used in elongating the apparatus.

In addition to the medical needle, the medical needle assembly comprises a secure attachment to the medical needle, a releasable latch which is affixed to a needle support catch when the apparatus is elongated for use, the trigger and a connecting hub which is integral with the needle attachment and which is used to affix the needle and attachment to a linear motion energy storage member. The medical needle assembly is substantially disposed within the housing and cover for transport and storage prior to use. When properly used, the medical needle is bared for use in a medical procedure subsequent to elongating the apparatus.

In a preferred embodiment, the needle support catch is an integral part of the housing. The needle support catch is disposed to engage the latch and thereby securely affix the needle when the apparatus is elongated.

The linear motion energy storage member may be a spring, a piston which draws a vacuum in a chamber as the apparatus is extended or any component which stores retracting energy as the apparatus is elongated. However, the preferred storage member is an elastic tube which not only stores potential energy for needle retraction as the apparatus is elongated, but also provides a pathway for fluid which is passed through the needle during the medical procedure.

Preferred materials for the elastic tube are silicone rubber and medical grade latex, although other tubing materials may be used within the scope of the invention. It should be noted that the elastic tubing is preferably in a rest or unstretched state while the apparatus is being transported or stored prior to use. The elastic tube is only stretched (stressed) when the apparatus is elongated for use.

As the needle may be directly retracted from a patient, it is preferred that fluid flow from the needle be kept to an absolute minimum during retraction. Due, at least in part, to tubing expansion about a hub when the elastic tube is stretched, most often an extended tube defines an internal volume which is larger than the internal volume same tube when unstretched. Generally that internal volume difference is a function of the difference in diameter of the internal diameter of the unstretched tube and the external diameter of hubs which connect and secure each end of the elastic tube to the apparatus. For this reason, it is preferred to utilize hubs which have substantially the same external diameter as the internal diameter of the tube when unstretched.

However, even when utilizing hubs having such restricted diameters, a small amount of regurgitant flow is still possible when the tube is released from a stretched state to constrict into a relaxed state. It has been found through experimentation that the volume of the tubing when stretched must be physically constricted to a volume which is less than that of the tubing when unstretched to assure that no regurgitant flow can occur under such conditions. Several mechanisms for so constricting the tubing have been successfully tested.

A first tube constricting mechanism comprises a mechanical lever associated with the latch. The mechanical lever is disposed to distort the tubing when the apparatus is elongated to differentially reduce the volume of the stretched tube to be smaller than the volume of the same tube when relaxed. The lever is preferably integrally attached to the releasable latch and moved along a ramp disposed within the housing to distort the tube more when the tubing is stretched than when the tubing is relaxed after retracting the needle.

A second tube constricting mechanism comprises a helical wrap disposed about the elastic tube. As the tube is stretched, the helical wrap partially chokes the tube to reduce the inner volume of the stretched tube to be less than that of the relaxed tube. Both of these mechanisms eradicate the causes of liquid regurgitation as the medical needle is retracted into the housing.

In a blood draw (phlebotomy) application, an evacuated blood collection tube receiving barrel assembly is affixed to the opposing end of the apparatus mentioned above. The barrel assembly comprises a needle for accessing a blood collection tube, the needle communicates with the elastic tube and is most often covered by a snubber. In this case, the medical needle is sized to be compatible with blood draw applications.

In a syringe application, a luer fitting is affixed to the opposing end of the apparatus mentioned above. The apparatus then becomes a syringe needle retraction system which may be used with any standard syringe having a complementary luer fitting. In this case, the apparatus and medical needle are sized and configured to be compatible with syringes used in medical applications.

In a catheter application, a filter which differentially passes gas, but which is impervious to liquid is affixed to the opposing end of the apparatus and to the elastic tube. The elastic tube then becomes a part which shows a "blood flash" used to show evidence of a catheter's entry into a blood vessel.

In general, use of the apparatus comprises the steps of elongating the apparatus thereby positioning a medical needle relative to parts moved away from the needle during apparatus elongation, affixing the needle thereat, storing energy in a linear energy storage member and cocking a trigger for later release; exposing the needle; performing a medical procedure on a patient and, while the needle is still resident in the patient, accessing a portion of the housing in communication with the trigger; actuating the trigger by action of a single hand, in a direction transverse to the long axis of the needle, to retract the needle directly from the patient into an enclosed housing for safe disposal within the apparatus. It is preferred that the accessing step described above comprise removal of a shield over a deformable portion of the housing, the deformable portion providing a communicating link between the single hand and the trigger.

It is also preferred that the storage of energy in the linear energy storage member involves stretching an elastic tube which also provides a useful pathway for fluid which is passed through the needle. Further, it is preferred that the elongating step comprises a partial constriction of the elastic tube whereby the internal volume of the stretched tube is less than the internal volume of the tube when relaxed and unstretched. This latter step is particularly useful in eliminating undesirable fluid regurgitation when the medical needle is retracted.

In a blood sampling embodiment, the invention comprises a housing/transport container which includes a barrel, a needle/hub assembly and a barrel/hub component. In some embodiments, apparatus of the instant invention require as few as three molded parts, each part being representative of the container, assembly and component mentioned above. However, contemporary molding methods and automated fabrication restrictions dictate implementation of four to five molded parts in presently preferred embodiments.

It is noted that, except for needles which are integrally connected to injection molded parts and an extruded tube, all parts are injection molded. In the case of the blood draw application an additional snubber tube is customarily used to cover a vacuum tube accessing needle in the barrel.

Accordingly, it is a primary object to provide a novel and improved medical needle retracting device comprising a housing and associated needle cover which, in combination, protect tip integrity and sterility of a medical needle and other internal parts of the device until use and which automatically fully retracts the needle into the housing after use.

It is a key object to provide the blood withdrawal device with an attached barrel for a blood acquisition vacuum tube (e.g. a Vacutainer® made by Beckton Dickenson).

It is another key object to provide a needle cover for the device which is releasably affixed to the housing during transport and storage of the device, but which is frangibly separable from the housing.

It is an important object to provide a means for releasing a cocked needle assembly by distorting a portion of the housing rather than requiring a button or other mechanical device to project through the housing wall.

It is also an important object to provide a protection for the portion which is distorted from being inadvertently deformed during insertion and use of the needle and to remove the protection with a single digit motion immediately prior to retracting the needle.

It is an object to provide parts disposed at each end of the device which facilitate manually extending the apparatus for use.

It is another primary object that the device be usable but once and the needle be safely enclosed when retracted.

It is a very important object that the device be made with as few injection molded parts as possible.

It is an object to provide an embodiment of the invention which comprises a latch which is releasable by franging a section of an assembly associated with the medical needle.

It is a significant object to provide a manufacturing method for assembly of the device which is compatible with automatic assembly equipment.

It is an object to provide a force storing memory element which stores energy as the apparatus is extended and which provides needle retracting force upon release of the needle assembly.

It is a meaningful object to provide a memory element which comprises an enclosed fluid flow pathway for withdrawn blood.

It is an object to nullify forces within the apparatus which cause regurgitant flow when the needle is retracted.

It is an object to provide a means for connecting the needle cover to the needle assembly during device manufacture which does not put undue stress upon a frangible part.

It is an object to provide a blood draw device associated with the apparatus.

It is yet another primary object to provide a novel and improved IV catheter insertion apparatus comprising a housing which maintains sterility of a medical needle, a catheter and other internal parts of the apparatus until use and which automatically fully retracts the needle into the housing after use.

It is still another object to provide a means for seeing a blood "flashback" within the IV catheter device as influent blood courses into the device from a pierced blood vessel.

It is an object to provide a syringe needle retraction device associated with the apparatus, the syringe needle retraction device being usefully employed with a medical syringe comprising a luer fitting.

These and other objects and features of the present invention will be apparent from the detailed description taken with reference to accompanying drawings.

BRIEF DESCRIPTION OF THE DRAWINGS

FIG. 6 is a an exploded side view of a blood draw device with some portions segmented and other portions removed for better presentation.

FIG. 10 is an exploded perspective of a section of the needle/hub assembly seen in FIGS. 7–9 and a valve leaflet which is used to restrict regurgitant flow from the device.

FIG. 10A is a perspective of a section of a needle/hub assembly showing a valve leaflet affixed by molding to the needle/hub assembly through a living hinge.

FIG. 14A is a perspective of a needle/hub assembly with portions removed for clarity of presentation.

FIG. 18 is a longitude section of a portion of the device showing the alternate needle/hub embodiment in three different positions in the device.

FIG. 19 is a section similar to the section seen in FIG. 18, but rotated 90°.

FIG. 41 is a magnified cross section along lines 41—41 of FIG. 38, wherein an unstretched elastic tube is disposed between a pair of tube distorting clamps.

FIG. 42 is a magnified cross section taken along lines 42—42 of FIG. 40 of the elastic tube and clamps seen in FIG. 38, the tube having been stretched and the clamps disposed about the tube to distort it from a round geometry.

FIG. 48 is a top elevation of the two part medical hub apparatus seen in FIG. 47, with one part separated from the other part.

DETAILED DESCRIPTION OF THE ILLUSTRATED EMBODIMENTS

In this description, unless a specific object is referenced, the term proximal is used to indicate the segment of a device normally closest to the patient when it is being used. In like manner, the term distal refers to the other (away from the patient) end. Reference is now made to the embodiments illustrated in FIGS. 1–48 wherein like numerals are used to designate like parts throughout. In some cases, parts having similar form and function to parts earlier cited are enumerated with prime numerals of the earlier cited parts.

Figure 1:
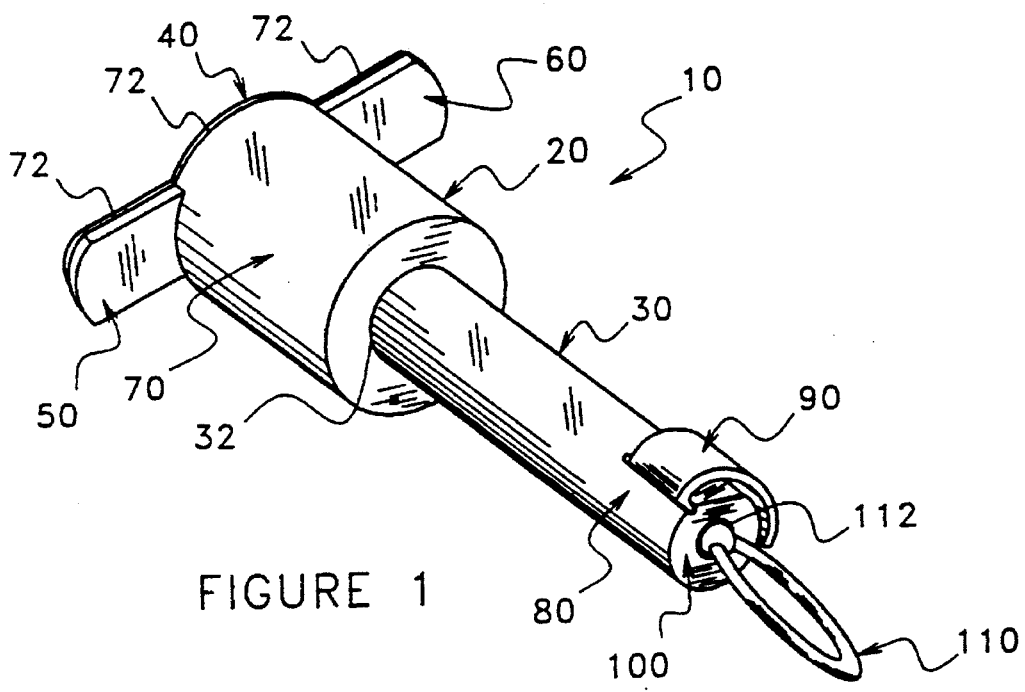
FIG. 1 is a perspective of a sealed blood draw device, showing the exterior of the device housing.

Reference is now made to FIG. 1 wherein an embodiment according to the invention of a blood draw device 10 is seen. As seen in FIG. 1, device 10 comprises a barrel section 20 and a needle containment section 30. In a completely assembled device, section 20 is securely affixed to section 30 along circular line 32 to provide protection for contents of the device from environmental damage and contamination.

Barrel section 20 comprises a planar seal 40 and a pair of left and right ear or handle parts, designated 50 and 60, respectively, and a hollow barrel 70. Planar seal 40 is adhesively attached to barrel section 20 within a plane area defined by continuous line 72 such that the hollow of barrel 70 is maintained in a sterile condition prior to use. To use device 10, seal 40 is manually removed. Of course, a different kind of seal may be used, such as a snap-on part which may be molded as a tether-attached part of section 20. The snap-on part is not shown, but production of such parts is well known in the art. A more detailed description of the internal parts of barrel 70 is provided hereafter.

Needle containment section 30 comprises an elongated tube 80, a flap 90, a proximally facing front face plate 100 and a pull-ring 110. Importantly, it should be noted that pull-ring 110 is separable from front face plate 100 at a frangibly detachable segment 112, which is described in more detail hereafter.

Figure 2:
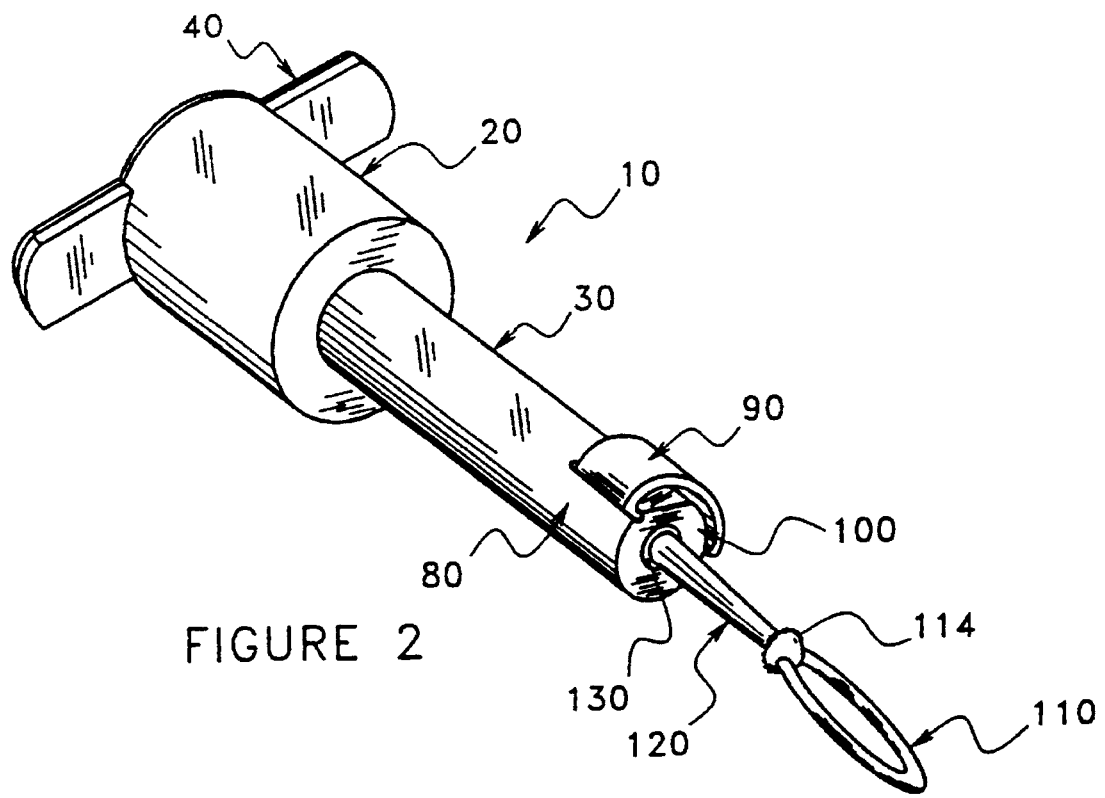
FIG. 2 is a perspective of the blood draw device seen in FIG. 1 from which a needle cover and associated needle (not shown) have been pulled by first frangibly breaking away the needle cover from a portion of the housing.
Figure 3:
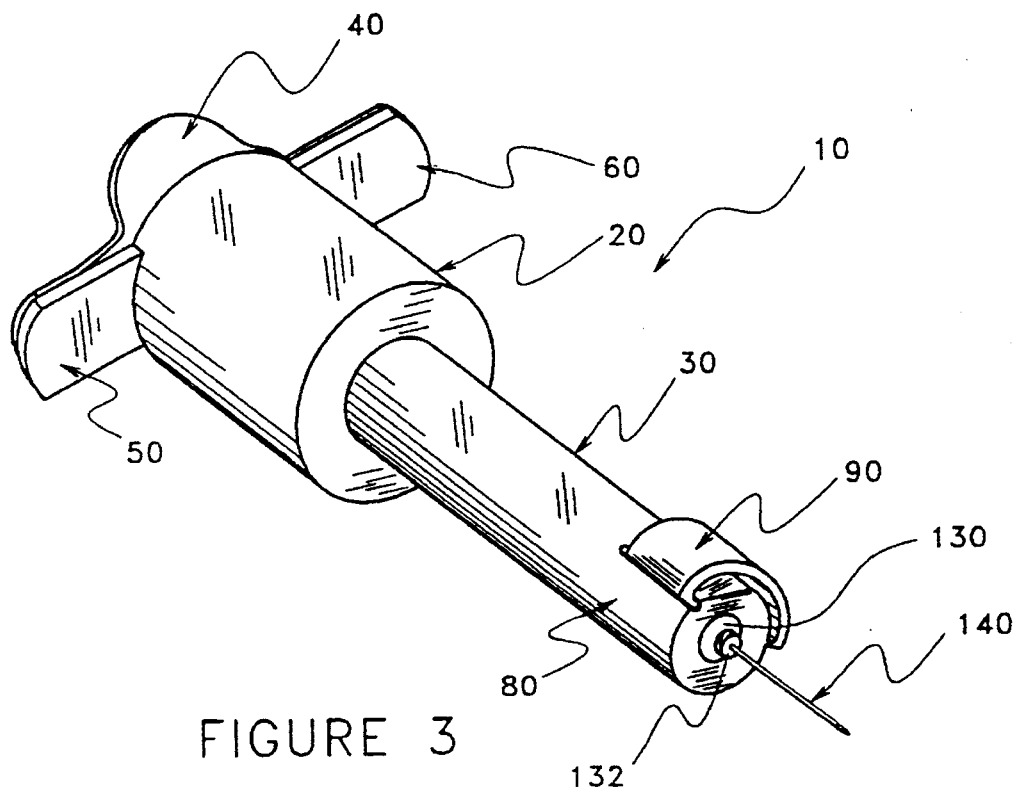
FIG. 3 is a perspective of the blood draw device seen in FIG. 2 showing a needle bared by cover removal and a partially removed seal which covered and protected the internal portion of a blood draw vacuum tube barrel, relative to the needle.
Figure 4:
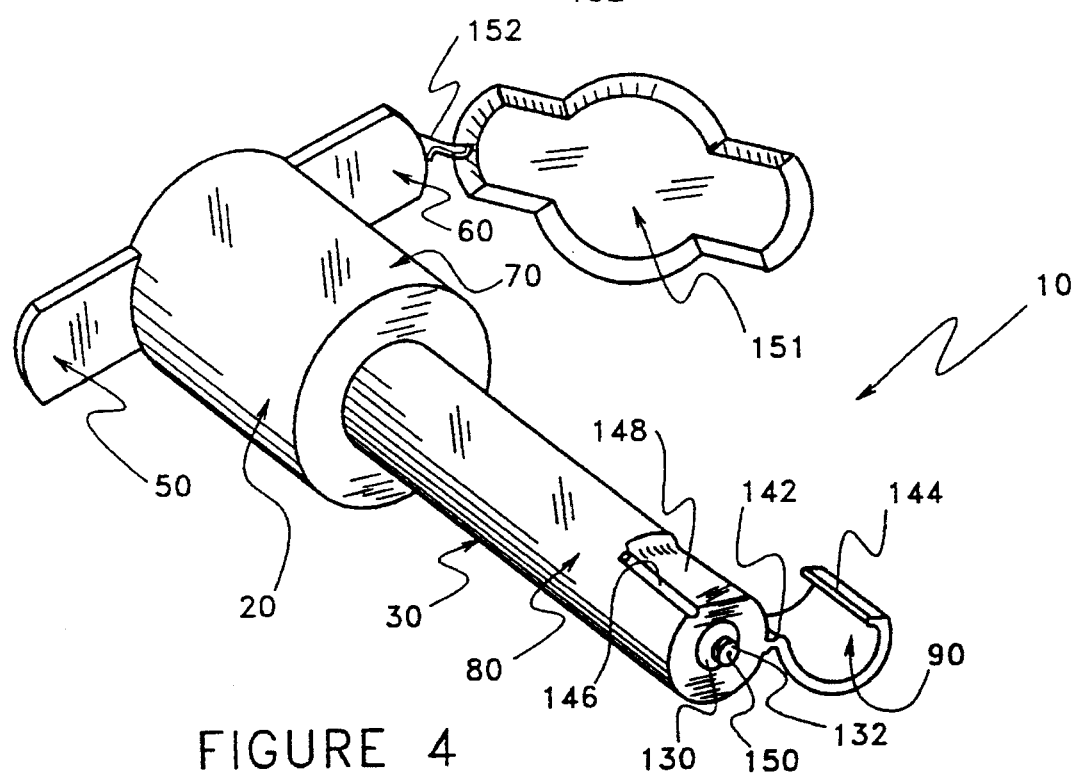
FIG. 4 is a perspective of the blood draw device showing displacement of a flap, seen in place in FIG. 3, the displacement permitting an area of the housing previously under the flap to be distorted, the distortion resulting in retraction of the needle into the housing.
Figure 5:
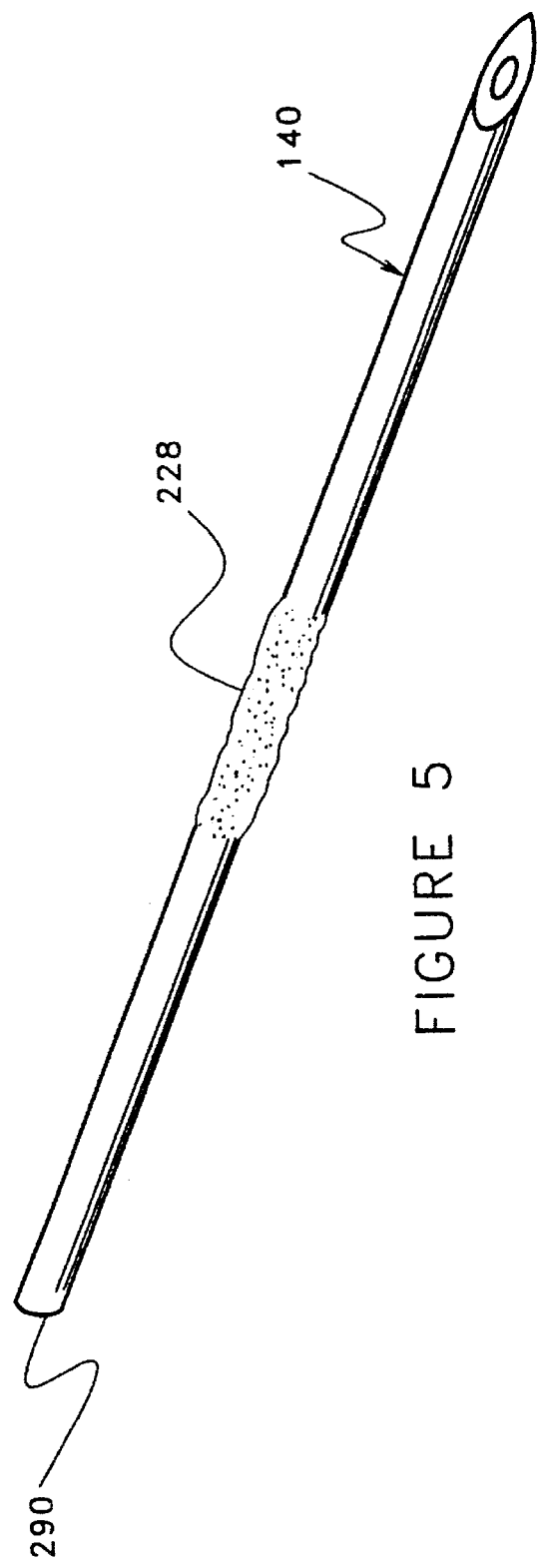
FIG. 5 is a greatly magnified perspective of a medical needle having a portion of the needle treated with a mold release.

Steps related to the use of device 10 are seen in FIGS. 2–4. In FIG. 2, pull-ring 110 has been detached from front face plate 100. Detachment of segment 112 produces a ragged collar 114. As pull-ring 110 is advanced from face plate 100, a needle cover 120 which is firmly affixed and integrally molded with pull-ring 110 appears through a hole created by removal of collar 114. Once pull-ring 110 is fully extended, a yoke 130 snaps into place about the hole produced by removal of collar 114. Structure of yoke 130 and related parts are disclosed in more detail later.

A next step is to remove seal 40 from barrel section 20. Seal 40 is seen to be in process of being removed in FIG. 3. In a next step, pull-ring and needle cover 120 are removed from device 10. Needle cover 120 is preferably attached to a hub 132 by a rotatably detachable coupler, such as by a threaded or bayonet type connector. In any event, the coupling attachment between hub 132 and cover 120 must be able to support a pull force at least as great as a retarding force imposed in the opposite direction by a retracting mechanism which is energized by the pull extending cover 120 until engagement of yoke 130. As seen in FIG. 3, a hollow medical needle 140 is bared upon removal of cover 120.

As best seen in FIG. 4, flap 90 comprises a living hinge attachment 142 to elongated tube 80. Flap 90 also comprises a hook latch 144 which is normally engaged in a groove 146 proximally disposed in tube 80. Located in flap 90, when disposed in groove 146 is a deformable area 148 of tube 80. While flap 90 is disposed and latched into groove 146, area 148 is fully protected from any deformation. Thus, during a medical blood draw procedure, flap 90 is latched into groove 146. Once blood acquisition has been completed, flap 90 is rotated by action of a single digit after which needle 140 may be retracted by depressing area 148. Retraction places needle 140 safely inside tube 80. Only access inside tube 80 and needle 140 is a hole 150 in hub 132 which is the essentially the same diameter as the cross sectional diameter of needle 140. Further, as is explained later, needle 140 is securely held well away from hole 150. Retraction mechanisms for needle 140 are describe in detail hereafter.

Also seen in FIG. 4 is a snap-on cover 151 affixed by a tether 152 to handle 60. Cover 151 is an alternative embodiment to seal 40. Cover 151 has the advantage of not requiring a cover part to be made separately from barrel section 20. However, to provide assurance that cover 151 has not been opened previous to a procedure to which device 10 is uniquely dedicated, an additional seal, such as a shrink wrap about exterior edges of cover 151 and related parts of handles 50 and 60 and tube 80 should be used. Making of parts attached by tether is well known in the art.

Reference is now made to FIG. 6 wherein an exploded view of one embodiment of device 10 is seen to comprise needle containment section 30, a needle/hub part 160, a valve disk 170, an elastic tube 180 and barrel section 20. Attention is first drawn to needle/hub part 160 which is seen magnified for more clarity of details in FIGS. 7–9.

Part 160 comprises medical needle 140, a fore part 190 proximal to the sharp end of needle 140, a central part 192, and an aft part 194. Normally unseen extensions of needle 140 through part 160 is indicated by double dashed lines 196 and 198 for clarity of extent of needle 140 passage through part 160. Fore part 190 comprises yoke 130, hub 132, an annular groove 200, an annular stop 202 and an elbow shaped extension 204 which comprises an outwardly extending part 206. Central part 192 comprises a frangible bridge 208 and a support 210. Aft part 194 comprises a short shaft 212 and a tube hub 214. Part 160 is preferably molded as a single part with end-to-end continuity between parts 190, 192 and 194. Aft part 160 is firmly and securely affixed to needle 140 while fore part 190 is only slidably affixed and otherwise free to move along needle 140 when bridge 208 is franged. Aft part 160 may be affixed adhesively by methods which are well known in the art.

Figure 7:
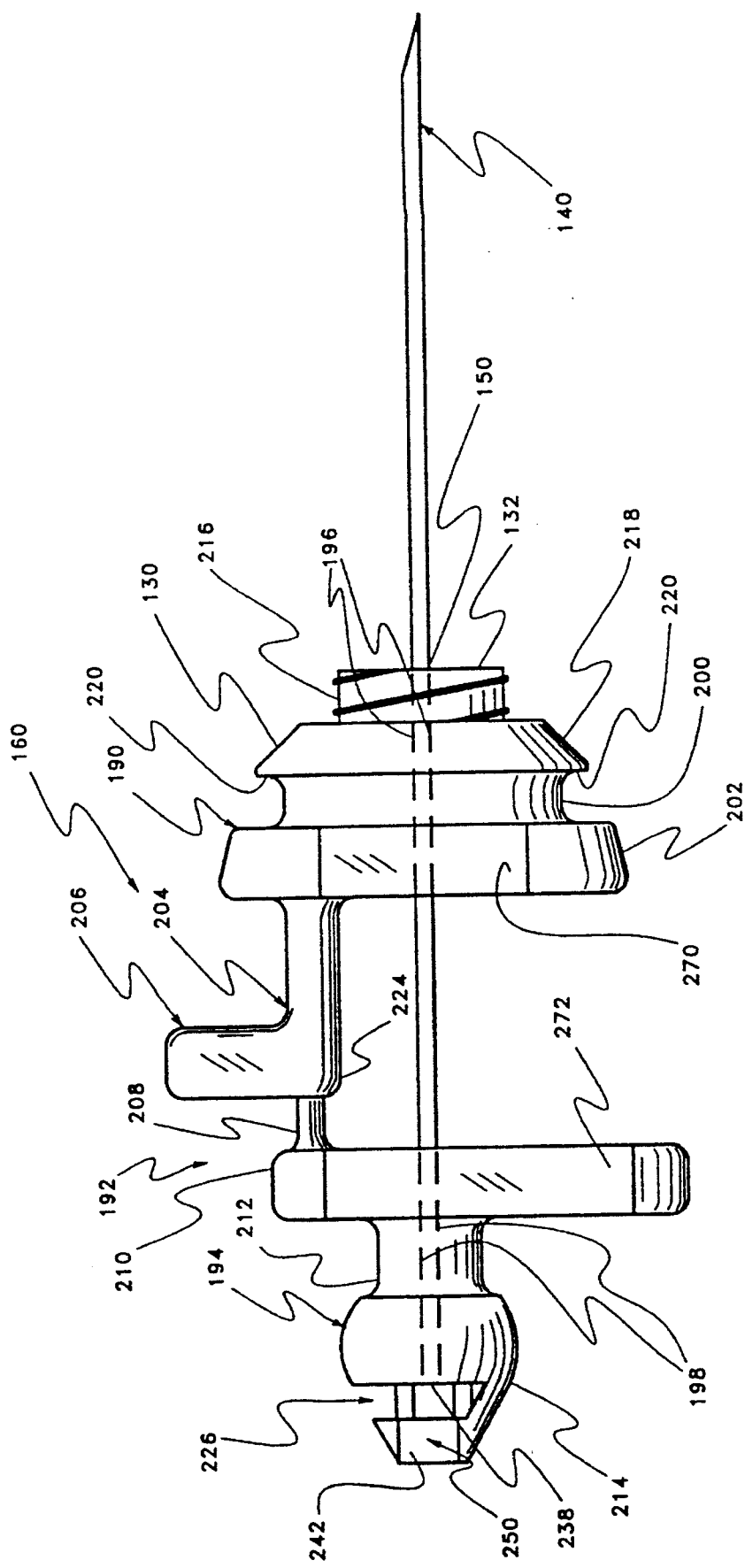
FIG. 7 is a lateral elevation of a needle/hub assembly which initially resides within the housing and is separably affixed to the cover.
Figure 8:
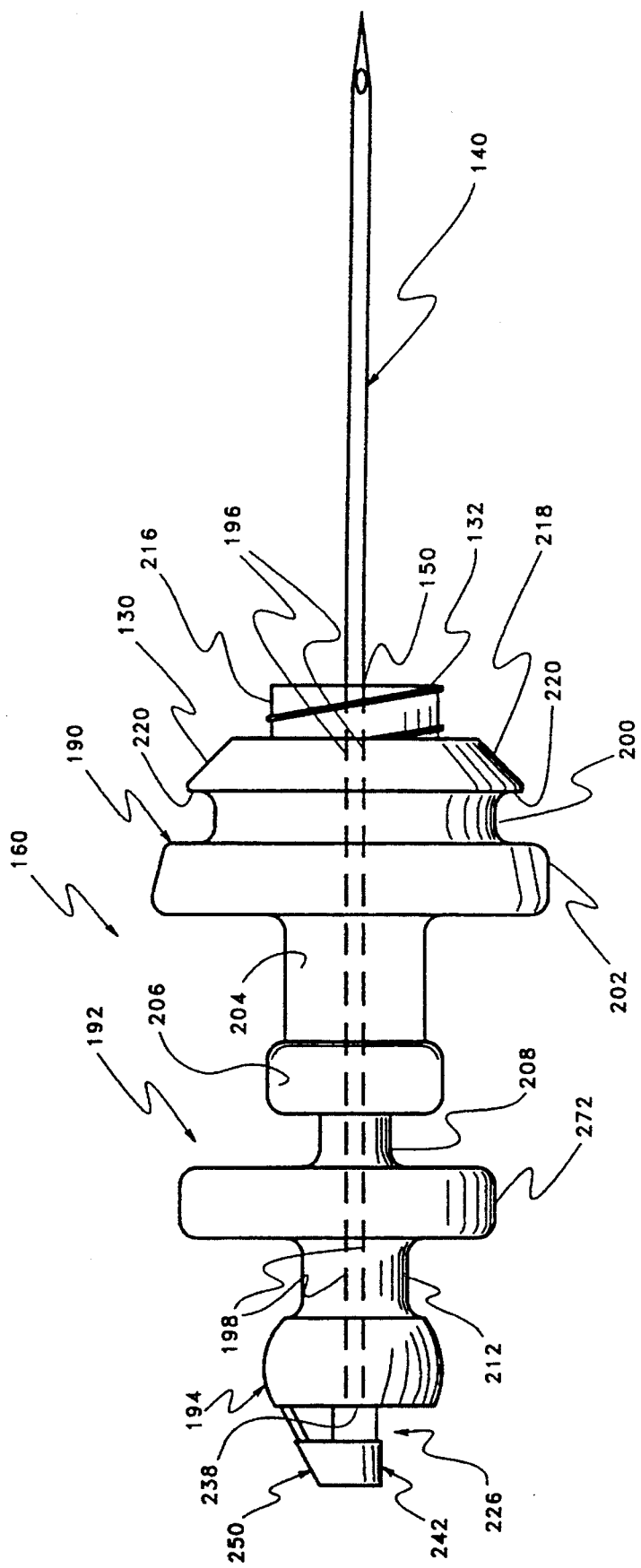
FIG. 8 is a top elevation of the needle/hub assembly seen in FIG. 7.
Figure 9:
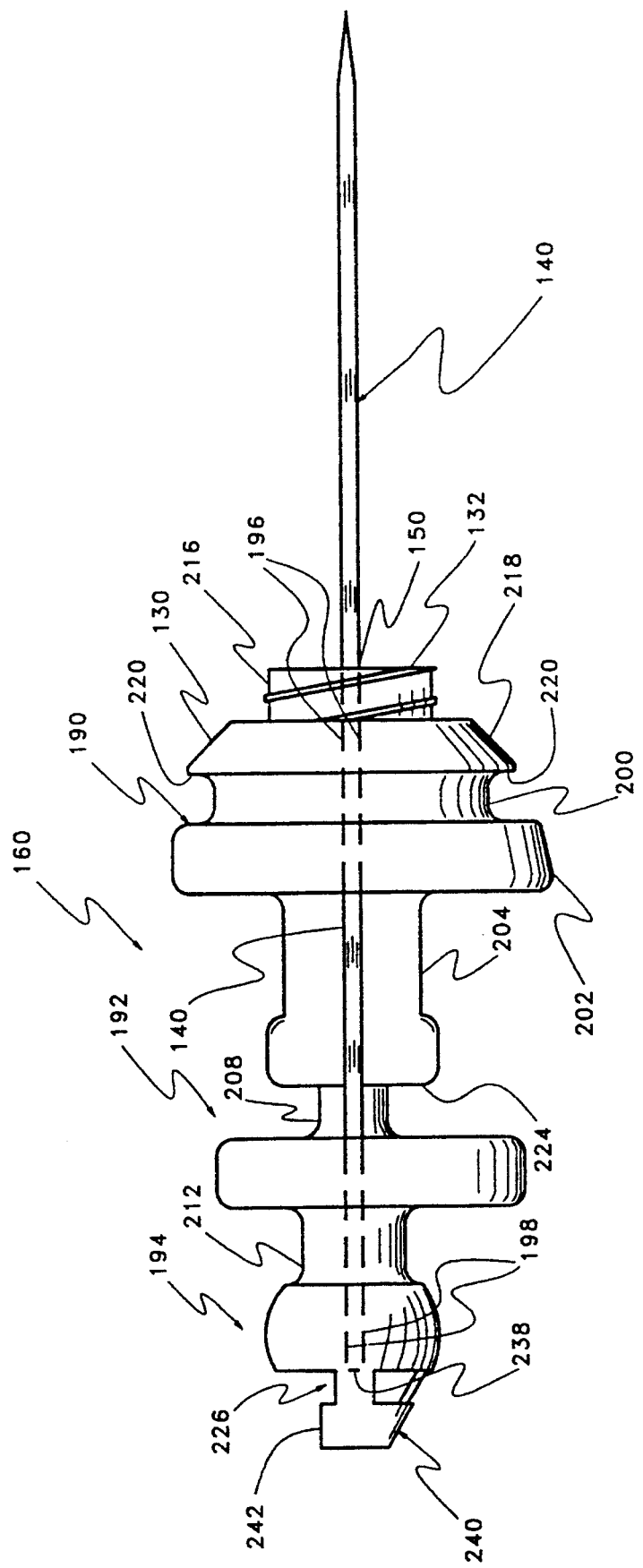
FIG. 9 is a bottom elevation of the needle/hub assembly seen in FIG. 7.

Hub 132 comprises a releasable connector component which may be in the form of a threaded surface 216 as seen in FIGS. 7–9. Yoke 130 comprises a sloped annular face 218 and a transverse latching surface ring 220 distal to and juxtaposed face 218. Groove 200 is interposed between and contiguous with ring 220 and stop 202. Function and use of yoke 130, groove 200 and stop 202 are described in detail hereafter.

As best seen in FIG. 7, an extension 204 protrudes distally from stop 202 via a lateral bar 222 to an elbow 224 where extension 204 makes an orthogonal bend to form upward and outwardly extending part 206. Bridge 208 is a part which is narrow in both transverse dimensions to govern the degree of pressure required to frange bridge 208 from extending part 204. One of the surprising aspects of the instant invention is the force which may be placed upon bridge 208 when pulling against a force retaining memory element used in retracting needle 140 without breaking bridge 208 away from extension 204. Clearly, if even a nominal torque is place upon bridge 208 during a pull, bridge 208 might break. Close tolerances should be maintained between needle 140 and fore part 190 to reduce and keep such torque at a level which does not cause bridge 208 to break while needle 140 is being pulled forward. The method for achieving close tolerances between needle 140 and fore part 190 is disclosed hereafter.

Bridge 208 is contiguous with a support 210. Medially disposed about needle 140 and distally connected to support 210 is shaft 212. Tube hub 214, connected to shaft 212 provides a valve leaflet containment basket 226 wherein a one-way valve leaflet may be placed and trapped by a tube mounted on hub 214. Basket 226 is better seen in FIG. 10. Basket 226 comprises a slot formed by a distal facing side 228 and a proximal facing side 230, the two sides being connected by a bottom plate 232 and two side members 234 and 236.

Side 228 is a smooth planar face comprising a non-protruding blunt end 238 of needle 140. Also seen in FIG. 10 is a valve leaflet disk 240. Disk 240 is made of compliant synthetic resinous material which, under pressure, deforms to seal end 238 of needle 140 against regurgitant flow when pressure downstream from needle 140 is greater than upstream pressure. This seal is very important to contain blood within needle 140 upon retraction of needle 140. To assure a low resistance to flow from needle 140, disk 240 comprises a plurality of raised feet which space the distal side of valve disk 240 away from side 230. That spacing and various cuts, designated 242, 244, 246 and 248 in distal end 250 of aft part 194 provide a low resistance pathway for effluent flow from a patient.

Care should be taken such that the diameter, designated by A arrows, of disk 240 is less than the sum of distances indicated by arrows B and C, but greater than B plus the diameter of needle end 238 to assure that regurgitant flow is always stopped, but disk 240 is not inadvertently held in an open condition by a tube stretched over hub 214.

Another embodiment of a one-way valve is seen in FIG. 10A. If hub 214 is made of sufficiently resilient and compliant material, a leaflet valve may be integrally molded on the distal end of the hub. In the embodiment of FIG. 10A, a thin planar wafer 252 is integrally connected to a hub 214' (which is otherwise similar to hub 214) by a living hinge to curtail proximal flow through needle 140 at end 238 while being permissive to distal effluent flow.

In the embodiment seen in FIG. 6, retractive force is provided by a stretched tube. For this purpose, tube 180 is cut to a predetermined length allowing for displacement about a proximal and a distal hub and for a length of the tube which stretches when device 10 is cocked as needle 140 is pulled outward for use. Tube 180 comprises a proximal end 254 and a distal end 256. Tube 180 may be made from any elastic material which is effectively inert to blood and which can provide a return force sufficient to retract a needle directly from a patient into safe containment. (An elastic force in the range of two to four pounds is recommended although it has been found that a return force in the range of one pound is adequate to remove needle 140 from a patient and retract it into a housing.)

It is preferred that the tube be capable of being stretched at least a length of four times its resting length. However, the currently preferred material is latex. Note that a needle of one inch in length should require a tube not greater in length than about one-half inch.

Barrel section 20 comprises a plurality of internally disposed parts, generally designated 258. Parts 258 comprise an elongated stabilizing key 260, a distal tube hub 262, an assembly plate 264, an rear delivery needle 266 and a needle cover 268.

Stabilizing key 260 is an elongated rod which stretches from assembly plate 264 to beyond stop 202 when device 10 is assembled and tube 180 is relaxed. Hub 262 is formed about needle 266 to provide a piercing entry to a low pressure collection tube (not shown) such as a Vacutainer® (Manufactured and distributed by Becton Dickinson of Franklin Lakes, N.J.). As is standard practice in apparatus which is used to provide entry to low pressure collection tubes, a pierceable needle cover 268 is provided to deter leakage as collection tubes are replaced.

Figure 11:
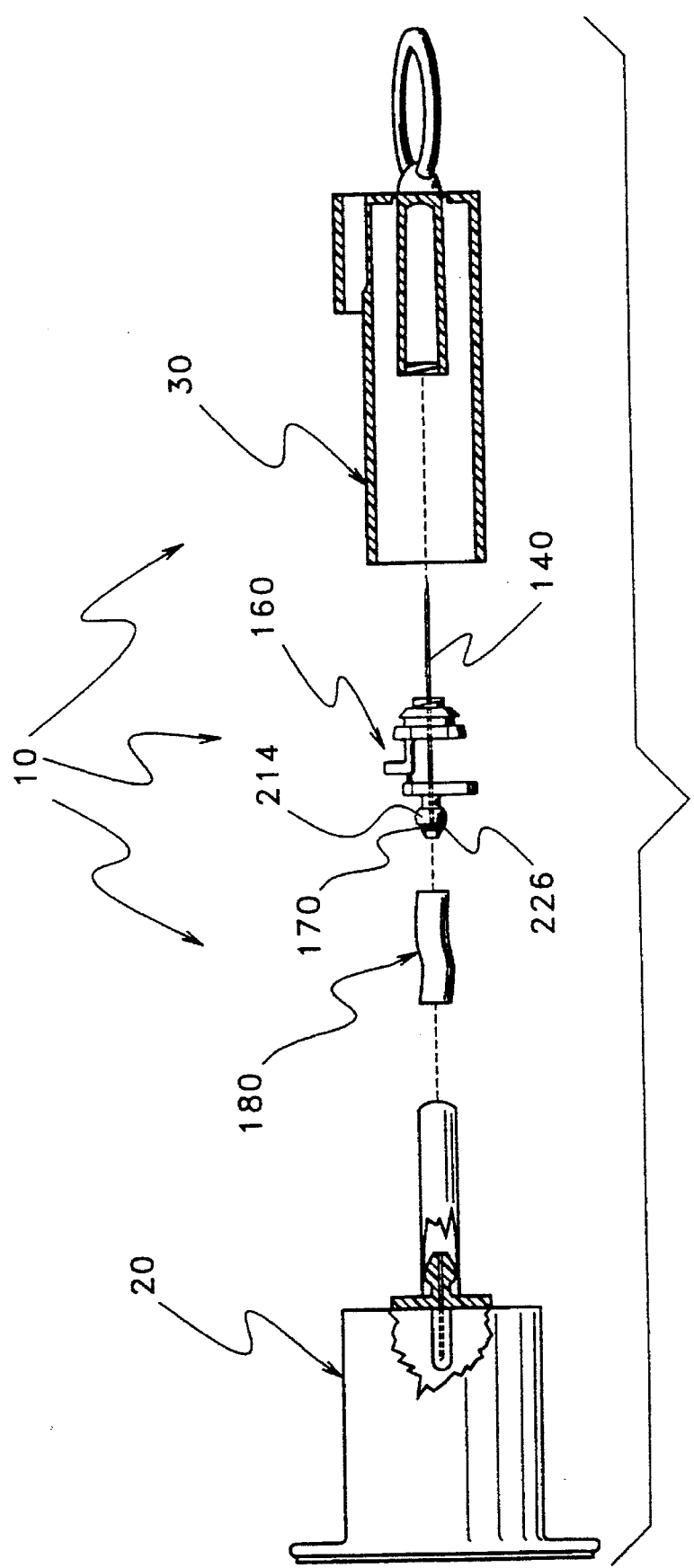
FIG. 11 is an exploded view of the device of FIG. 6 with a first assembly step completed.

FIGS. 6, 11, 12, 13 and 14 demonstrate simplicity of assembly of device 10. FIG. 6 is representative of parts in a preassembled configuration. Step one in assembly comprises insertion of valve disk 170 into valve containment basket 226 as seen in FIG. 11. Note that step one is not required when a valve leaflet such as a valve formed by wafer 252 is an integral part of tube hub 214'.

Figure 12:
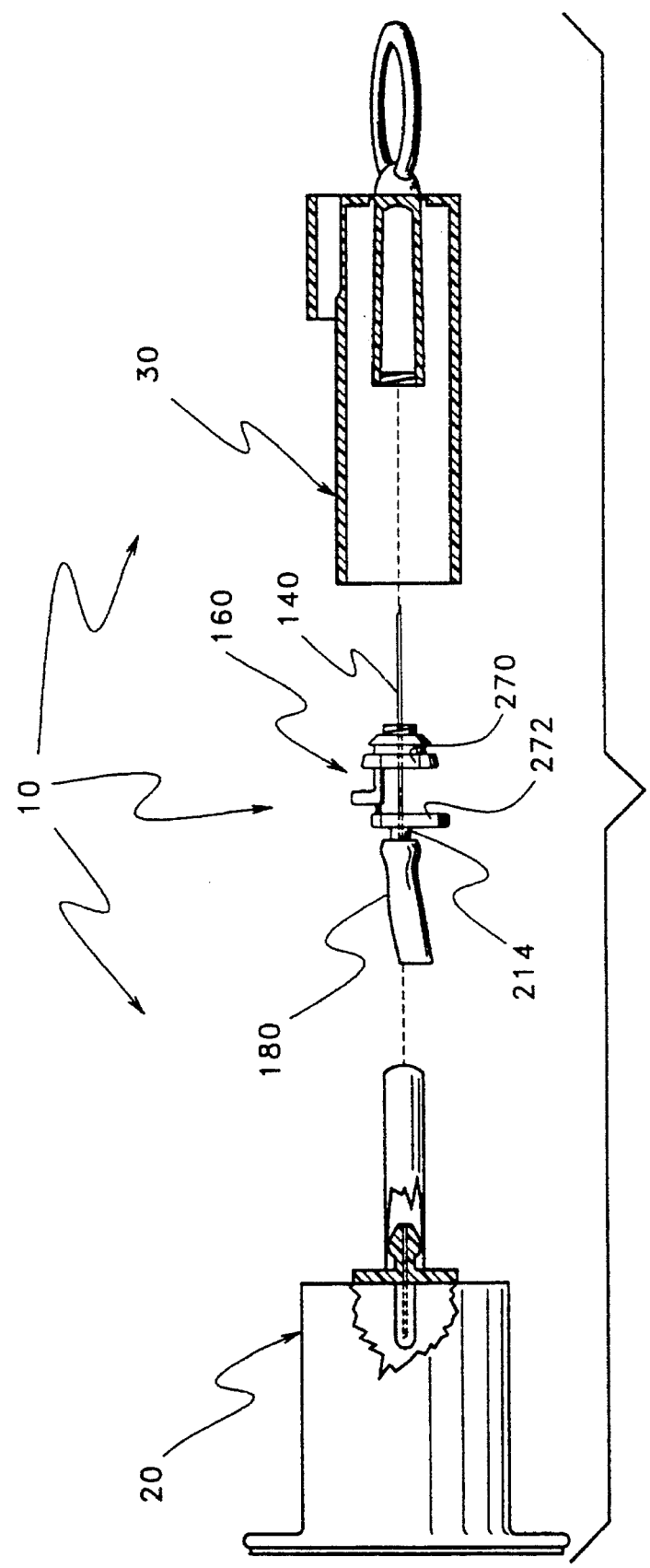
FIG. 12 is an exploded view of the device of FIG. 7 with a second assembly step, comprising attaching an elastic tube, completed.

Attachment of tube 180 to hub 214 (or hub 214' in the case of the embodiment seen in FIG. 10A) is seen in FIG. 12. To assure that tube 180 is securely affixed to hub 214 (or 214') it is recommended that an adhesive be applied to a proximal portion of hub 214 (or 214') immediately before tube 180 attachment. A suitable adhesive material should be used and care should be taken to assure that no inappropriate blood reactive material is allowed to contact areas where blood may flow. One adhesive which has provided satisfactory adhesion in models of the invention which have been reduced to practice is Duro Super Glue, manufactured and distributed by Loctite Corporation, Cleveland, Ohio 44128, commonly known as Super Glue, although other adhesive materials known in the art may also be used within the scope of the invention. All such adhesives should be qualified to be compatible with use in a medical application.

Figure 13:
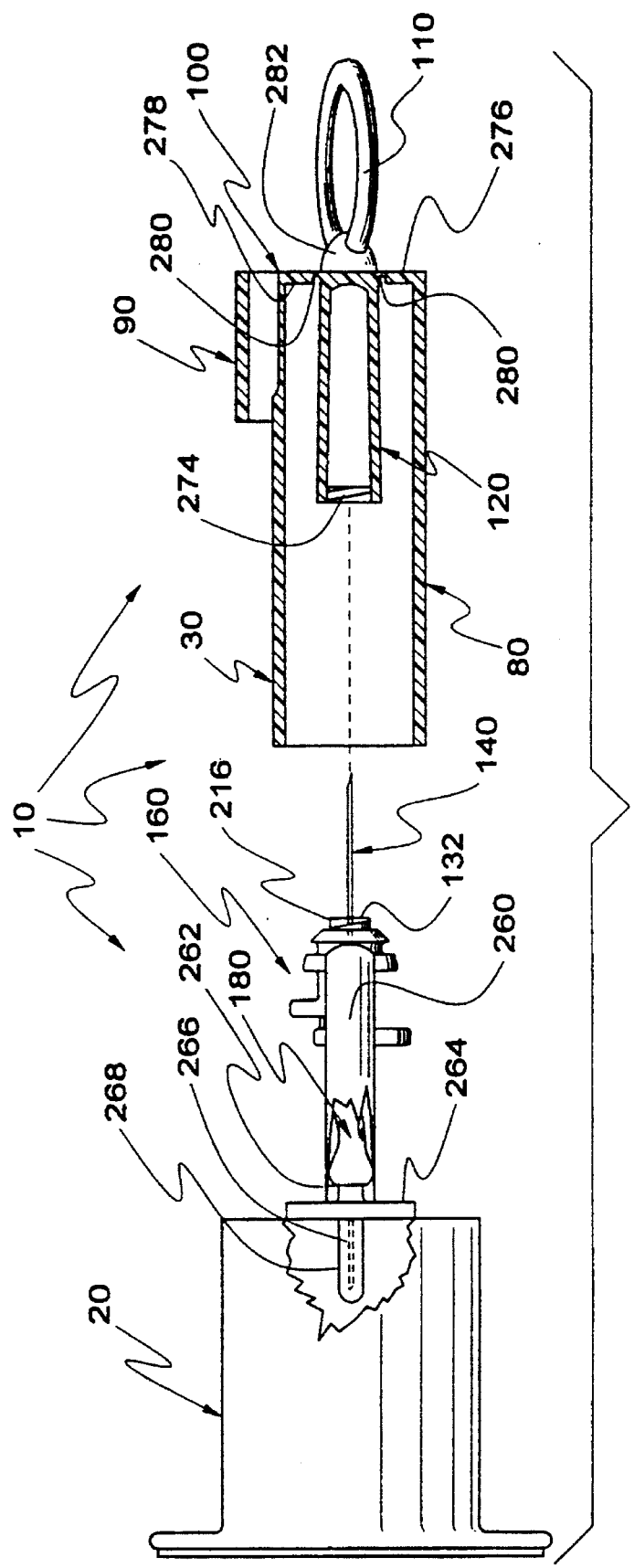
FIG. 13 is an exploded view of the device of FIG. 7 with a third assembly step of attaching the elastic tube to the barrel part. (Note that a perspective of a completely assembled device is seen in FIG. 1.)

Completion of a fluid flow path from needle 140 is seen in FIG. 13. Tube 180 is connected on distal end 256 to hub 262. At the same time stabilizing key 260 is engaged in a locking slot 270 (See FIG. 14A) disposed in annular stop 202. Key 260 is formed to slide laterally into and out of slot 270 and fit snugly therein when tube 180 is relaxed (i.e. during assembly). In this manner, no undue torque or rotational stress is placed upon frangible bridge 208 during assembly. To provide a pathway for key 260 past support 210, a material relieving flat 272 is formed along the plane of travel of key 260 in support 210.

As a next step needle containment section 30 is disposed about the assembled parts. Needle cover 120 comprises a female connecting segment 274 which is complementary to the male connector provided by hub 216. Cover 120 is preferably affixed by rotating section 30 relative to hub 216 although press-on connections which can withstand pull forces exerted by an elongating tube or spring or the like may also be used.

As needle cover 120 is connected to hub 216, tube 80 of section 30 engages assembly plate 264. Tube 80 is securely affixed to assembly plate 264 by adhesive or ultrasonic welding processes which are well known in the art of plastics assembly. In this manner, a union is provided to protect needle 140. As such, sections 20 and 30, in combination provide a housing for needle 140 which may be used without additional packaging for transport.

Attention is now drawn to front face plate 100 of section 30. Face plate 100 comprises a proximal surface 276 and a distal substantially planar surface 278. Disposed in surface 278 is an annular groove 280. Groove 280 completely encircles the area where cover 120 integrally connects to plate 100 and a ring hub 282 which is integral with the proximal end of cover 120. Hub 282 also integrally connects ring 110 to section 130. Groove 280 is of sufficient depth in plate 100 to permit facile frangible separation by a positive tug, twist or pull on ring 110 while retaining sufficient material to provide a sealed container and a sturdy and safe transport container. Products having such seals are available in commerce.

Figure 15:
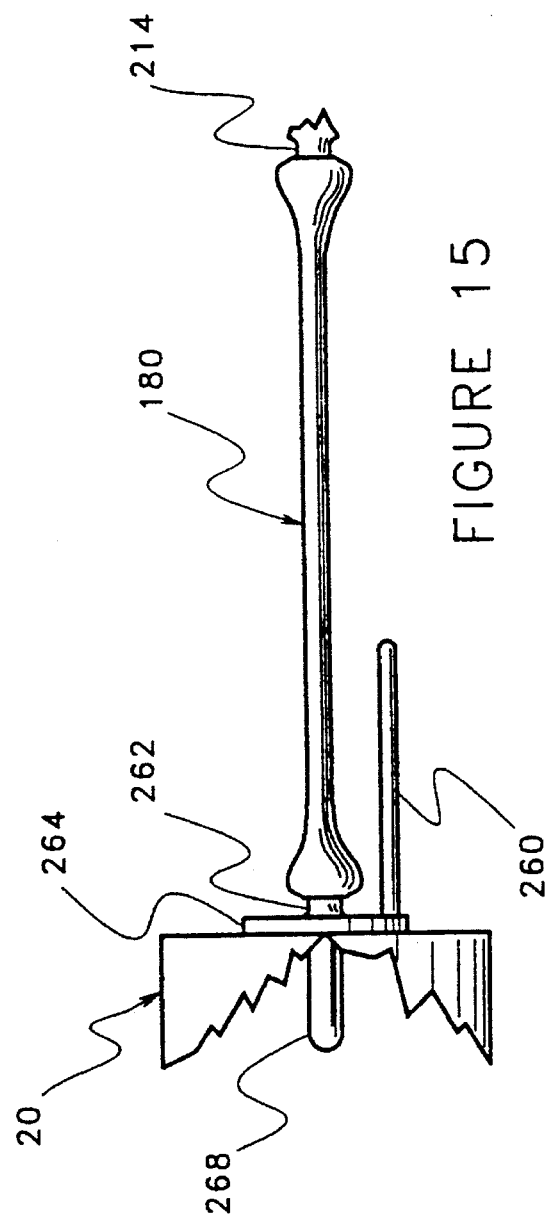
FIG. 15 is a lateral elevation of an elastic tube stretched between hubs of the barrel and needle/hub assembly parts.

Frangibly separating ring 110 and cover 120 from section 30, as seen in FIG. 2, causes tube 180 to be stretched between separating hubs 214 and 262 as is best seen in FIG. 15. Note that needle hub part 160 and, in particular, locking slot 270 is pulled away from key 260 by the same action. For this reason, it is advisable to make groove 280 and cover 120 somewhat asymmetric to minimize rotation during tube extension. One of the material attributes which permits tube 180 to be used to store energy to retract needle 140 and to act as a pathway for fluid communication between needle 140 and needle 266 is that the internal lumen of a tube remains patent when stretched. The diameter of the lumen is reduced but not closed as the tube elongates.

Figure 14:
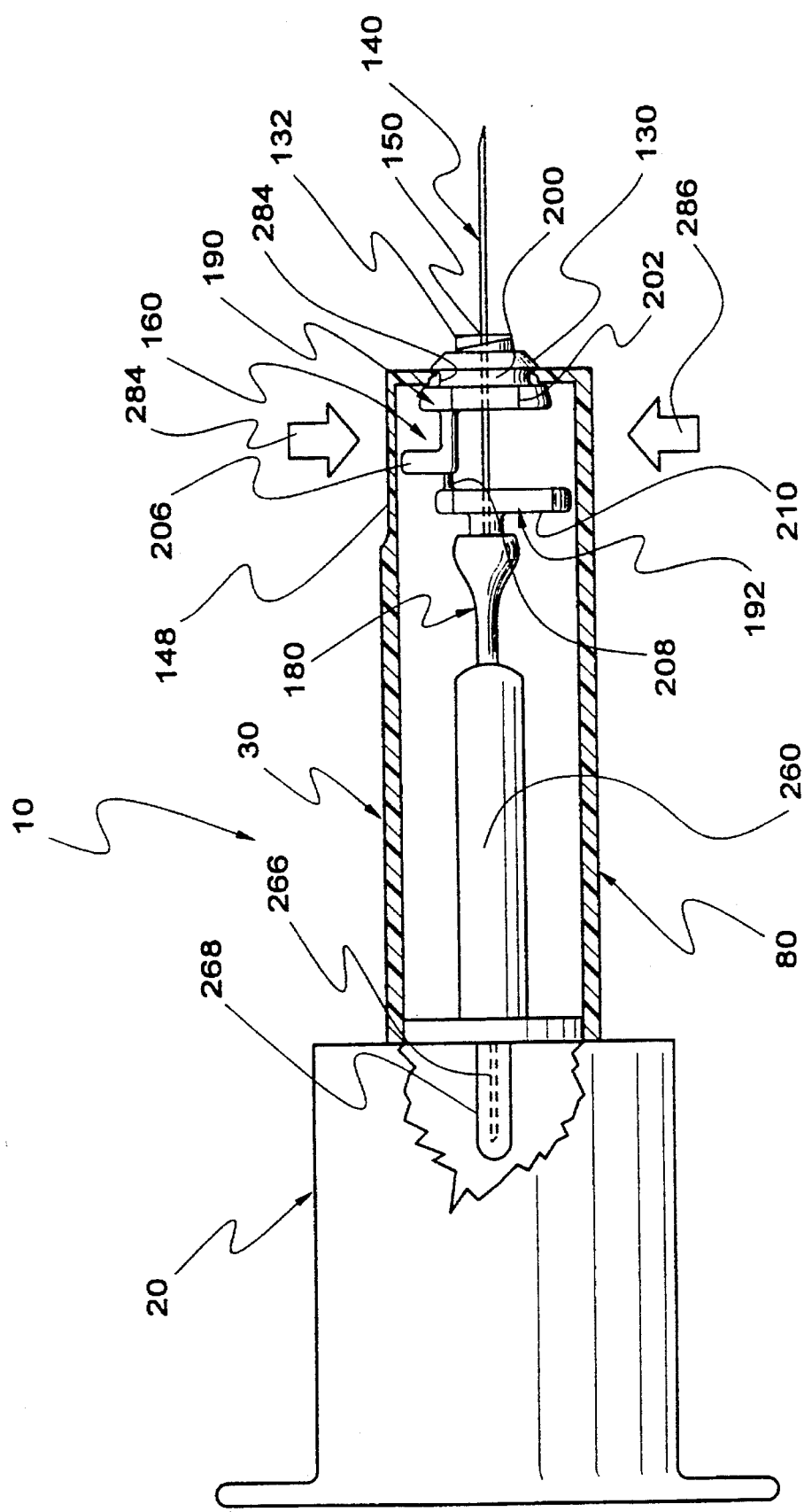
FIG. 14 is a section of a used device prior to retracting the needle.

When ring 110 and cover 120 are separated from section 30 by franging plate 100 at groove 280, an annular hole 284 is created in plate 100. As seen in FIG. 14, when needle/hub part 160 is pulled proximally, cover 120 and then yoke 130 are pulled through hole 284. The slanting annular surface 218 of yoke 130 as best seen in FIGS. 7–9, comprises a proximal diameter which is smaller than the diameter of hole 284 and a distal diameter which is larger than hole 284. However, the distal diameter is such that yoke 130 passes through hole 284 due to the "give" of material from which section 30 is made. Groove 200 has a width which permits plate 100 to be engaged therein after yoke 130 is pulled through hole 284. The proximal face of stop 202 has a diameter which is greater than hole 284 causing part 160 to be firmly affixed to plate 100 when yoke 130 passes through hole 284 as seen in FIG.

Once the procedure involving needle 140 is completed, and preferably while needle 140 is yet disposed in a patient's blood vessel, needle 140 is automatically retracted. The retraction process involves (1) hingeably relocating protective flap 90 (as seen in FIG. 4) and (2) applying pressure upon part 206 through area 148 of tube 80 to frangibly separate fore part 190 from aft part 192 by breaking bridge 208 of part needle/hub part 160.

Flap 90 is commonly released from attachment to tube 80 at groove 146 by inserting a thumb or finger under a portion of flap 90 and lifting. Bridge 208 is broken by applying pressure, preferably between a thumb and forefinger, in the direction of arrows 284 and 286. Franging forces (i.e. shear forces) are thus applied through area 148 to part 206 and an inferior portion of tube 80 to support 210. Note that substantially all other forces applied to bridge 208 are those of tension caused by longitudinal stretching of tube 180. For this reason, bridge 208 comprises a geometric shape which is conducive to breaking when imposed upon by shear forces, but capable of withstanding large amounts of tension.

One of the major reasons that substantially all of the forces placed upon bridge 208 during extending a retractive mechanism is a close tolerance held between needle 140 and fore part 190. As mentioned hereinbefore, part 190 is made to be free of needle 140 such that it can slide thereon. To maintain the tight tolerance and to provide an inexpensive method for manufacture of part 160, needle/hub part 160 is preferably molded as a unit about needle 140. Part 160 is preferably injection molded.

To permit fore part 190 to be molded about needle 140, yet remain slidably free, a thin coat of mold release is applied about needle 140 prior to molding. By applying a coat of mold release 288 in an area wherefore part 190 is molded, fore part 190 remains only slidably attached to needle 140. Of course, at the distal end 290 of needle, aft part 194 is firmly and securely affixed by the molding process causing needle 140 to be retracted when tube 140, attached to aft part 194, is permitted to contract. Note that, when needle 140 is retracted through yoke 130 and hub 132, the only access into tube 80 is through hole 150 which has substantially the same diameter as needle 140. Of course, once needle 140 is retracted, it is irretrievably held inside tube 80 by a relaxed tube 180.

Except for needle 140, which is made of medical grade steel, needle/hub part 160 is made from a moldable material having sufficient tensile strength to withstand pull pressures of device 10 yet be facilely separated at bridge 208. As such, part 160 is preferably made of synthetic resinous material, such as polyurethane, polypropylene or polyethylene. For an experimental device, the synthetic resinous material used was polyurethane sold as Quik Cast distributed by TAP Plastics, Dublin, Calif. 94568, however many currently commercially available materials may be used within the scope of the invention.

Barrel section 20 is likewise preferably made from synthetic resinous material. Barrel section 20 is also preferably molded about rear delivery needle 266. The same material which is used in currently commercially available barrels used with vacuum based blood drawing tubes (e.g. Vacutainers®) may be used. Needle cover 268 may be one of the same as Vacutainer® barrel needle covers now commonly used.

Needle containment section 30 is preferably made by a single molded process. Mold material should be selected such that it provides sufficient material strength to engage and hold the hub 132 connection through the pull process, sufficiently flexible when made as a thin membrane to permit distortion sufficient to break bridge 208, and frangibility for facile opening as at groove 280. The material is preferably a synthetic resinous material and may be polyethylene, although other materials meeting flexibility, medical compatibility and strength requirements may be used.

Figure 16:
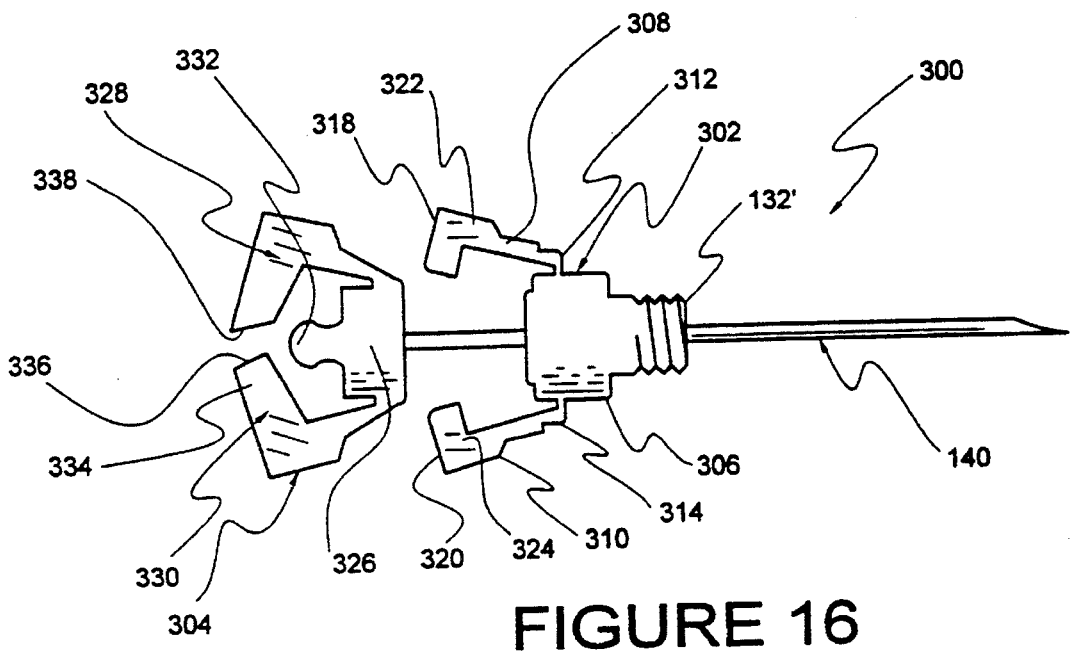
FIG. 16 is a side elevation of an alternative embodiment of a needle/hub assembly showing a first part which is molded about and securely affixed to the needle and a second part which is molded about the needle but which is free to slide longitudinally along the needle.

Reference is now made to FIGS. 16–20 which relate to another embodiment of the invention. This embodiment is similar to the embodiment seen in FIGS. 6–14 in general form and function, but does not depend upon a frangible part to release and retract the needle. As seen in FIG. 16, a needle/hub assembly 300 comprises two parts, designated fore-part 302 and aft-part 304, which are formed about a needle 140. Parts 302 and 304 may be molded about needle 140 simultaneously. Part 302 is preferably molded about a segment of needle 140 to which a mold release has been applied, as earlier described. (See FIG. 5.)

Fore-part 302 comprises a central body 306 and a pair of outwardly extending wings or arms, individually designated 308 and 310. Each arm 308, 310 is connected to central body 306 by a biased hinge 312 and 314, respectively. The biasing of hinges 312 and 314 is preferably formed as a part of the molding process. Such hinges are well known in the art; as an example note hinges on telephone connectors. Each arm 308,310 is biased to extend outwardly from central body 306 a predetermined distance. Disposed at the outer end 318, 320 of each arm 308, 310, respectively, is an inwardly projecting latching extremity 322,324.

Central body 306 comprises a cover connecting hub 132' which is similar in form and function to hub 132. A portion 316 is disposed distal to hub 132' where hinges 312 and 314 are attached.

Aft-part 304 comprises a central body part 326, a pair of outwardly extending and biased wings or arms 328 and 330 and a tube hub 332. Wing 330 comprises an inwardly projecting strut 334 which ends at a clamping face 336. In opposing fashion, wing 328 comprises an inwardly projecting jaw 338. Function and used of the various parts of fore-part 302 and aft-part 304 are disclosed in detail hereafter.

Figure 17:
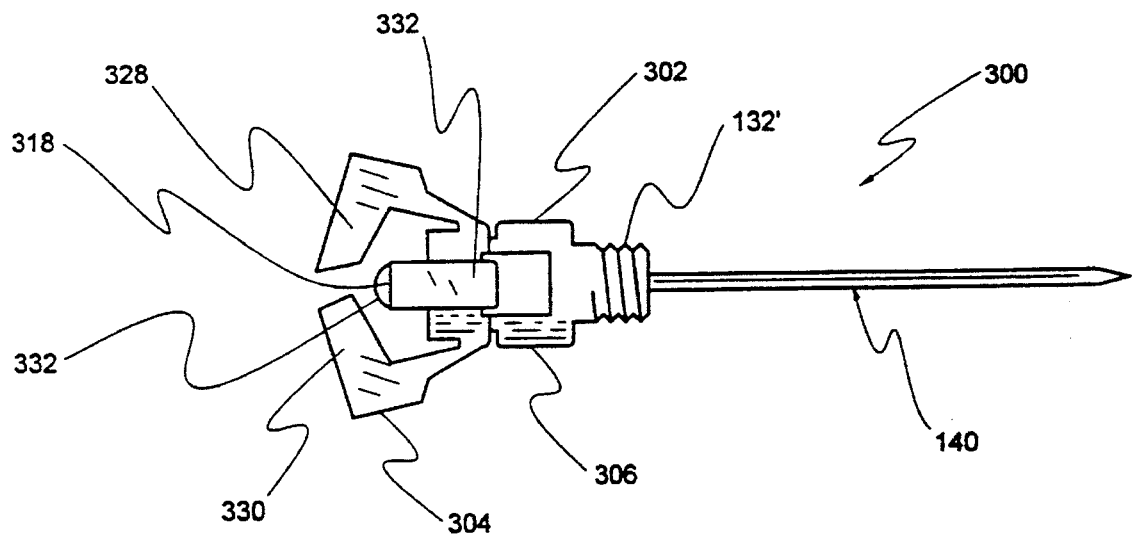
FIG. 17 is a side elevation of the embodiment seen in FIG. 16 with the slidable part moved to an adjoining position relative to the first part.

As mentioned earlier, fore-part 302 is preferably molded about needle 140, but not attached thereto, except by the natural engagement provided by materially surrounding the circumference of a portion of the needle. This permits fore-part 302 to be rotated 90° and moved into linkable proximity with aft-part 304 as seen in FIG. 17.

Figure 21:
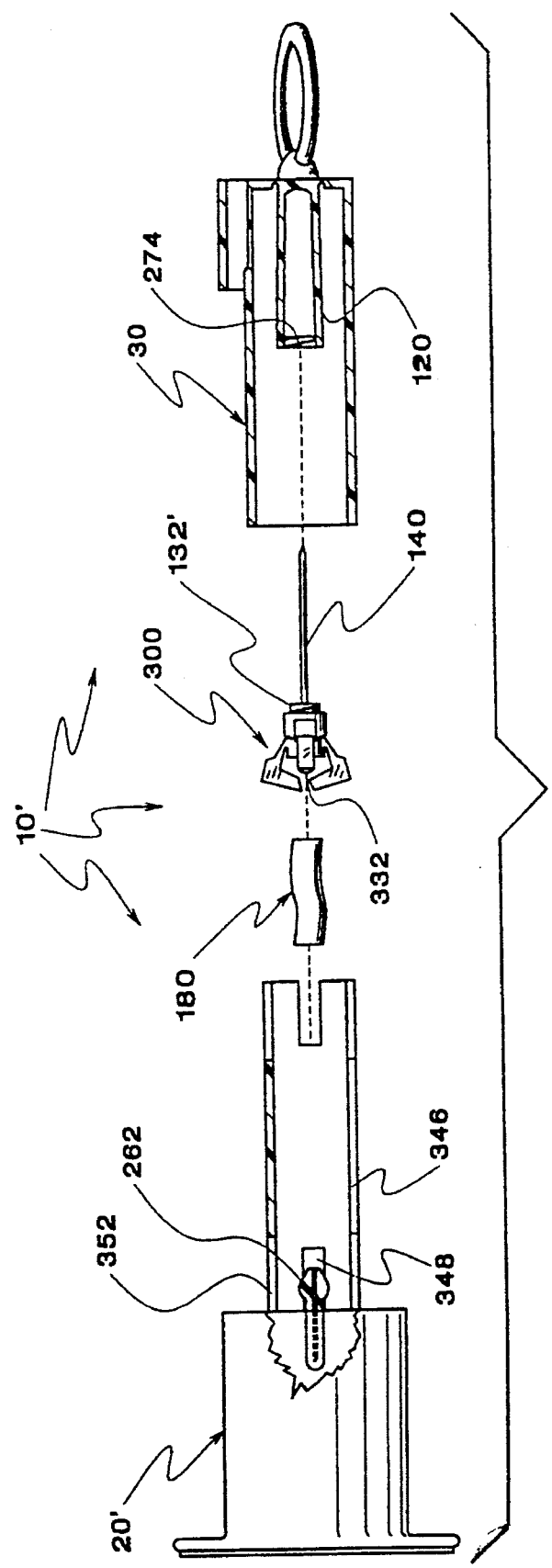
FIG. 21 is an exploded perspective of the device comprising the alternate needle/hub embodiment.

Parts content in this second embodiment of blood draw device 10 is best seen in FIG. 21. This second embodiment comprises a barrel section 20', tube 180, needle hub assembly 300 and needle containment section 30.

Barrel section 20' is substantially the same as barrel section 20 except for the substitution of a guide-catch cylinder 340 integrally and medially disposed on a fore portion of barrel section 20' rather than the stabilizing key similarly disposed upon barrel section 20.

Figure 20:
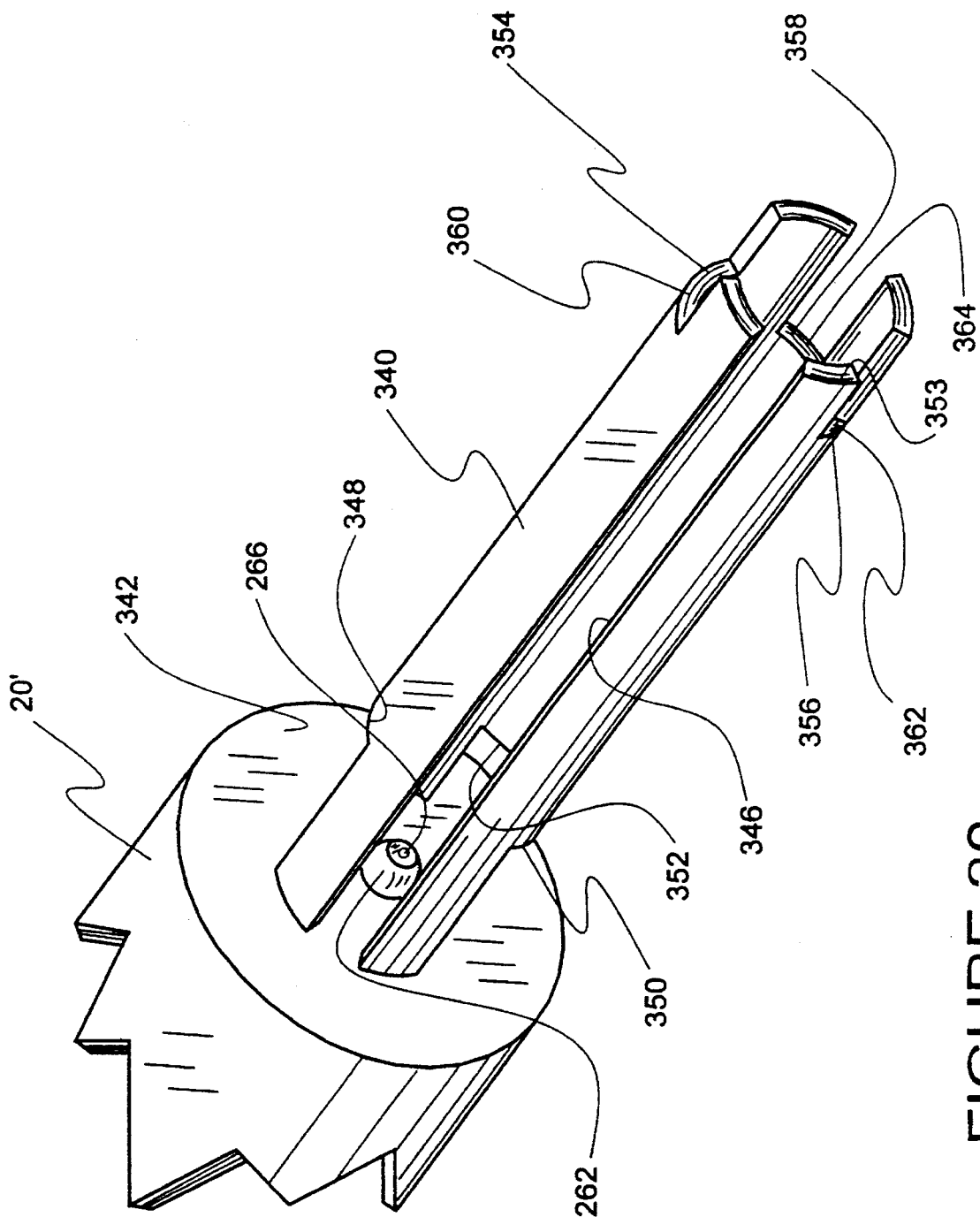
FIG. 20 is a perspective with some parts removed for clarity of a barrel section associated with the embodiment seen in FIGS. 16–20.

Guide-catch cylinder 340 is best seen in FIG. 20. As seen therein, barrel 20' comprises barrel 70, a substantially closed fore face 342 of barrel 70, distal needle hub 262, providing access to needle 266, and guide-catch cylinder 340. Guide-catch cylinder 340 is medially disposed upon face 342 and extends in elongated fashion in line with of needle 140 (not seen in FIG. 20). Hub 262 is medially disposed inside cylinder 340 along the same line.

Cylinder 340 comprises a plurality of slots which provide relief for outwardly biased members of parts 302 and 304, travel guide for assembly 300 and catch stops which selectively maintain parts of assembly 300 in a proximal position while needle is in use. A first slot 346, disposed to act as a guide, extends the length of cylinder 340. In this embodiment, device 10 is assembled to dispose a portion of wing 330 in slot 346.

Disposed at its distal end, cylinder 340 comprises a second slot 348 offset at 90° from slot 346 and having a length which is adequate for relief from compression of wing 308 when assembly 300 is distally disposed before use. Likewise, cylinder 340 comprises a third slot 350 similar to slot 348 and juxtaposed 180°, therefrom, to provide relief from compression of wing 310. A fourth slot 352 of cylinder 340 is distally disposed 180° from slot 346 and provides before-use relief from compression for wing 328. Should an outwardly biasing material be used in manufacture of assembly 300 which does not take a set after time between assembly and use, it is not necessary to provide slots 348, 350 and 352.

Cylinder 340 provides openings for four slots at its proximal end 353, i.e. slots 346, 354, 356 and 358. As mentioned earlier, slot 346 provides a guide for assembly 300 by containment of wing 300. Longitudinally slots 354 and 356 are respectively aligned with slots 348 and 350. Slot 354 comprises a catching edge 360 for end 318 of wing 308 while slot 356 comprises a catching edge 362 for end 320 of wing 310. Slot 358 is aligned with slot 352 and provides a catching edge 364 for wing 328 as is described in detail hereafter. Each slot has a depth such that in combination latch portions of wings 308, 310 and 328 occur substantially simultaneously.

Latching operation of elements of assembly 300 is best seen in FIGS. 18 and 19. Each of FIGS. 18 and 19 are divided by dashed lines into three sections (A, B and C) to demonstrate operation of fore-part 302 and aft-part 304 of assembly 300 at different positions along the length of cylinder 340. Note that wings 328 and 330 are vertically disposed in FIG. 18. Wings 308 and 310 are vertically oriented in FIG. 19 as parts of assembly 300 in FIG. 19 are rotated by 90° relative to parts in FIG. 18.

It is particularly important to note that wing 328, as seen in FIG. 18A and 18C, extends superiorly from central body part 326 along a line 366 to pivot arcuately upward at arc 368 to join a superior line 370. Further, line 370 ends at a latch point 372. From latch point 372, the shape of wing 328 is further defined by an inwardly progressing line 374 and an acutely connected line 376 which, combination, demarcate jaw 338.

A seen in FIG. 18A, wherein assembly 300 is residing distally within cylinder 340 and tube 80, wing 330 is free to move in the longitudinal direction of needle 140 guided by slot 346. In the same assembly 300 position, wing 328 is disposed in an uncompressed or relaxed state within slot 352. When assembly 300 is pulled proximally to a cocked and useful state as seen in FIG. 18C, assembly 300 passes through an intermediate state seen in FIG. 18B. As assembly 300 is moved proximally from the state seen in FIG. 18A, the form of wing 328 formed along line arcuate line 368 permits wing 328 to be collapsed such that line 370 of wing 328 coincides with the cylindrical inner surface of cylinder 340. In this manner, the aft-part 304 of assembly 300 is facilely allowed to move through cylinder 340.

Note that compression of wing 328 as seen in FIG. 18B causes jaw 338 to compressively pinch tube 140 stopping any flow of liquid therethrough while wing 328 is between slots 352 and 358. Moving assembly 300 proximally to the position seen in FIG. 18C permits wing 328 to be once more relieved as it is biased to enter slot 358. Once there, a latch formed at latch point 372 and along line 374 is caught by edge 364, firmly retaining assembly 300 with tube 140 in a stretched condition.

Referring now to FIG. 19, device 10 has been rotated 90° clockwise relative to a view of the needle 140 end of the device. In FIG. 19 wings 308 and 310 are vertically oriented. Each arm 308, 310 resides in a non-compressed state in slots 348 and 350, respectively. Arm 308 comprises an arcuate surface 378, similar to the wing 328 arcuate surface along line 368, which provides a facile release from slot 348. Arm 310 comprises a similar surface 380 for facile release from slot 350.

As assembly 300 is pulled proximally from the state seen in FIG. 19A to the state seen in FIG. 19B, arms 308 and 310 are compressed inwardly. Each arm 308 and 310 comprises a latching foot, respectively designated 382 and 384, which engages and grips a distal annular surface 386 of central body 326. In this manner, fore-part 302 is releasibly adjoined to aft-part 304 while assembly 300 is pulled forward to a cocked position. In its most proximal position, arms 308 and 310 are outwardly biased into slots 354 and 356, respectively. In this position, feet 382 and 384 catch against edges 360 and 362 to form a permanent latch thereat. Note that outward biasing of arms 308 and 310 release the grasp of feet 382 and 384 against surface 386, thereby releasing the grip of aft-part 304 by fore-part 302.

When the grip of aft-part 304 is so released, needle 140 is relieved of proximal containment in tube 80 when aft-part 304 is triggered to a released state to be distally displaced by contraction of tube 180. Referring once more to FIG. 18C, aft-part 304 is released from a cocked state by depressing area 148 in the direction of arrow 388. Such depression forces wing 328 inward until the part of wing 328 along line 374 and latch point 372 clears edge 364. Contraction of elastic tube 180 retracts aft-part 304 and needle 140, to which the aft-part is securely affixed, into the distal section of tube 80 seen in FIG. 18A. Fore-part 302 remains proximal in tube 80 to effectively plug the hole formed by removal of hub 282 and collar 114. Note that fore-part 302 comprises a threaded hub 132', similar to hub 132.

Reference is now made to FIG. 21 where an exploded view of parts which are comprised in the alternate embodiment seen in FIGS. 16–20. The alternate embodiment parts comprise barrel section 20', tube 180, needle hub assembly 300 and needle containment section 30.

Assembly of the parts seen in FIG. 21 into a complete needle retracting device 10', which is functionally equivalent to device 10, involves the following steps:

1. Affixing tube 180 to hub 332;
2. Biasing wings 308, 310 and 328 inwardly and sliding assembly into cylinder 340 for engagement with slots 348, 350 and 352, respectively;
3. Affixing tube 180 to hub 262. Note that access to hub 262 is provided through slot 346;
4. Laterally displacing section 30 such that the threaded connecting segment 274 of needle cover 120 engages hub 132';
5. Rotating section 30 to affix hub 132' to needle cover 120 (assembly 300 is restrained from rotating because wing 330 is disposed in slot 346 both during assembly and cocking procedures;
6. Affixing section 30 to section 20', preferably by application of adhesives or by ultrasonic welding to form a hermetically sealed package about needle 140.

Figure 22:
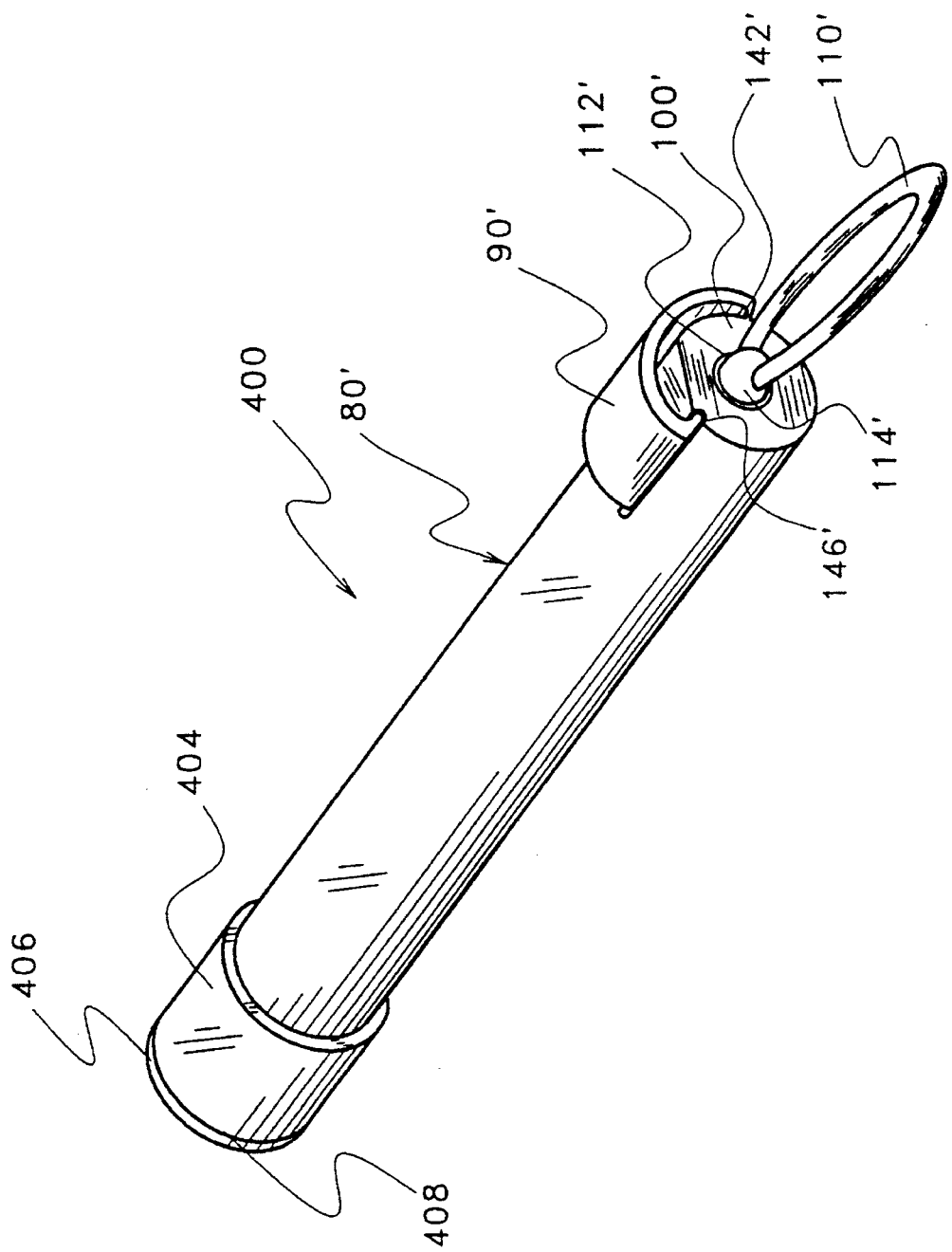
FIG. 22 is perspective of an alternate embodiment of the invention showing a totally enclosed IV catheter insertion assembly.
Figure 23:
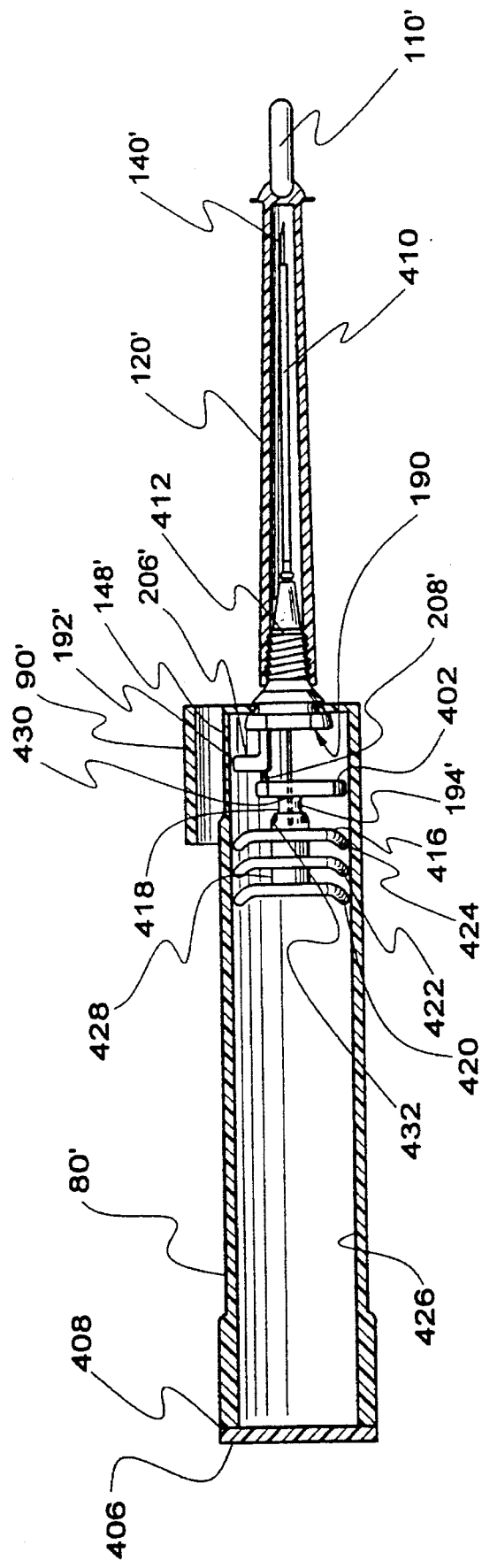
FIG. 23 is a longitudinal section of the assembly seen in FIG. 22.

Reference is now made to FIGS. 22 and 23 where a catheter insertion apparatus 400, another embodiment of the invention, is seen. A closed, transport compatible package of apparatus 400 is seen in FIG. 22. Exteriorly, apparatus 400 is seen to comprise a pull ring 110' affixed to and integral with a front face plate 100', which is similar to face plate 100. Face plate 100' is integral with a tube 80' which is also similar in form and function to tube 80. Face plate 100' also comprises an annular frangible segment 112' which permits ring 110' and a collar portion 114' of plate 100' to be frangibly separated from plate 100' when pulling a needle assembly proximally from tube 80' for use.

Tube 80' comprises a flap 90' which, similar in form and function to flap 90, is releasibly affixed to a groove 146' and on an opposite end attached by a living hinge 142' to tube 80'. Tube 80' is elongated to fully contain a needle 140' used in catheter insertion and a needle draw mechanism 402, as seen in FIG. 23.

At its distal end, tube 80' comprises an annular raised section 404 which acts as a handle during the needle pulling procedure. Further apparatus 400 comprises a distal plate 406 which is securely affixed at the distal end 408 of tube 80' to enclose and hermetically seal needle 140' and withdrawal mechanism 402 inside tube 80'.

Withdrawal mechanism 402 comprises a needle/hub part 160' which is similar to part 160 in form and function. Basic ways in which part 160' departs from the form of part 160 is found at the proximal and distal segments of part 160'. Proximally, part 160' comprises a secondary connection 412 for a transcutaneous catheter 410.

Such catheters and catheter connections are well known in the transcutaneous catheter art. Also needles used with transcutaneous catheters are readily available. A common source is Becton Dickenson Corporation of Franklin Lakes, N. J. 07417-1883. A current source for such catheters is Abbot Hospitals, Inc., North Chicago, Ill. 60064. The material from which tube 80' and plate 406 is made is similar to materials prescribed for tube 80.

Distally part 160' comprises a connection 414 whereby a return energy storing component 416 is affixed to a hub 418 portion of part 160'. As seen in FIG. 23, part 160' comprises catheter needle 140', a fore part 190' proximal to the sharp end of needle 140', a central part 192', and an aft part 194'. With the exceptions of proximal and distal connections of mechanism 402, parts 190', 192' and 194' are substantially the same in form and function to parts 190, 192 and 194. A bridge part 208' and upwardly extending part 206', each being respectively similar in form and function to bridge 208 and part 206, are similarly inwardly disposed for compressible access via a depressible area 148' of tube 80'.

Markedly different, although within the scope of the invention is return energy storing component 416. Component 416 comprises a plurality of piston head parts 420, 422 and 424 which communicate with an inner wall 426 of tube 80' to effectively pull and retain a vacuum as the mechanism is moved proximally. The vacuum contained in tube 80' provides the force which retracts needle 140' when bridge 208' is frangibly broken. To provide an adequate retraction force, parts 420, 422 and 424 must create a differential force of at least four pounds to overcome forces of stiction in both the needle and other retracting mechanisms. For apparatus 400 to have substantially universal use, a minimum atmospheric pressure of ten pounds per square inch is assumed. For a minimum pressure of four pounds realized from an atmospheric pressure of ten pounds per square inch, each part 420, 422 and 424 must have a minimum area of four tenths of a square inch. As parts 420, 422 and 424 are essentially circular planes, their diameter must be a minimum of 0.36 inches (0.9 centimeters).

Parts 420, 422 and 424 are securely affixed to a medially disposed piston hub 428 which is in turn likewise affixed to mechanism 416 via aft part 194'. As indicated by dashed lines 430, needle 140' communicates with hub 428 via part 194. Hub 428 is a hollow vessel which is completely sealed, except for a gas communicating plug 432 disposed proximal from part 424.

Plug 432 is made from a hydrophobic material which is permissive to passage of gas (air), but retards flow of water based liquids (such as blood). The preferred material is Goretex, a material available from W. L. Gore Company, Arizona, USA. Plug 432 is securely affixed hub 428 to provide a pathway for gas to relieve pressure as blood is communicated into hub 428 through needle 140'.

Hub 428 is made from either translucent or transparent materials through which blood may be seen. Thus, by providing the pathway from needle 140' into hub 428 and permitting air to escape from hub 428 as influent blood arrives, hub 428 provides a visually determinable blood "flash" which is commonly used to ascertain entry of needle 140' into a blood vessel.

To use apparatus 400, ring 110' and collar 114' are frangibly separated from plate 100'. Needle cover 120', needle 140' and catheter 410 are pulled from tube 80' until mechanism 402 is firmly attached to plate 100'. By this action a vacuum is created in the portion of tube 80' which is distal to part 420. Cover 120' is removed and needle 140' and catheter 410 are transcutaneously inserted into a patient following good medical practices. When needle 140' enters a blood vessel, blood is communicated to hub 428 through which a blood "flash" communicates to the attending technician that the vessel has been entered. At this point, flap 90' is lifted to provide access to area 148'. A portion of area 148' is depressed to frangibly break bridge 208' which releases the aft portion 194' of mechanism 402 to be retracted by force stored via parts 420, 422 and 424 in cooperation with tube 80'. Needle 140' is thereby withdrawn. Note that the only pathway through blood may be communicated upon withdrawal of needle 140' is into tube 80'. This limitation upon needle withdrawal is a definite advantage over non-self-retracting needle systems currently in use. Under appropriately controlled conditions, catheter 410 is removed for attachment of other medical devices.

Figure 24:
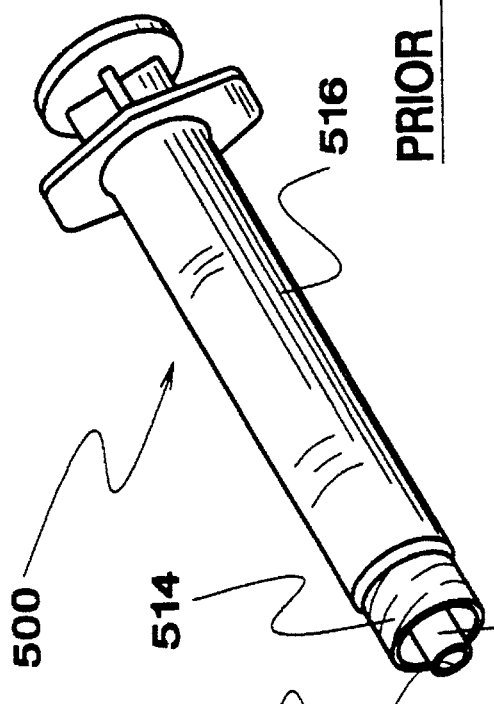
FIG. 24 is a perspective of a 3 cc syringe which is currently commercially available.
Figure 25:
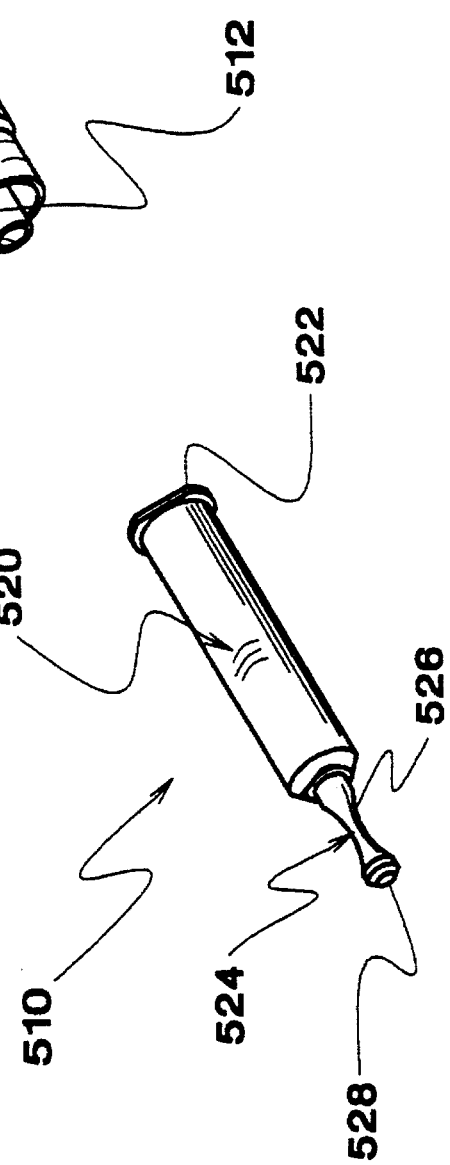
FIG. 25 is a perspective of a retractable medical needle with a back cover removed for ready connection to a medical syringe, such as the syringe seen in FIG. 24.

Reference is now made to FIGS. 24 and 25 wherein a standard commercially available 3 cc syringe 500 is seen in FIG. 24 and a self-retracting medical needle assembly 510 is seen in FIG. 25. Syringe 500 comprises a male luer fitting 512 and a female luer lock connector 514 disposed at an end of an elongated syringe barrel 516. Male fitting 512 comprises a fluid flow lumen 518 wherethrough fluid is communicated between barrel 516 and a medical needle.

Assembly 510 comprises a housing 520, a female luer lock connector 522 and a needle cover 524 extending outward from housing 520 at an end of housing 520 which is distal from luer lock connector 522. Cover 524 comprises a thinned section 526 and an enlarged end 528 which, in combination, provide a section which may be easily grasped between a thumb and forefinger to pull cover 524 from housing 520.

Figure 26A:
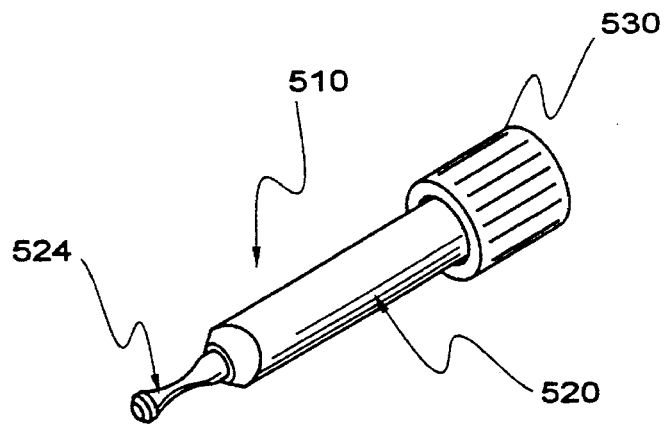
FIGS. 26A–D are perspectives of the retractable medical needle assembly in various stages of use.

Steps involved in using assembly 510 are best seen in FIGS. 26A–D. An "off-the-shelf" embodiment of assembly 510, with an aft portion covered by a cap 530 is seen in FIG. 26A. Cap 530 preferably comprises a male luer lock thread similar to female luer lock connector 514 for secure attachment to luer lock connector 522 of housing 520. In place for transport, cap 530 also is frangibly connected to housing 510, preferably by a connection process known in the plastics molding art as heat staking. Similarly, cover 524 is preferably frangibly connected to housing 520 by heat staking.

Figure 26B:
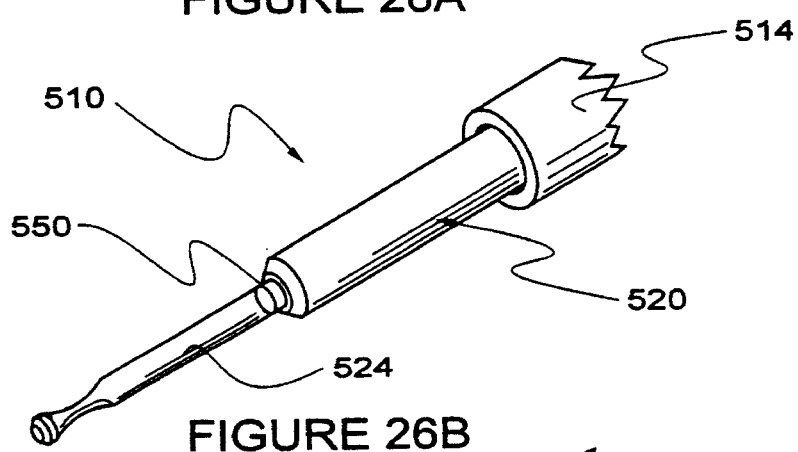

After assembly 510 is connected to a syringe, seen in part by a section of female luer lock connector 514 in FIG. 26B, cover 524 and a medical needle 540 (seen in FIG. 26C) are pulled from housing 510. Cover 524 is preferably frangibly separated from housing 510 to permit cover 524 and needle 540 to be so extended.

Figure 26C:
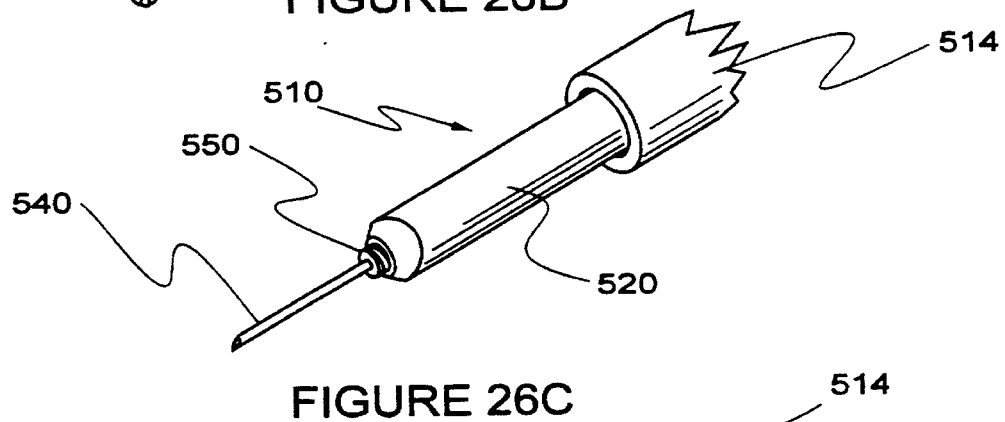
Figure 26D:
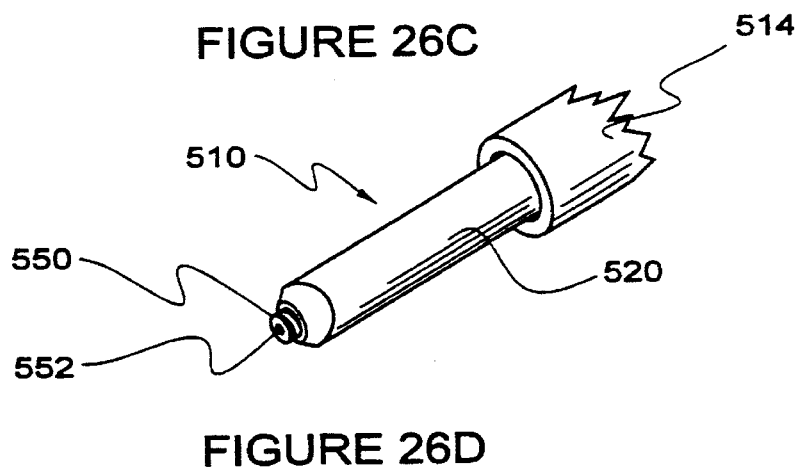

As seen in FIG. 26C, cover 524 is removed (preferably by a quarter-turn twist) to expose medical needle 540. Also exposed is a first hub 550 which rides upon needle 540, but which is slidably free from needle 540 when needle 540 is retracted.

After a medical procedure, medical needle 540 is retracted, by releasing a latch from a catch (disclosed in detail hereafter), back into housing 510. Note that lumen 552, through which needle 540 retractively travels, is the only opening which remains at the fore-end of housing 510 upon needle retraction. Following retraction medical needle 540 is completely and safely contained inside housing 510, permitting simple procedures for safe disposal.

Figure 27:
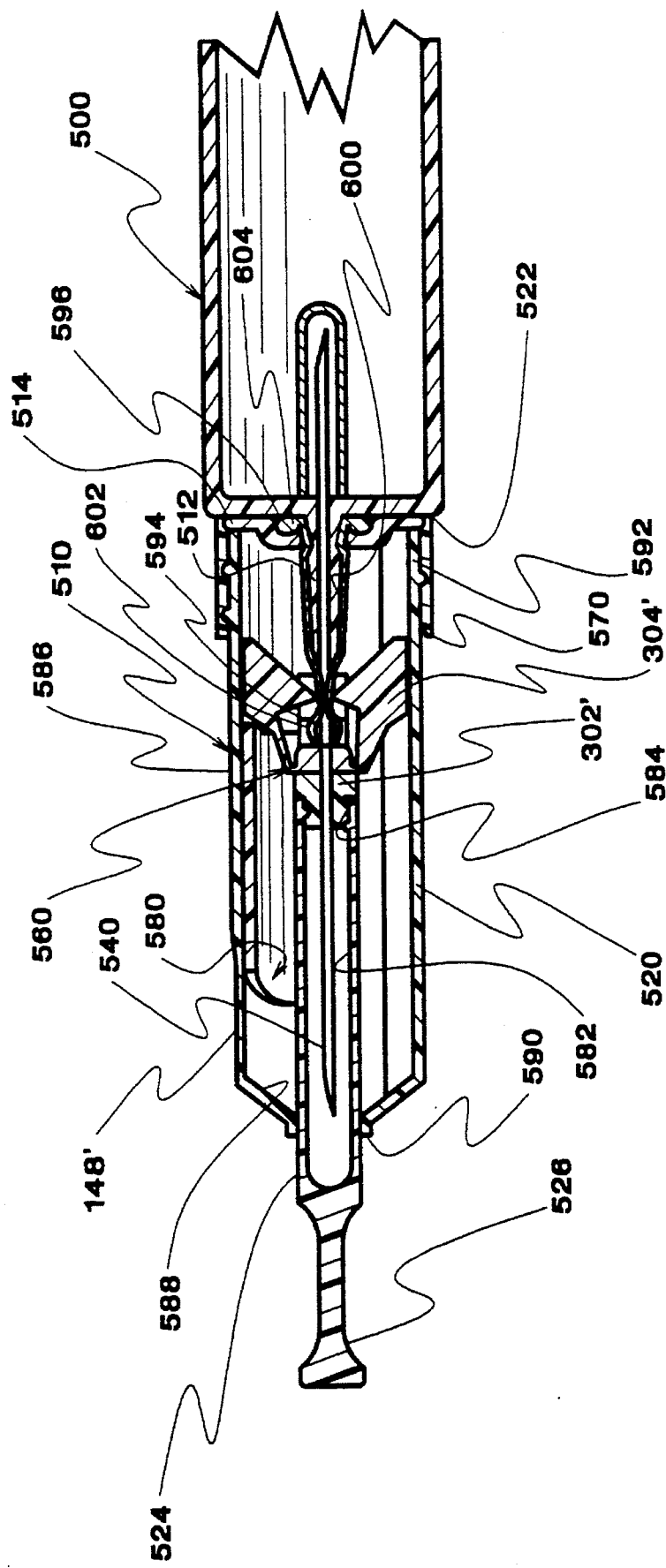
FIG. 27 is a magnified lateral elevation section of the medical needle assembly.

Reference is now made to FIG. 27 in which one embodiment of syringe needle assembly 510 is seen in cross section, greatly magnified. A syringe 500 is affixed to assembly 510 by a female luer lock connector 514. As described earlier, female connector 522 is threaded into luer lock connector 514 to firmly, but releasibly, affix assembly 510 to syringe 500.

In addition to cover 524 and housing 520, assembly 510 comprises a medical needle hub assembly 560, an elastic tube member 570 and an inner housing member 580. As disclosed heretofore, cover 524 comprises a thinned section 526 which provides for facilely gripping cover 524 to pull it and needle 540 from housing 520. Cover 524 also comprises an elongated hollow barrel section 582 in which needle 540 is protectively enclosed prior to use. At an end 584 which is distally disposed from thinned section 526, cover 524 comprises a coupler 584 which releasibly attaches to hub 550. Such attachment is preferably threaded.

Housing 520 comprises an elongated cylindrically shaped barrel 586 and orifice 588 disposed at a needle exit and reentry end 590 of barrel 586. At an end 592, which is distal from end 590, barrel 586 comprises a blunt transverse termination. Disposed near exit and reentry end 590 is a deformable area 148' (similar in form and function to area 148, described heretofore). To accomplish the function of area 148', housing 520, cover 524 and inner housing member 580 are made from a pliable synthetic material, an example of which is polypropylene. Though not seen in FIGS. 25–28, one should understand that a flap similar to flap 90 may be added to housing 520 to protect area 148' from being inadvertently prematurely depressed.

Medical needle hub assembly 560 comprises medical needle 540, a fore hub part 302' and an aft hub part 304'. Hub parts 302' and 304' are similar in form and function to parts 302 and 304, respectively, and are therefore denoted by primes of the earlier named hub parts. Parts 302' and 304' comprise essentially all of the features of parts 302 and 304. The major difference between each part 302 and 304 and 302' and 304', respectively, is size, Parts 302' and 304' are much smaller than respective parts 302 and 304 to permit the size of assembly 510 to be compacted to a diameter which is consistent with the radial diameter of connector 514. Assembly 560 also comprises an elastic tube hub 594 disposed at an end of needle 540 distal from its sharpened end. Similar to parts 302 and 304, parts 302' and 304' are preferably made from resilient, synthetic resinous material.

Rather than using separate parts, such as parts 302' and 304', medical needle hub assembly 560 may comprise a single hub similar to needle/hub part 160 or 160'. In such a case, the hub similar to needle/hub part 160 or 160' is frangibly separated to retract needle 540 into housing 520.

Inner housing member 580 is similar in form and function to cylinder 340 relative to providing forward catches for parts 302' and 304'. Inner housing member 580 comprises catches for wings of parts 302' and 304' and a back plate 596. As may be seen in FIG. 29, back plate 596 comprises an annular groove or recess 598 which forms a catch for a circular lip 604 of elastic tube 570. A catch edge 360', similar to edge 360 which forms a catch of cylinder 340, forms a catch for a wing of part 302'. A similar catch is on the other side of inner housing 580, but is not seen in FIG. 29.

Reference is now made to FIGS. 27–30A–C wherein elastic tube member 570 is seen. Elastic tube member 570 may be made from medical grade latex, silicone rubber or any other elastic tubular material which is reasonably inert and non-injurious to blood. In such materials, elastic tube member 570 may be fabricated by molding, extruding or dipping methods which are well known in the art of elastic part manufacturing.

Figure 28:
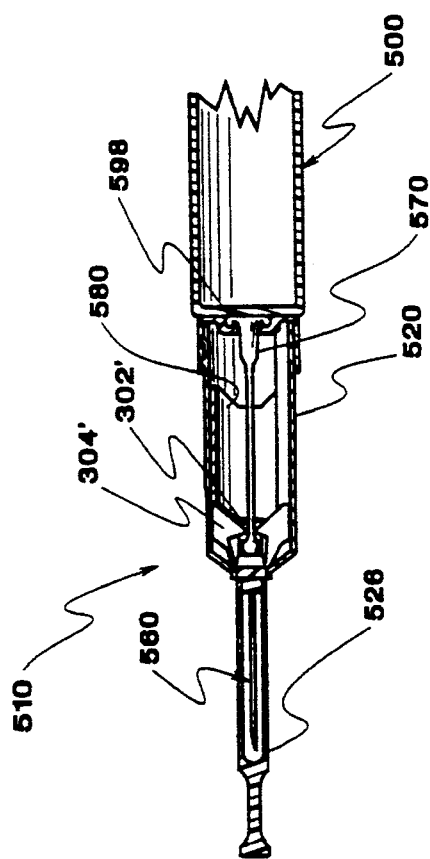
FIG. 28 is a lateral elevation section of the assembly seen in FIG. 27, but somewhat reduced in size and having a medical needle extended for use.

As seen in FIG. 27, tube member 570 comprises an internal surface 600 which conformably but relatively loosely fits over male luer fitting 512. It is preferable for fitting 512 to somewhat loosely fit surface 600 to permit space for fluid to be withdrawn inward through needle 540 when needle retraction takes place. However, it should be specially noted that surface 600 should be constricted to tightly seal about fitting 512 when needle 540 is extended outwardly from housing 520, as seen in FIG. 28. This constriction assures a tight seal between tube 570 and fitting 512 when assembly 510 is in use. Pulling of medical needle hub assembly 560 outward from housing 520 which results in stretching of tube 570 about fitting 512 to form the seal is best seen in FIG. 28.

On an end proximal to needle 540, tube 570 comprises an inner surface 602 which is sized to snugly fit over tube hub 594. From a simplicity of manufacturing point of view, it is preferred to provide a fit which causes tube 570 to adhere to hub 594 without adhesive. However, it is within the scope of the invention to adhesively secure tube 570 to hub 594 to assure total connection reliability. On the end of tube 570 proximal to surface 600, tube 570 comprises annular lip 604, best seen in FIGS. 30A–C.

Figure 30A:
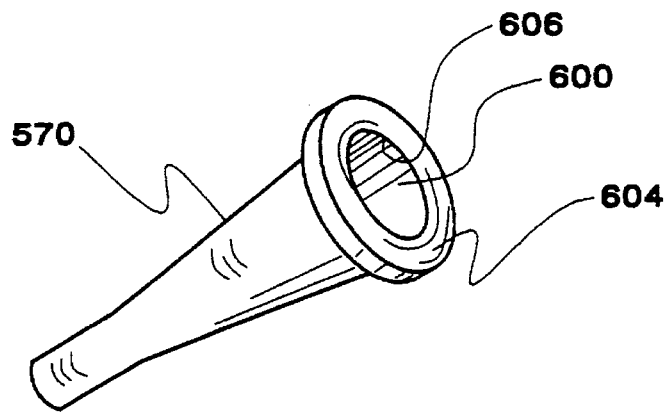
FIGS. 30A–C are perspectives of molded elastic tube parts.
Figure 30B:
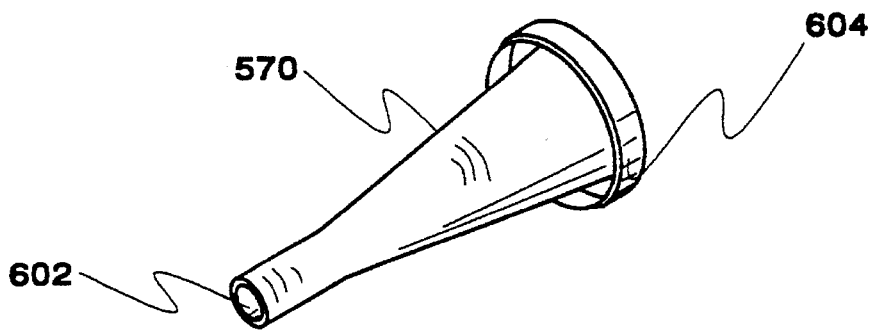
Figure 30C:
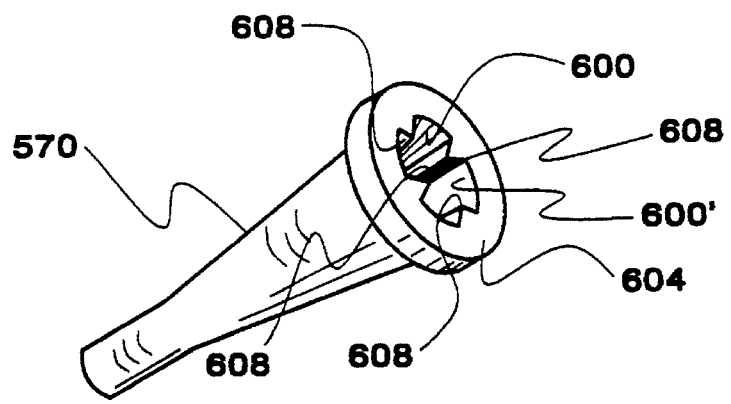

As seen in FIGS. 30A–C, tube 570 comprises a generally frustoconical shape which is somewhat elongated into the region of inner surface 602. While a frustoconical shape is preferred, a long tubular shape of substantially constant radius may be used. However if tube 570 is made by dipping or molding, added features which may be incorporated thereby include an O-ring shape 606, seen in FIG. 30A, disposed as an internally directed raised feature which acts to closely engage a fitting 512 and thereby to wipe fitting 512 clean when it is disengaged from tube 570. Also a series of ribs 608, seen in FIG. 30C disposed along inner surface 600 causes a space to be eliminated when tube 570 is stretched and to be recreated when tube 570 is allowed to compress to a resting state while retracting needle 540. The added space creates a negative pressure which draws fluid inward from needle 540 as it is retracted to minimize fluid regurgitation upon needle retraction.

Lip 604 comprises an annular hook which holds tube 570 in place in groove 598 when fitting 512 is inserted into assembly 510. Preferably, lip 604 is adhesively secured to backplate 596 to permit fitting 512 to be disconnected and withdrawn without disassembling tube 570 from backplate 596.

Figure 29:
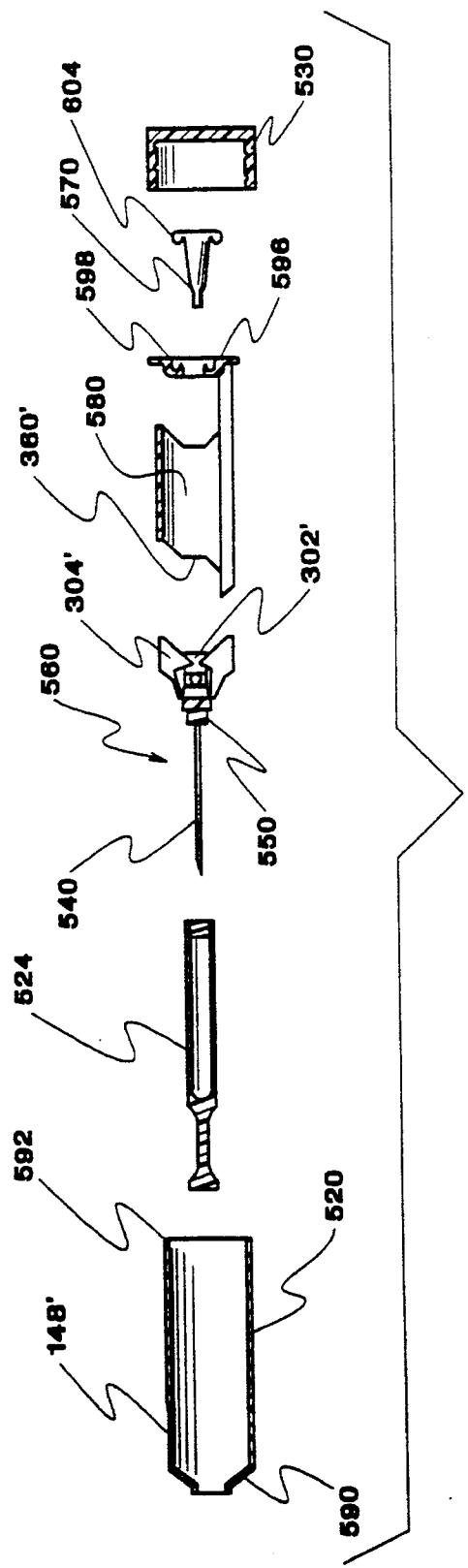
FIG. 29 is an exploded view of the retractable medical needle assembly.

As seen in FIG. 29, assembly 510 is directly adaptable to automatic construction. Housing 520, cover 524, parts 302' and 304', inner housing 580 and cap 530 are all preferably injection molded parts. Tube 570 is preferably mass produced by extrusion, dipping or molding. Needle 540 is preferably made from medical needle grade steel and sharpened to a needle point by methods currently well known in the medical needle art.

Assembly 510 is designed to be automatically assembled. First parts 302' and 304' are slidably affixed to needle 540 by inserting needle 540 through axial holes in each of parts 302' and 304'. Part 304' is best securely affixed to needle 540 by an adhesive (preferably epoxy). Cover 534 is releasibly affixed to hub 550. Tube 570 is disposed through backplate 596 and lip 604 is preferably adhesively affixed to groove 598. Inner surface 602 is disposed about hub 594 and, if necessary to assure secure affixation, bonded to thereto. Housing 520 is disposed about inner housing 580 and cover 524 such that thinned section 526 is disposed outside exit and reentry end 590. One wing of part 304' is aligned with distortable area 148'. Housing 520 blunt end 592 is juxtaposed against backplate 596 and securely affixed thereat, preferably by ultrasonic bonding. Cap 530 is releasibly affixed to backplate 596 by a threaded connection. To provide proof of tampering, cap 530 is preferably heat staked to housing 520 and housing 520 is heat staked to cover 524.

Figure 31:
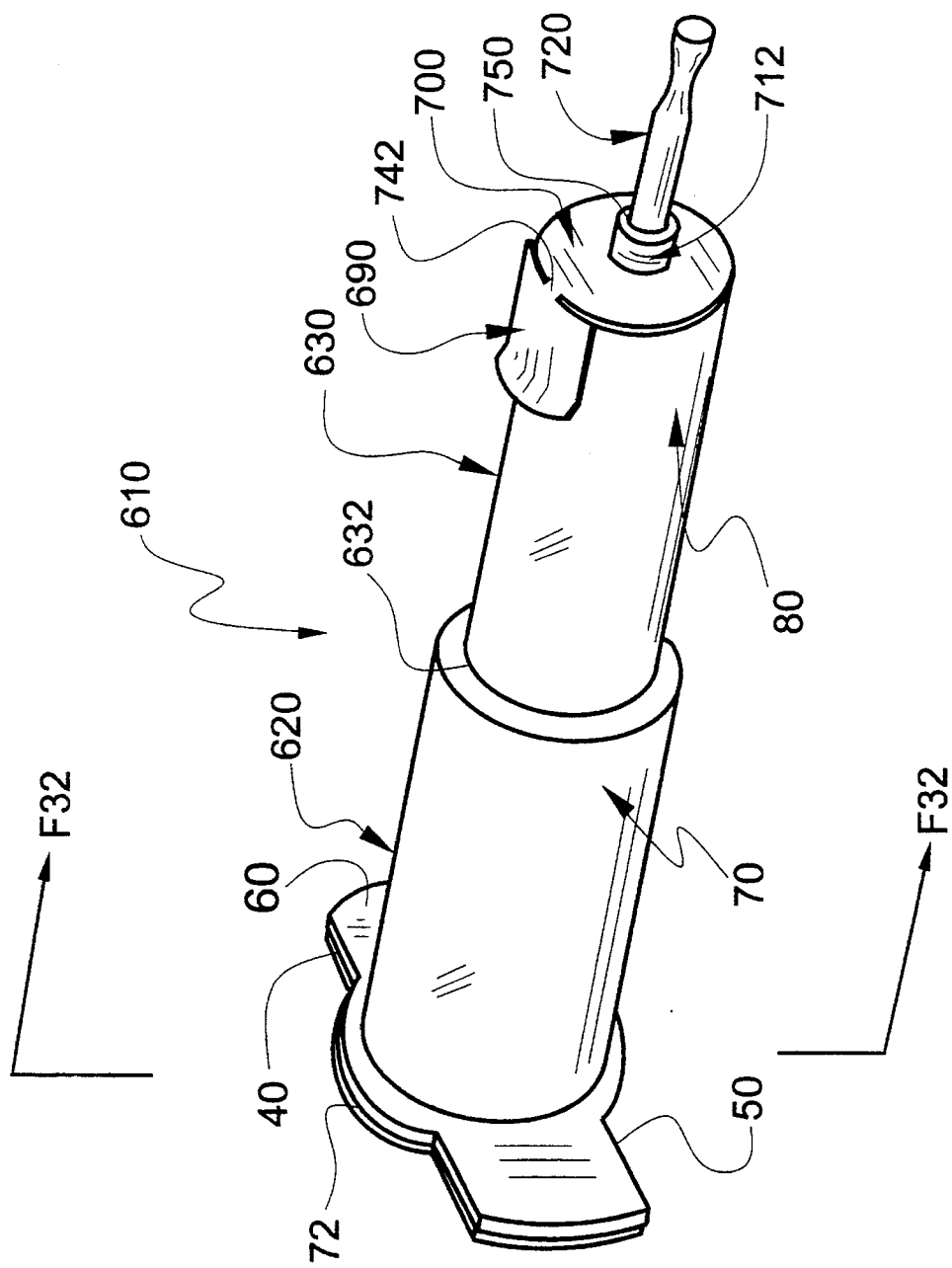
FIG. 31 is a perspective of a another blood draw device, showing the exterior of the device housing.
Figure 32:
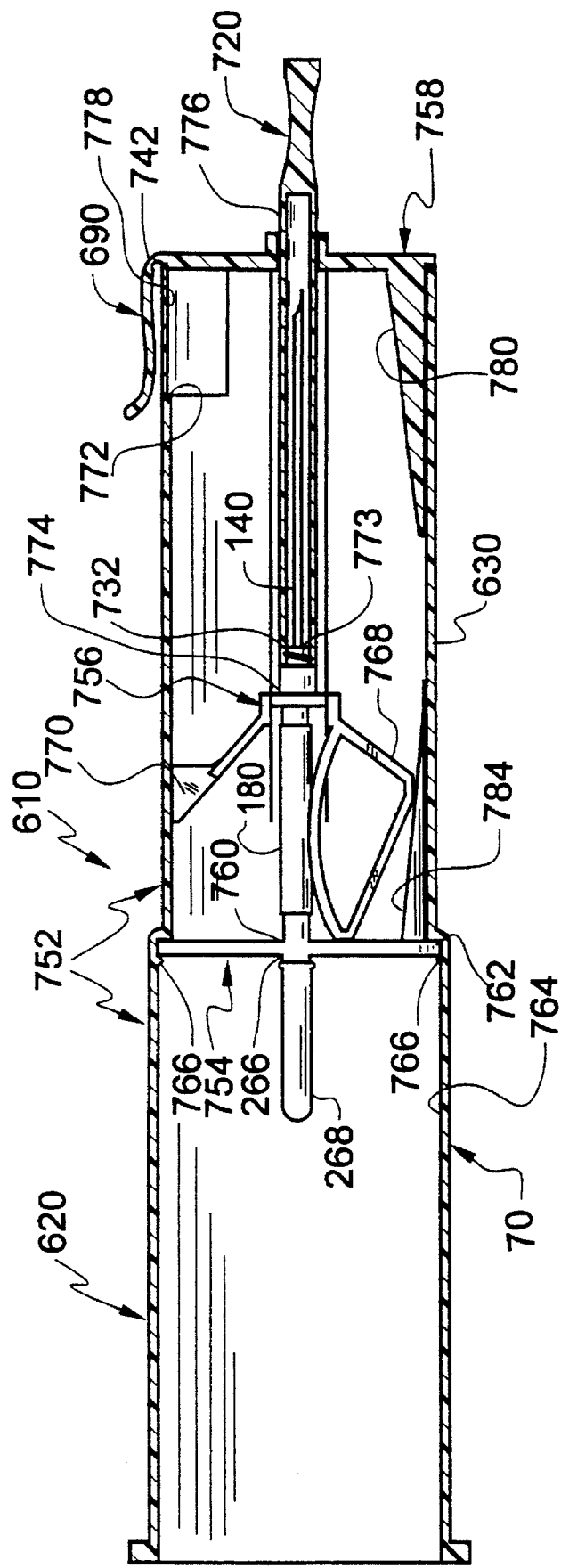
FIG. 32 is a cross section along lines F32/F32 (see FIG. 31) of the blood draw device seen in FIG. 31.
Figures 33, 33A:
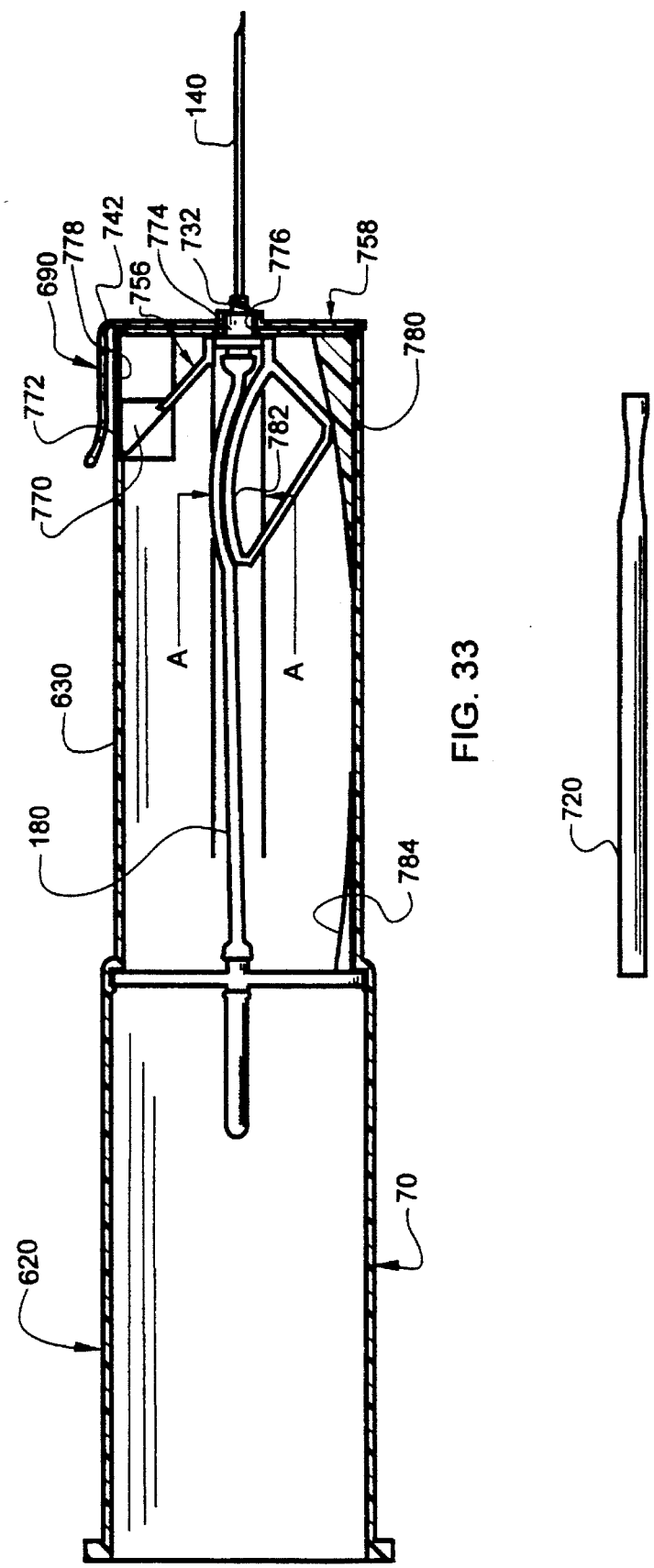
FIG. 33 is a cross section of the blood draw device of FIG. 31 in a cocked state and ready for use in a medical procedure.
FIG. 33A is a side elevation of a needle cover which has been removed in FIG. 33.

Another embodiment of the invention is seen in FIG. 31. The embodiment of FIG. 31 comprises a device 610 which is similar in form and function to device 10 seen in FIGS. 1–4. As seen in FIG. 31, device 610 comprises a barrel section 620 and a needle containment section 630. In a completely assembled device, section 620 is securely affixed to section 630 along circular line 632 to provide protection for contents of the device from environmental damage and contamination. As seen in FIGS. 32 and 33, barrel section 620 and needle containment section 630 may be preferably molded as a single part to reduce the number of molded parts.

Barrel section 620 comprises a planar seal 40 and a pair of left and right ear or handle parts, designated 50 and 60, respectively, and a hollow barrel 70. Planar seal 40 is preferably adhesively attached to barrel section 620 within a plane area defined by continuous line 72 such that the hollow of barrel 70 is maintained in a sterile condition prior to use. To use device 610, seal 40 is manually removed. Of course, a different kind of seal may be used, such as a snap-on part which may be molded as a tether-attached part of section 620. The snap-on part is not shown in FIG. 31, but production of such parts is well known in the art. A more detailed description of the internal parts of barrel 70 is provided hereafter.

Needle containment section 630 comprises an elongated tube 680, a flap 690, a proximally facing front face plate 700 and a needle cover 720 partly externally disposed prior to use. Importantly, it should be noted that needle cover 720 is separable from front face plate 700 by means of a frangibly detachable cylindrical segment 712 of needle containment section 630, which is described in more detail hereafter.

Steps related to the use of device 610 are similar to those disclosed for device 10 in FIGS. 2–4. However, needle cover 720 is preferable attached to cylindrical segment 712 by heat staking. Therefore, needle cover 720 is detached by breaking the heat stake and pulling needle cover 720 and its associated medical needle, generally numbered 140, outward from needle containment section 630. Once needle cover 720 and medical needle 140 are fully extended, a latch is caught upon a latch retain needle cover 720 and medical needle 140 in position just prior to use. Structure of the catch, latch and workings of other parts disposed within needle containment section 630 are disclosed in more detail later.

As in device 10, seal 40 is removed from barrel section 620. In a next step, needle cover 720 is removed from device 610. Needle cover 720 is preferably attached to a hub 732 by a rotatably detachable coupler, such as by a threaded or bayonet type connector. In any event, the coupling attachment between hub 732 and cover 720 must be able to support a pull force at least as great as a retarding force imposed in the opposite direction by a retracting mechanism which is energized by the pull extending cover 720 until engagement of the aforementioned catch and latch. As seen in FIG. 33, hollow medical needle 140 is bared upon removal of cover 720.

Similar to flap 90, flap 690 comprises a living hinge attachment 742 to needle containment section 630. Different from flap 90, flap 690 does not comprise a hook latch normally engaged in a groove, but is preferably molded to lie in a biased position upon tube 80. However, flap 690, like flap 90, is facilely lifted from its biased position to permit access to a distortable section disposed under and protected by flap 690. Thus, during a medical blood draw procedure, flap 690 is protectively disposed. Once blood acquisition has been completed, flap 690 is lifted by action of a single digit after which needle 140 may be retracted by depressing an area 748 which is made and positioned to act in the same fashion as area 148. Retraction places needle 140 safely inside tube 80. Only access inside tube 80 and needle 140 is a hole 750 through which needle cover 720 was drawn to expose needle 140. Retraction mechanisms for device 610 are generally the same as those disclosed for device 10. However, there are differences in internal mechanisms of the two devices which are described in detail hereafter.

Attention is now drawn to FIG. 32 wherein device 610 is seen to comprise a reduced number of parts compared to the number of parts shown for the device seen in FIGS. 16–21. Device 610 comprises a cylindrical part 752 which is molded as a single part and comprises the cylindrical portions of needle containment section 630 and barrel section 620. Further, device 610 comprises a rear assembly plate 754 which is similar in form and function to assembly plate 264, except that there is no part which is equivalent to key 260 on plate 754. Device 610 also comprises a single hub 756, and elastic tube 180 and a front plate 758.

Similar to assembly plate 264, assembly plate 754 comprises a snubber 268 and rear needle 266 for piercing a vacuum blood collection tube. Proximal to elastic tube 180, assembly plate 754 comprises a hub connection 760 for connecting plate 754 to tube 180. Circumferentially, plate 754 comprises an outside edge 762 which is sized to compressibly fit inside the inner wall 764 of barrel part 620. Preferably, inner wall 764 also comprises a plurality of raised beads or a raised inner ring 766 into which outside edge 762 is "snapped" for firm retention. However, outside edge 762 may be held in place by adhesive bonding or ultrasonic welding, all of which are well known in the art of joining one plastic part to another.

Hub 756 is used to interconnect a medical needle 140 to tube 180 and to provide a tube distorting part 768 and a wing latch 770 which is disposed to attach to a catch 772 when needle 140 is extended for use. Further hub 756 comprises a threaded portion 773 which is proximal to the sharp end of the needle and used to firmly but releasibly connect to needle cover 720. Disposed distal from hub 732 is a cylindrical shoulder 774 which fills a cylindrical orifice 776 in front plate 758 through which needle cap 720 and needle 140 are pulled for use of needle 140. Shoulder 774 should be sized to fit snugly into orifice 776 to provide axial support for needle 140.

In this manner, the orifice through which needle 140 is retracted to safe containment within tube 80 is orifice 776. For this reason, orifice 776 should be made sufficiently small that no access is provided to human limbs or other parts. Note that device 610 contains only five parts which are preferably made by injection molding. They are needle cap 720, cylindrical part 752, plate 754, hub 756 and front plate 758. The single hub 756 provides the opportunity for this limited number of parts. It may at first appear that fewer parts may be used in construction of device 610 by combining one or more of the five parts. However, based upon current molding and assembly considerations related to cost of the device, this parts breakdown is currently considered best for this embodiment.

The reader is now invited to turn attention to hub 756. Similar to parts 302 and 302', hub 756 comprises wing latch 770 which is designed to catch at catch 772. As previously described for earlier embodiments, cylindrical part 752 comprises a distortable section 778, distortion of which releases latch 770 from catch 772 to permit elastic contraction of tube 180 to retract needle 140 into needle containment section 630.

Figure 33B:
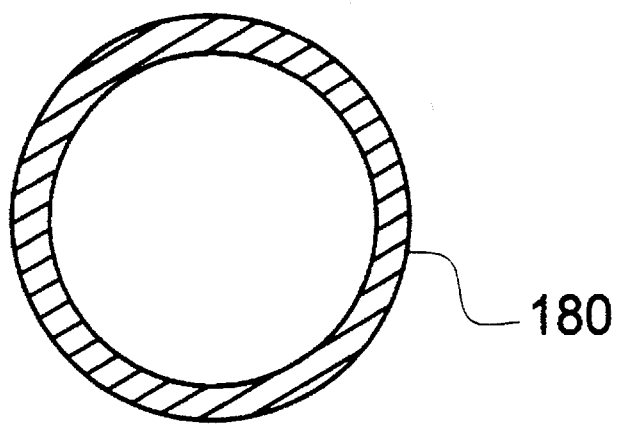
FIG. 33B is a cross section of a stretched elastic tube.
Figure 33C:
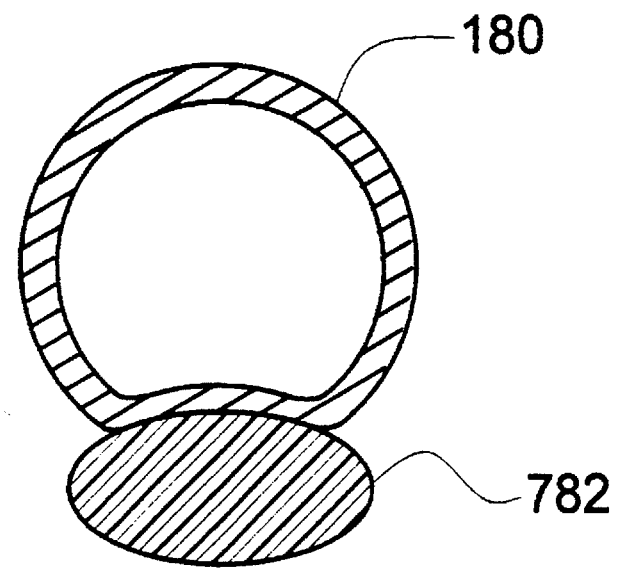
FIG. 33C is a cross section of the stretched elastic tube seen in FIG. 33B but being distorted by a plastic section from the more circular geometry seen in FIG. 33B.
Figure 34:
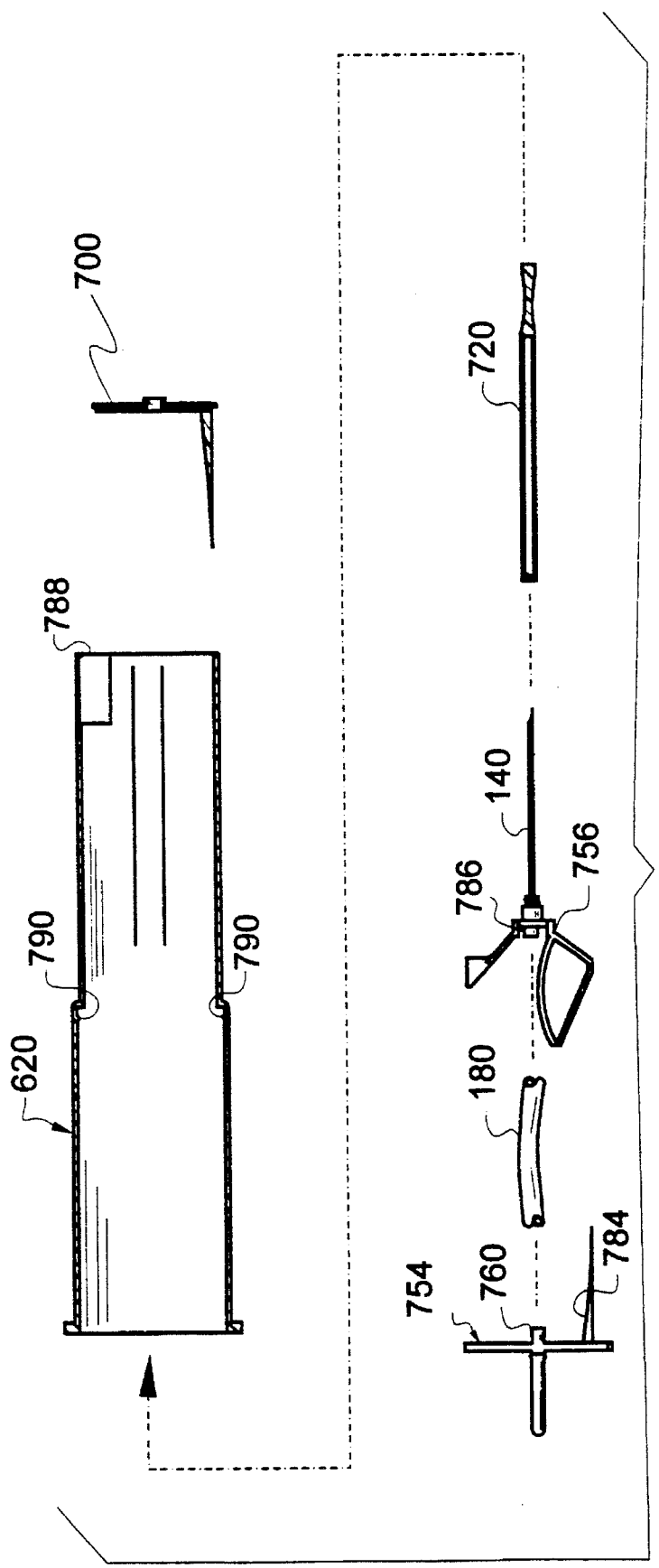
FIG. 34 is an exploded view of parts seen in FIGS. 32 and 33.

Hub 756 also comprises tube distorting part 768 which is key to providing control of regurgitant fluid without requiring a check valve. Note that when hub 756 is pulled forward in needle containment section 630, a sloped ramp part 780, preferably molded as part of front plate 758, causes a raised segment 782 of tube distorting part 768 to engage and distort a section of tube 180. Reference is made to FIG. 33B wherein a non-distorted tube is seen to have a substantially circular cross section. However, in a region or section of tube 180 which is so distorted by part 768 (segment 782), as seen in FIG. 33C, the circular cross section is flattened on one side to reduce the internal cross sectional area of tube 180. This flattening produces a reduced volume of tube 180 in the section so affected.

To understand the need for such a reduction when needle 140 is extended and device 610 is cocked for needle retraction, one must understand the general dynamics of changes in internal tube volume as a tube is stretched between two hubs to which the tube is attached. Generally, if fluid is captured as a contiguous fluid bolus between, but not in contact with, connecting hubs, and a mark is placed at each end of the bolus, as the tube is stretched, the ends of the fluid bolus remain substantially at the marks. However, if fluid inside the tube is increased to reside within connecting hubs as well, the volume for containment of fluid inside the tube between the hubs increases primarily due to connecting end effects at the hubs.

Such an increase in volume inside tube 180 in a stretched condition relative to volume inside tube 180 in a relaxed condition causes an excess of contained fluid which is regurgitated or pumped from tube 180, usually through needle 140, when needle 140 is retracted as tube 180 is permitted to contract. It has been found through experimental study that hub size is an important factor in controlling the amount of volume increase, but complete control cannot be achieved by hub design alone. Therefore a distortion of tube 180, when in a stretched condition, provides a significant method for reducing the internal volume of stretched tube 180 to be less than the relaxed volume of tube 180.

Fluid dynamics associated with braking a rapidly retracting needle (and tube) also may contribute to fluid regurgitation. For this reason, it is recommended that final retracting velocity be maintained within as low a velocity as possible. It is for this purpose that a posteriorly disposed ramp 784 provides a frictional contact between tube 180 and part 768 at the end of needle retraction travel. In this embodiment, it is preferred that ramp 784 be molded as a part of plate 754. While this method of fluid control is seen to be applied to the embodiment seen in FIGS. 31–33C, one who is skilled in the art of retracting systems and fluid control would understand that this method or other methods disclosed hereafter may be applied to other needle retracting embodiments disclosed herein.

Use of device 610 is similar in functional steps to devices heretofore described. Needle 140 and needle cap 720 are extended from the rest of device 610 as seen in FIG. 33, with needle cap removed as portrayed in FIG. 33A. The needle is used in a medical procedure after which protecting flap (shroud) 690 is raised, preferably by a finger or thumb, to provide access to distortable section 778. Section 778 is distorted to cause latch 770 to become disengaged from catch 772. The freed hub 756, needle 140, and contracting tube 180 are then fully retracted into needle containment section 630 for safe retraction and storage of needle 140.

Of course, for device 610 to compete with current needle devices, assembly should be simple to automate. The simple, linear assembly procedure for device 610 is shown schematically in FIG. 34. Needle 140 is securely affixed to hub 756 (preferably by epoxy), and cover 720 is securely, but releasibly affixed to hub 756 to protect needle 140. Tube 180 is affixed to tube attachment connecting hubs 760 and 786. Methods for securely attaching tube 180 are well known in the current state-of-the-art of connecting elastic tubes to plastic hubs and range from use of connection by physical hub design alone to the use of adhesives and solvents. Once a tube 180 material and a hub 756 and back plate has been selected, the type of appropriate connecting method can be determined by then current standard materials and procedures.

So attached, needle 140 and other joined parts are introduced into barrel part 620 until needle cover 720 is exposed at proximal end 788. To complete assembly of device 610, orifice 776 of front plate 758 is fitted over needle cover 720 and firmly affixed to part 620, preferably by heat staking, although other connecting techniques such as mechanical interconnects and adhesive bonding may be used. Also, it is preferred to either mechanically affix back plate 754 in place (such as by an internally disposed containment ring 790 as seen in barrel part 620) or by heat staking or ultrasonic welding.

Figure 35:
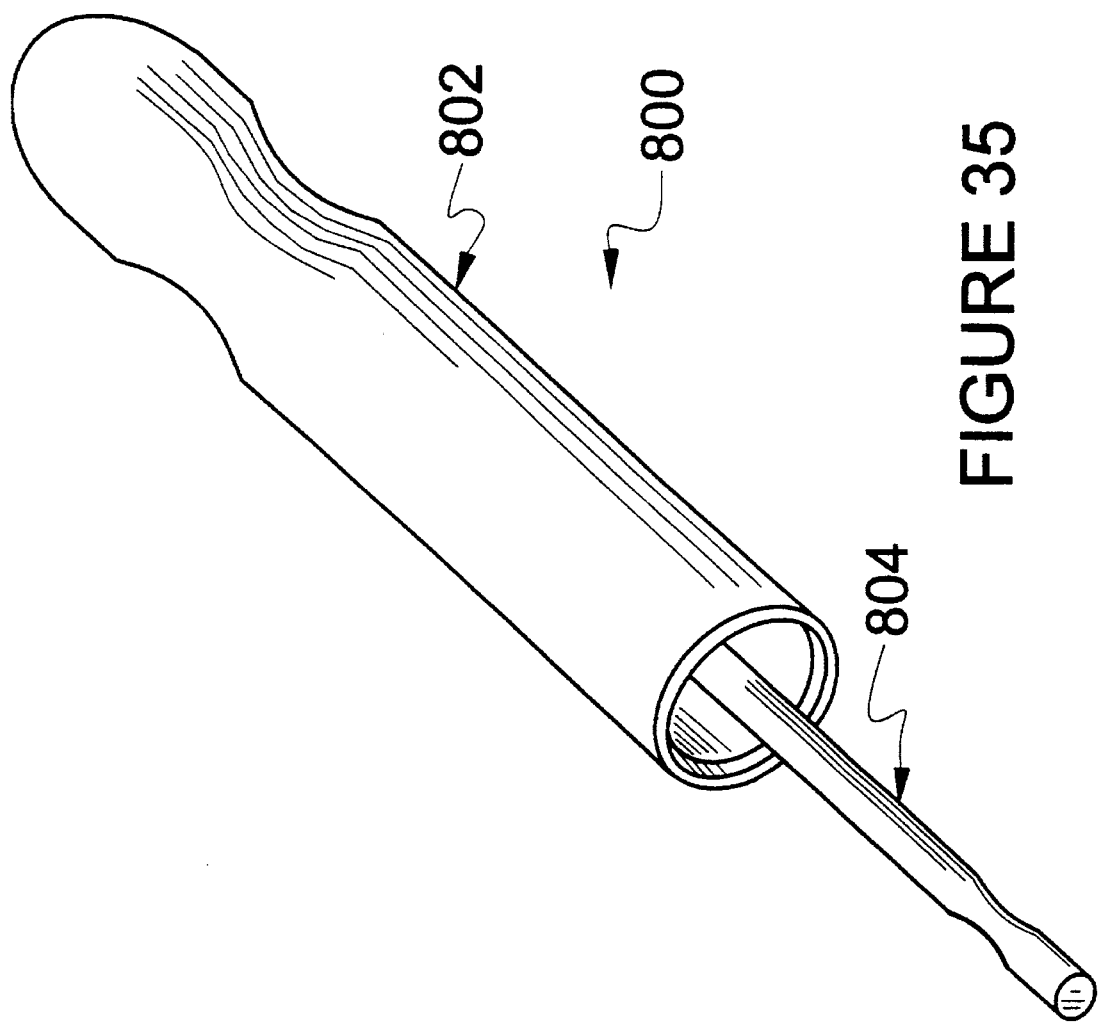
FIG. 35 is a perspective of a needle withdrawal device which is cocked by extending a slidable exterior cover away from a needle cover.
Figure 36:
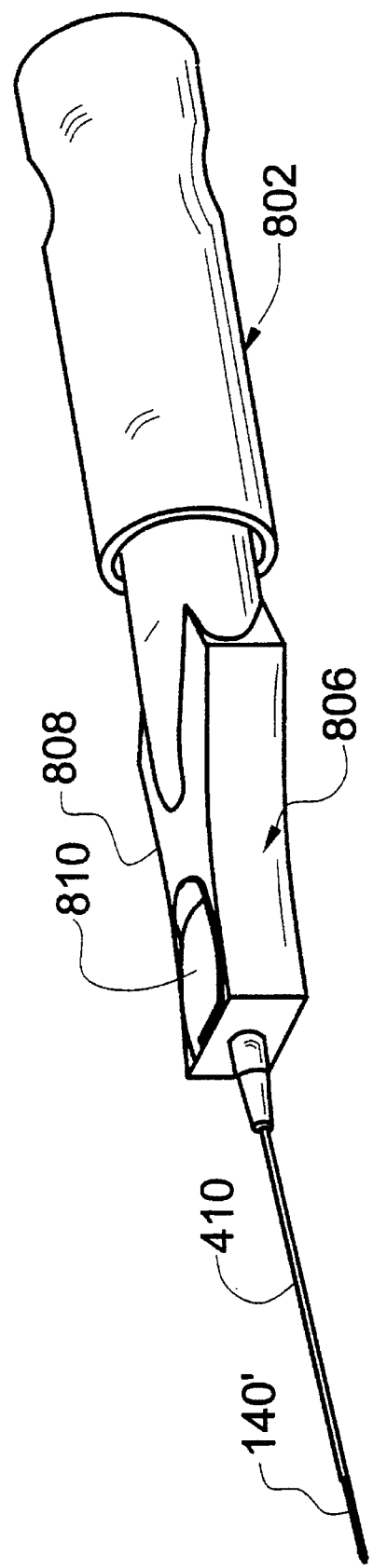
FIG. 36 is a perspective of a catheter version of the needle withdrawal device seen in FIG. 35, with the slidable exterior cover disposed away from a medical needle to thereby cock the device for automatic needle retraction.
Figure 37:
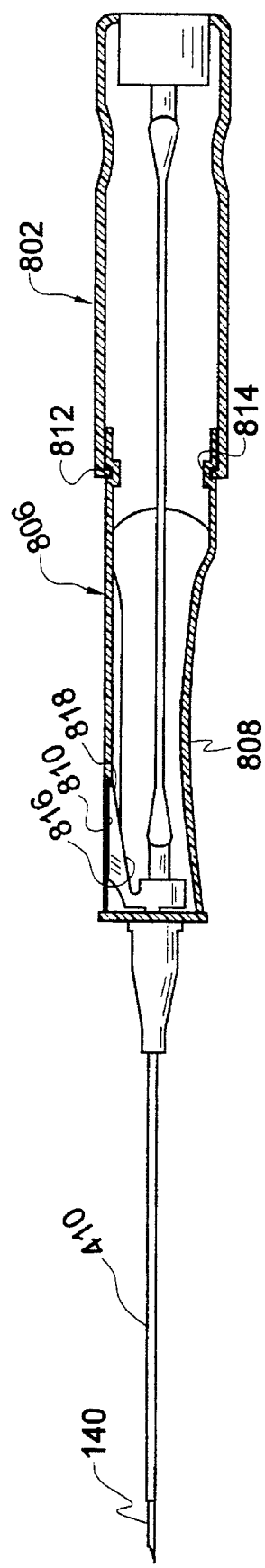
FIG. 37 is a cross section of the catheter version seen in FIG. 36.

Another embodiment of the invention which employs a permanent catch and a separate latch release mechanism is seen in FIGS. 35–37. This construction is best applied to needle retraction devices more closely related to catheter and syringe embodiments due to assembly constraints of embodiments having large posterior parts, such as the barrel part of a blood draw device.

The embodiment of FIGS. 35–37 is seen in FIG. 35 to be a device 800 which comprises a rearwardly extendable cover section 802 and a forwardly extendable needle cover 804. As seen in FIG. 36, cover section 802 is extended rearwardly relative to needle 140' (as an example, a catheter needle and catheter configuration) to permit needle 140' to be exposed for use.

As seen in FIG. 36, in addition to cover section 802 and needle cover 804, device 800 comprises a preformed insertion handle section 806 and a catheter 410. Section 806 comprises a thinned section 808, which provides facile gripping for catheter insertion, and a distortable section 810 by which a latch and catch release is made to retract needle 140'.

In cross section, in FIG. 37, section 806 is seen to comprise an annular catch 812 to permanently anchor a corresponding annular latch 814 of cover section 802. In this embodiment, a hub latch 816 is secured against catch 818 when manufactured. Tube 180 is stretched to provide retractive force by rearward extension of section 802. To retract needle 140' to safe containment inside the combined internal volumes of sections 802 and 806, distortable section 810 is compressed to release latch 816 from catch 818.

Reference is now made to FIGS. 38–42, wherein another apparatus and method for constraining internal volume of a stretched tube 180 relative to a relaxed tube 180 is seen. In this embodiment a device 820 is seen in cross section. In most ways device 820 is similar in form and function to device 610. Major differences comprise elimination of ramps 780 and 784 in device 820. In the place of ramp 780, a tapered cylindrical section 822 is used in place of section 630 to perform the ramping function of ramp 780. The other major difference is the form and function of a forward hub 824. Note that hub 824 is the only hub surrounding needle 140.

Hub 824 comprises a segment 826 to which a needle cover 720', like needle cover 720, is attached for the purpose of protecting needle 140 and pulling needle 140 and hub 824 to extend needle 140 for use in a medical procedure. Similar to section 630, device 820 comprises a catch 828 and an associated latch 830 which engage to retain hub 824 and needle 140 in an extended state. Release of latch 830 from catch 828 is preferably caused by distortion of a distortable portion 832 of tapered cylindrical section 822.

Distal to segment 826, hub 824 comprises a pair of wing parts 834 and 836 which form a clamp about tube 180 when hub 824 is moved forward to extend needle 140 for use. As seen in FIGS. 41 and 42, each wing part 834 and 836 comprises a U-shaped clamping surface 838 and 840, respectively. When tube 140 is in a relaxed position, the clamping surfaces 838 and 840 do not distort the otherwise circular cross section of interposed tube 180. However, when tube 180 is stretched by extension of needle 140, the taper of cylindrical section 822 causes wing parts 834 and 836 to clamp about tube 180. The distortion reduces the cross section and therefore the internal volume of stretched tube 180, thereby causing tube 180 to have a smaller internal volume when stretched than when relaxed. Such a condition substantially eliminates any opportunity for fluid regurgitation when needle 140 is retracted. Other apparatus and methods may be used within the scope of the invention to reduce the volume of a stretched tube 180 to be less than a relaxed tube 180. An example of another method is disclosed hereafter.

The opening between clamping surfaces 838 and 840, when needle 140 is extended, determines the amount of flattening of tube 180 and, thus, the amount of volumetric reduction therefrom. An exemplary calculation showing amount of volumetric reduction which may be achieved is provided as follows:

If D is the internal diameter of an unstretched tube, and d is the internal diameter of a tube stretched to three times its normal length, then it is well known in the art that $D^2$ is approximately equal to three times $d^2$. If, in a stretched and flattened tube, the internal height of the tube may be represented by h, as seen in FIG. 42. Note that the circumference (C) of the stretched tube is $\pi$ times d. The area of the stretched tube is $\pi$ times $d^2/4$. However, the cross sectional area (A) of a flattened portion of the stretched tube is given by:

$$A = \pi h^2/4 + (C - \pi h)h/2 \qquad \text{Eq. 1}$$

For a case where h=0.46 mm and d is 0.92 mm, A equals 0.50 mm$^2$. The cross sectional area of a stretched, but unflattened tube is 0.66 mm$^2$, providing a reduction in area of 0.16 mm$^2$ or a volume reduction of about 0.16 mm$^3$ for each mm the tube is clamped. If the tube is clamped ¾ inch or 19 mm, the exemplary reduction is about 3.0 mm$^3$.

Figure 38:
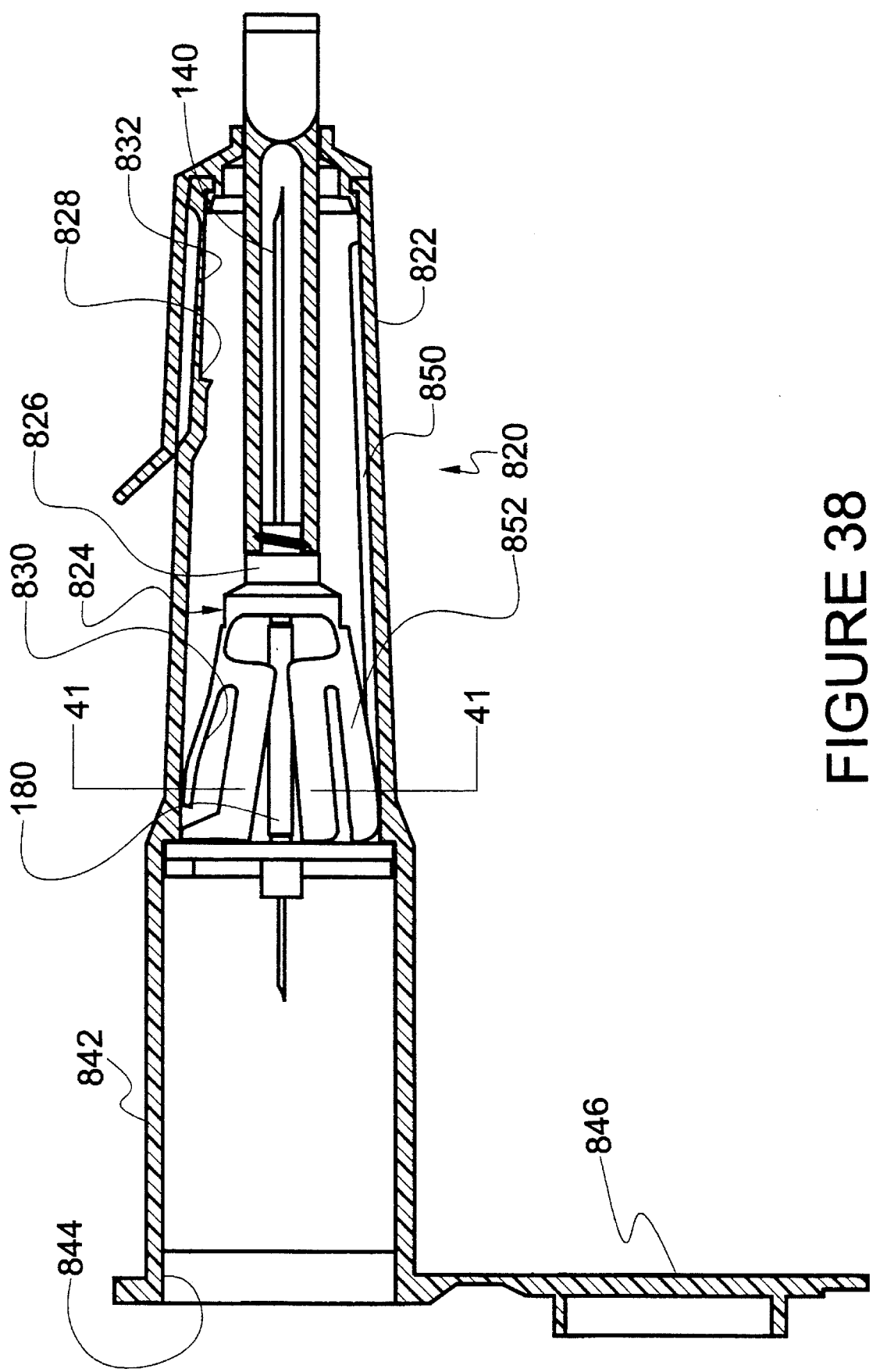
FIG. 38 is cross section of a needle withdrawal device disposed in a rest or needle transportation state and having another embodiment of an elastic tube distortion apparatus.
Figures 39, 40:
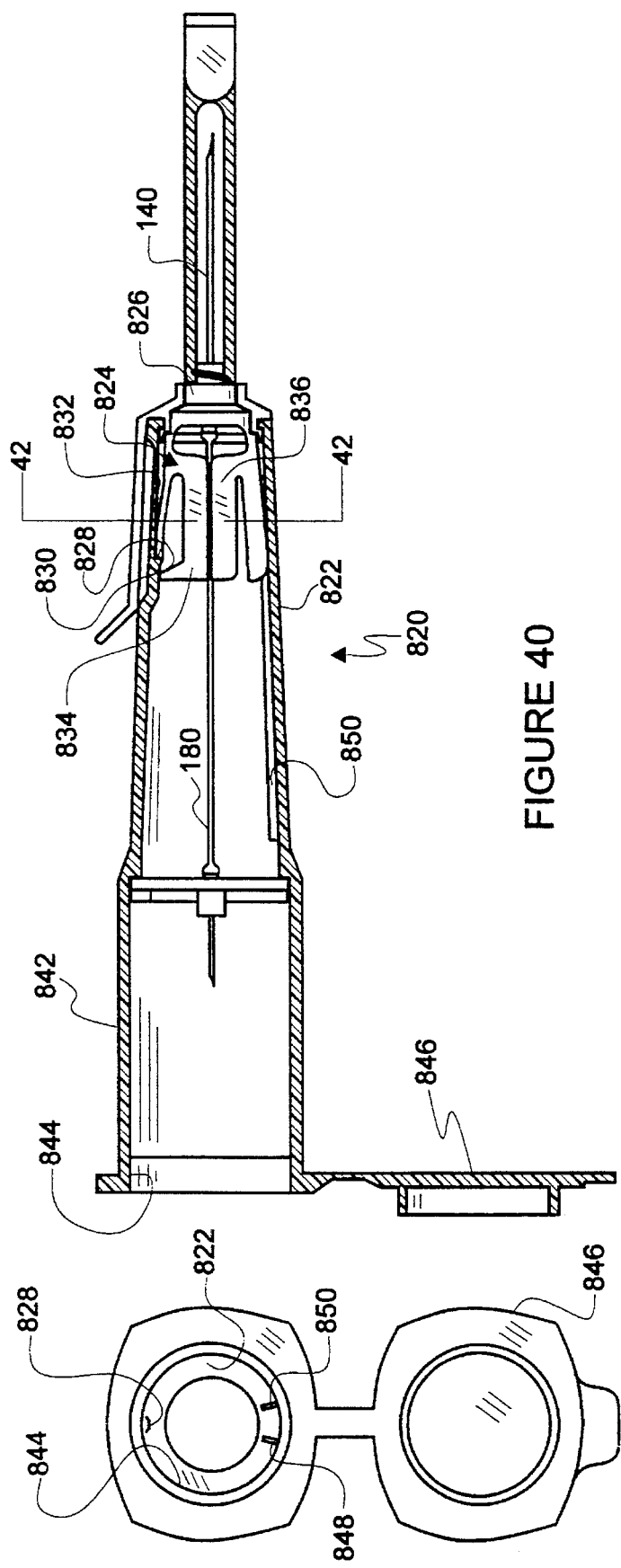
FIG. 39 is a rear elevation of the needle withdrawal device seen in FIG. 38.
FIG. 40 is a cross section of the needle withdrawal device seen in FIG. 38, but disposed in a cocked or ready state whereat a medical needle is ready for use.

As it is important that latch 830 aligns with catch 828 when needle 140 is extended, tapered cylindrical section 822 preferably comprises guides to assure correct travel of hub 824. Distally, device 820 is seen in FIGS. 38 and 40 to comprise a barrel section 842. At its back end, section 842 is seen to comprise an opening 844 and a tethered cover 846 which is used to provide protection for a rear needle 266, earlier described. Cover 846 is similar in form and function to cover 151, earlier described. As best seen in FIG. 39, segment 822 comprises a pair of guide rails 848 and 850. An inferior segment 852 of wing 836 is disposed to ride between rails 848 and 850 to maintain latch 830 in a desired position relative to catch 828 and distortable portion 832.

Figure 43:
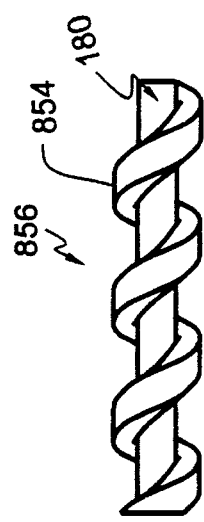
FIG. 43 is a perspective of an elastic tube with a helical member wrapped about the tube.
Figure 44:
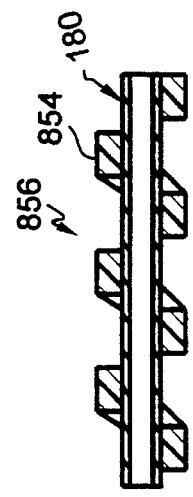
FIG. 44 is a cross section of the elastic tube and helical member seen in FIG. 43.
Figure 45:
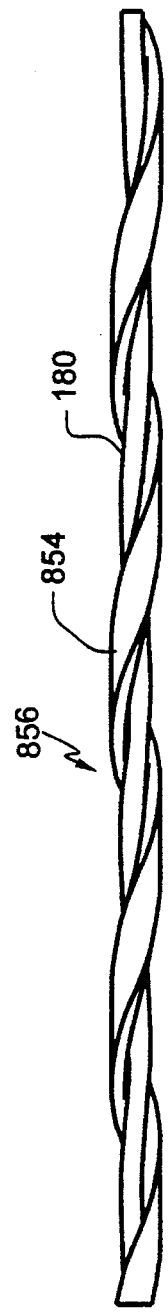
FIG. 45 is a perspective of the elastic tube of FIG. 43 stretched and the helical member also elongated to close tightly about the elastic tube to distort the tube from a round geometry.
Figure 46:
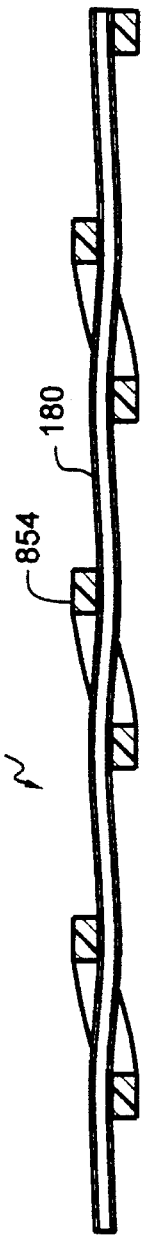
FIG. 46 is a cross section of the elastic tube and helical member seen in FIG. 45.

Another embodiment which constricts the volume of a constricted tube 180 to be less than the volume tube 180 in a relaxed state is seen in FIGS. 43–46. FIGS. 43 and 44 show tube 180 in a relaxed state. FIGS. 45 and 46 show the tube 180 in a stretched state. In simplest terms, tube 180 is seen to be disposed within a helical wrap 854 to form a combination 856. As is well known in the art, if wrap 854 is relatively inelastic, extending wrap 854 to nearly its resting length will cause wrap 854 to approximate a nearly straight line. As the cross sectional area of an elastic tube decreases by approximately the power of the number of rest lengths the tube is stretched, one who is skilled in the art of helix formation and elastic tube dynamics understands that there exists a critical pitch of the helix beyond which the internal volume of the helix decreases more rapidly upon extension than the internal volume of an interposed tube, such as tube 180.

Calculation of the critical pitch is relatively straight forward, as the following example shows. The general cartesian coordinate equations for a helix are:

$$x = a \cos \theta = a \cos ns \qquad \text{Eq. 2}$$

$$y = a \sin \theta = a \sin ns \qquad \text{Eq. 3}$$

$$z = l \qquad \text{Eq. 4}$$

where:
- a is the radius of the helix.
- θ is the angle of rotation of the helix about its long axis.
- s is the distance along the helix.
- l is the distance along the long (z) axis of the helix.
- n is the angular rate of change of θ as a function of l.

An equation for the length of a segment along the helix is given by:

$$ds = sqrt(dx^2 + dy^2 + dz^2) \qquad \text{Eq. 5}$$

Differentiating Eq.'s 2, 3 and 4, with respect to s and l, and substituting into Eq. 5:

$$ds = sqrt(a^2 n^2 \sin^2 ns \, ds^2 + a^2 n^2 \cos^2 ns \, ds^2 + dl^2) \qquad \text{Eq. 6}$$

Which reduces to:

$$ds = sqrt(a^2 n^2 ds^2 + dl^2) \qquad \text{Eq. 7}$$

or:

$$ds^2(1 - a^2 n^2) = dl^2$$

Integrating over the length (S) of the helix and of a distance (L) to which the helix is spread, the relationship between a and n is given by:

$$S = L/sqrt(1 - a^2 n^2) \qquad \text{Eq. 8}$$

The value of n may be given as:

$$n = 2\pi N/S \qquad \text{Eq. 9}$$

Where N is the total number of turns in helix length S.

Substituting for n and squaring both sides of the equation and solving for radius a:

$$S = L/sqrt(1 - a^2 [2\pi N/S]^2) \qquad \text{Eq. 10}$$

or:

$$S^2 = S^2 L^2 /(S^2 - a^2 [2\pi N]^2) \qquad \text{Eq. 11}$$

which yields:

$$L^2 = (S^2 - a^2 [2\pi N]^2) \qquad \text{Eq. 12}$$

Solving for a:

$$a = Sqrt(S^2 - L^2)/2\pi N \qquad \text{Eq. 13}$$

Solving for N:

$$N = Sqrt(S^2 - L^2)/2\pi a \qquad \text{Eq. 14}$$

Through experimentation, it has been found that change in internal volume of a stretched tube between two known points along a length of the tube (not comprising endpoints where the tube is connected to a hub or the like) is not changed substantially by stretching.

Therefore, the following relationships apply:

$$V = 2\pi a^2 l' \qquad \text{Eq. 15}$$

where:
- l' is also the length of the section between the two known points.

Note that, since V is a constant:
- a is substantially equivalent to sqrt(K/l') where K is an easily derived constant.

It has also been determined experimentally that the total internal volume (V') of an elastic tube does vary due at least to volumetric variations at tube ends where unions are made with connecting hubs. This variation generally causes the volume of a stretched tube to be greater than the volume of the same unstretched tube. This change in volume results in fluid regurgitation when the tube is used as a retracting mechanism and concurrently as a container and transport path for fluid received from a medical needle. It is for this reason that use of a helix wrap (such as wrap 854) is preferably used to reduce or restrict an increase in volume of the stretched tube.

An example of a method of design and employment of a volume restricting helix is given below:

Using a plastic tube in place of the medical needle to permit visual observation of the increase in volume due to stretching an elastic tube to a length three times its rest state length, the increase (δV') in volume was observed to be:

$$\delta V' = 6.5 \text{ microliters } (\mu l)$$

in an elastic tube having the following rest state dimensions:
- O.D.$_{at\ rest}$=3.18 mm
- I.D.$_{at\ rest}$=1.59 mm
- Length$_{at\ rest}$=19.1 mm
- Internal Volume$_{at\ rest}$=38 μl and having the following stretched dimensions:
- Nominal O.D.$_{stretched}$=1.83 mm
- Calculated I.D. stretched=0.92 mm
- Length$_{stretched}$=57.2 mm
- Internal Volume$_{stretched}$=45 μl
- Nominal tube O.D. volume$_{stretched}$=150 μl Assuming that a compressive reduction in total tube volume (including the tube itself) would result in a reduction in internal volume of substantially the same amount, a reduction of the O.D. volume to approximately 143 μl when the tube is stretched requires compressing the exterior of the tube to an equivalent average diameter of about 1.78 mm.

Because the number of turns of the helix is not permitted to change when the helix is lengthened from a rest state to a stretched state of tube 180 in this application, Eq. 14 (reproduced below) can be used to evaluate the length S and number of turns N of the helix.

$$N = Sqrt(S^2 - L^2)/2\pi a \qquad \text{Eq. 14}$$

By entering values for the rest or unstretched state (r), Eq. 14 becomes:

$$N = Sqrt(S^2 - L_r^2)/2\pi a_r \qquad \text{Eq. 14r}$$

Likewise, entering values for stretched state (s), Eq. 14 becomes:

$$N = Sqrt(S^2 - L_s^2)/2\pi a_s \qquad \text{Eq 14s}$$

and:

$$Sqrt(S^2 - L_r^2)/2\pi a_r = Sqrt(S^2 - L_s^2)/2\pi a_s$$

squaring and cross multiplying:

$$(S^2 - L_r^2)(2\pi a_s)^2 = (S^2 - L_s^2)(2\pi a_r)^2$$

solving for S:

$$S^2 = (L_r^2 a_s^2 - L_s^2 a_r^2)/(a_s^2 - a_r^2)$$

For the example given above:

$S = 68$ mm

Evaluating N (number of turns) from equation 14s:

$N = 6.6$ turns

However, as seen in FIGS. 45 and 46, wrap 854 does not fully enclose tube 180 and, therefore, tube 180 is periodically free to expand outward from constraint of wrap 854 in the gaps between constraint of the helix. For this reason, the number of actual turns ($N_a$) should be fewer than the predicted value of N, above. Even so, a more desirable value of $N_a$ can be arrived at without undue experimentation by one skilled in the art of fluid dynamics. It is well known in elastic tube extrusion art to enclose one or more helically wound coils of support material in the wall of extruded tubes. Such enclosed coils are most often used to add strength to the tube to support the tube against inadvertent collapse or to be able to withstand high pressure. A process similar to such an extrusion process can be used to make combination 856 by properly controlling pitch and using the coil not to support the tube against collapse, but to constrict the tube when it is stretched with a predetermined pitch of the helix.

Figure 47:
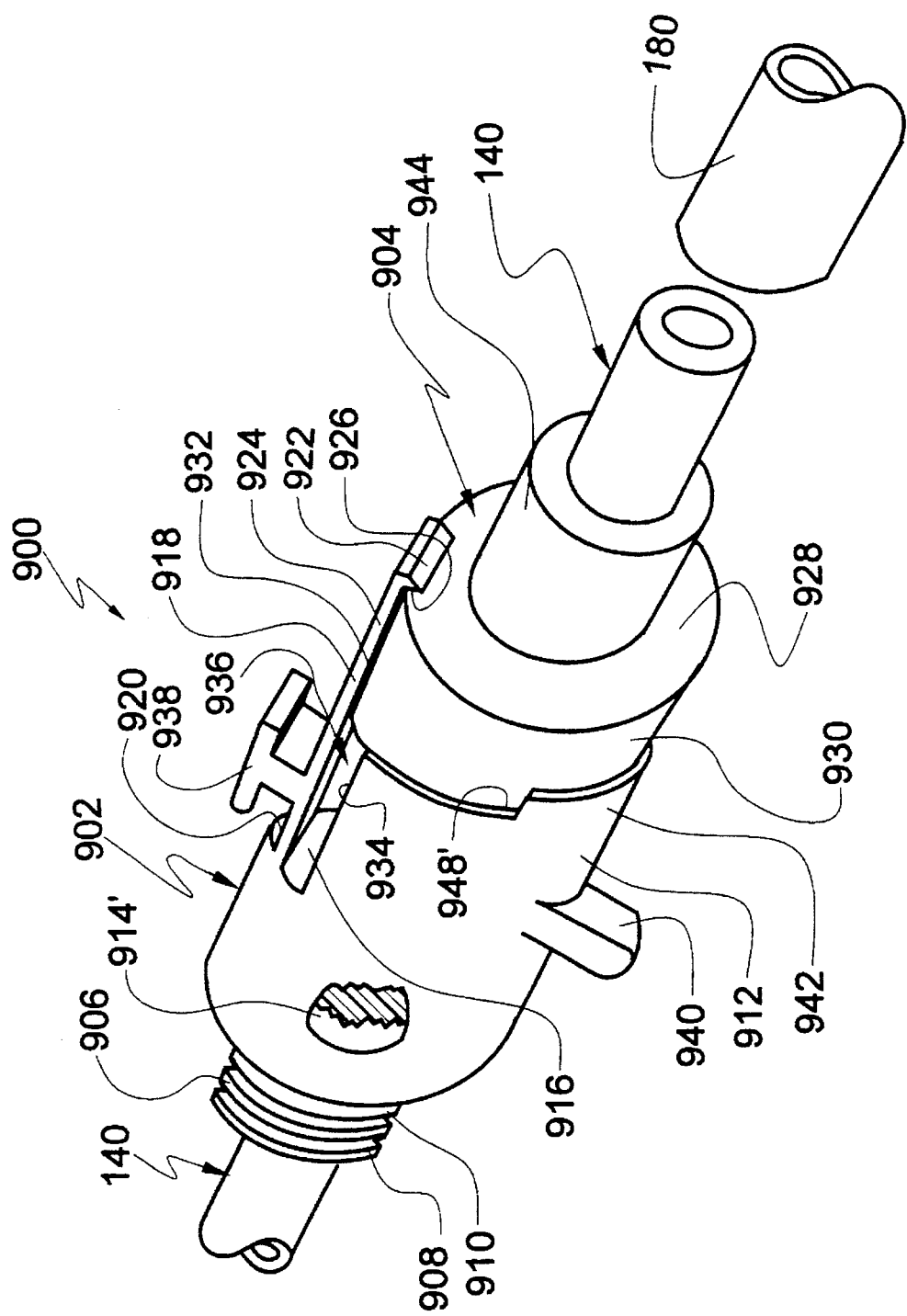
FIG. 47 is a perspective of a two part medical needle hub apparatus.

Reference is now made to FIGS. 47 and 48 wherein another hub part 900 is seen. Except for apparatus and method related to latching part 900 and releasing a portion of part 900 to retract a needle 140, part 900 is similar in form and function to needle/hub part 160.

Part 900 comprises two separable components, a forward component 902 and a rear component 904. Forward component 902 comprises a section 906 which comprises a threaded segment 908 and a cylindrical segment 910 which are similar in form and function to threaded portion 776 and cylindrical shoulder 774, respectively. Joined to segment 910 is an elongated cylindrical body 912 which comprises a pair of wing latches 914 and 914'. In FIG. 47, only a portion of one wing latch, latch 914', is seen mostly removed for a better presentation of the rest of forward component 902. A portion of cylindrical segment 910 is removed to provide an "L" shaped surface 916, the purpose of which is described in detail hereafter. Further component 902 comprises an elongated strut 918 securely affixed on one end 920 to surface 916, as best seen in FIG. 47.

Strut 918 comprises a latching member 922 disposed at the other end 924. Latching member 922 comprises a latch 926 which firmly, but releasably, affixes forward component 902 to rear component 904 along a surface 928 of component 904. Surface 928 is preferably orthogonal to the axis of needle 140.

Component 904 comprises a main body section 930 which comprises a flattened portion 932 which is juxtaposed an overlaying part of strut 918 as seen in FIG. 47. Note that portion 932 is raised above a portion 934 of "L" shaped surface 916 which is parallel to portion 932. In combination, strut 918, portion 934 and flattened portion 932 define a substantially rectangular opening 936 into which strut 918 may bend to release latching member 922 from surface 928.

Though not shown, it should be understood that part 900 is used within an elongated cylinder in a manner similar to that of needle/hub part 160. In that manner, forward component 902 comprises a raised button 938 which is raised from strut 918 to communicate with an internal surface of a distortable membrane, such as membrane 778 seen in FIG. 32. Note that distortion of the membrane and compressibly communicating with button 938 and therefore strut 918 above opening 936 can cause strut 918 to bend toward the surface of portion 934 such that latching member 922 is released from surface 928.

Forward component 902 further comprises a stabilizing leg 940 which is designed to communicate with an inner surface of the aforementioned elongated cylinder which is juxtaposed the distortable membrane to provide stability for needle 140. Also, component 902 comprises an arc shaped piece 942 which provides axially disposed support for rear component 904 while such is joined with forward component 902. As is the case of fore part 190 seen in FIG. 7, forward component 902 is slidably affixed to needle 140.

Rear component 904 further comprises a secure attachment to needle 140, a hub 944 to which an elastic tube 180 is attached. Proximal to the sharp end of needle 140 is a convex conical surface 946 which is shaped to mate with a concave conical surface 948 disposed inward from line 948' on cylindrical body 912 to provide a sterility barrier for needle 140 while component 902 is joined to component 904.

Needle 140 is extended for use by pulling a needle cover attached to threaded segment 908 as previously described. In a prior to use rest state, component 904 is affixed to component 902 by latching member 922 during manufacture of part 900. When part 900 is brought forward to extend needle 140 for use, wing latches 914 and 914' are caught upon catches (not shown) to securely and permanently affix component 902 in a forward position. At the end of a medical procedure, when it is desired to retract needle 140 for safe containment, button 938 is depressed through the distortable membrane to bend strut 918 into opening 936, cant latch member 922 away from surface 928 and thereby release component 904 and associated needle 140 for retraction by force of energy contained in elastic tube 180.

Similar to other hubs and needle related parts, both components 902 and 904 are preferably injection molded from synthetic resinous materials. Materials which are compatible with requirements for components 902 and 904 are well known in the needle hub manufacturing art.

The inventions disclosed herein may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. Apparatus for transporting and using and then safely retracting a medical needle directly from a patient into a container after use, said apparatus comprising:

the container comprising:
one end through which the medical needle passes when retracted;
another end which is moved apart from the medical needle to permit extension of said apparatus whereby the apparatus and the medical needle are configured for use in a medical procedure;

at least one container based catch for an associated latch whereby said apparatus is securely affixed in the extended configuration;

a portion of the container which is deformable such that a predetermined deformation of the container portion, in combination with a needle support catch, a releasable latch and trigger means, causes the needle to be released for safe retraction into the container;

a needle cover releasibly coupled to the container at the one end, the needle cover in combination with the container providing a protective barrier for contents of the cover and container prior to extending the apparatus;

a medical needle assembly disposed for transport and storage within said cover and container, said assembly comprising:

the medical needle comprising a sharpened point for entry into a patient and a pathway for flow of medical and physiological fluids;

connector hub means comprising:

a secure attachment to the medical needle;

the releasable latch which is integrally joined to the attachment and which is affixed to the needle support catch when the apparatus is extended to secure the medical needle for use in the medical procedure;

the trigger means for releasing the medical needle from being affixed by the needle support catch and releasable latch when acted upon via deformation of the container portion; and a connecting hub which is integral with said attachment and which affixes said assembly to a linear motion energy storage member;

the needle support catch which is disposed in a predetermined position to thereat be engaged with the releasable latch when the apparatus is extended;

the linear motion energy storage member comprising a first end which is proximal to the connecting hub and a second end which is distal from the connecting hub, said member being attached to the connecting hub at the first end for storing medical needle retraction energy as the other end of the container and needle are moved apart as the apparatus is extended.

2. Apparatus according to claim 1 wherein said linear motion energy storage member comprises elastic tube means which comprise an elongated elastic tube which is stretched as the apparatus is extended to provide both energy for retracting said needle and a fluid pathway from said needle.

3. Apparatus according to claim 2 wherein said elastic tube is made from silicone rubber.

4. Apparatus according to claim 2 wherein said elastic tube is made from medical grade latex.

5. Apparatus according to claim 2 wherein said connecting hub comprises a barbed fitting for the elastic tube.

6. Apparatus according to claim 2 wherein said connecting hub comprises a fitting for said elastic tube which is substantially the same outside diameter as the inside diameter of the elastic tube to limit increase in internal volume of the elastic tube as the tube is stretched.

7. Apparatus according to claim 2 wherein, in combination, said container and connector hub means comprise means for causing the internal volume of the stretched elastic tube to be smaller than the internal volume of the elastic tube during and after retraction of the needle to eliminate regurgitant flow from the needle as a result of retraction.

8. Apparatus according to claim 2 wherein the elastic tube means further comprise volume restricting means in restrictive communication with the elastic tube which, as the tube is stretched, compressibly reduce the internal volume of the elastic tube to a volume which is less than the elastic tube when unstretched to eliminate liquid regurgitation when the needle is retracted.

9. Apparatus according to claim 8 wherein the volume restricting means is made from the same material as the elastic tube.

10. Apparatus according to claim 2 further comprising a barrel part integrally affixed at the other end of the container and an elastic tube connection, said barrel part receiving biological fluid through the connection to the elastic tube and being instrumental in delivering biological fluid from a patient to an evacuated blood collection tube, an example of which is a Vacutainer® by Becton Dickenson.

11. Apparatus according to claim 2 further comprising a luer fitting integrally affixed at the other end of the container and a connection between the fitting and the elastic tube, said fitting receiving fluid through the connection to the elastic tube.

12. Apparatus according to claim 1 wherein said needle is a catheter insertion needle.

13. Apparatus according to claim 12 further comprising a catheter initially disposed about said catheter insertion needle and slidably removable therefrom as the catheter insertion needle is retracted.

14. Apparatus according to claim 12 wherein said linear motion energy storage member comprises elastic tube means which comprise an elastic tube which provides both energy for retracting said needle and a fluid pathway from said needle.

15. Apparatus according to claim 12 wherein said elastic tube is made from silicone rubber.

16. Apparatus according to claim 12 wherein said elastic tube is made from medical grade latex.

17. Apparatus according to claim 12 further comprising a filter which discriminately passes gasses but is impervious to liquids and a user viewable blood flash part which provides a visual indication of blood received through the needle.

18. Apparatus according to claim 1 wherein the container-based catch and needle support catch are the same part and the associated latch and releasable latch are the same part.

19. Apparatus according to claim 1 wherein said needle support catch comprises a slidable connection to said needle wherethrough the needle passes during retraction.

20. Apparatus according to claim 19 wherein said connection comprises a plug which substantially voids access to the container following retraction of the needle.

21. Apparatus according to claim 19 wherein said needle support catch and releasable latch are a single part joined by a frangible bridge which is broken through action of the trigger means.

22. Apparatus according to claim 1 wherein said catch comprises a slidable connection to said needle and a plug which closes all of the one end except for the slidable connection which comprises a small longitudinal hole substantially the diameter of the needle.

23. Apparatus according to claim 22 wherein said catch is made from hydrophobic material to substantially eliminate blood flow through the slidable connection hole.

24. Apparatus according to claim 1 wherein said needle support catch comprises a needle cover connector and said needle cover comprises a complementary catch connector whereby the needle cover is releasibly connected to cover and protect the needle assembly.

25. Apparatus according to claim 1 wherein said needle cover and said container, in combination, comprise a frangible part which connects the needle cover to the container for transport and storage prior to use and which is frangibly broken to permit apparatus extension, said needle cover and said container providing a sterile protective barrier for the medical needle assembly while joined and said frangible part providing a indicator for detection of tampering.

26. Apparatus according to claim 1 wherein said container comprises an exterior shield which, until removed, protects the deformable portion from inadvertent triggering during the medical procedure and which is facilely removed for access to the deformable portion and therethrough to the trigger means.

27. A method for using an apparatus which safely retracts a medical needle directly from a patient into a container after completing a medical procedure comprising the steps of:

providing an extendable apparatus comprising a container into which the medical needle is retracted, the medical needle initially disposed for protection within apparatus and attached to a linear motion energy storage member which receives needle retraction energy when the apparatus is extended and a removable needle cover and which is activated by a trigger, the container comprising a deformable portion which communicates with a trigger which accessible through the deformable portion;

extending the apparatus, thereby positioning the needle for use in the medical procedure, cocking the trigger and storing energy in the linear energy storage member;

exposing the needle by removing the needle cover;

introducing the medical needle into the patient;

performing the medical procedure;

accessing the deformable portion by placing a portion of a users hand thereover;

depressing the deformable portion thereby triggering release of the linear energy storage member and thereby safely retracting the medical needle into the container.

28. A method according to claim 27 wherein the accessing step comprises removing a shield which covers and protects the deformable portion from inadvertent triggering.

29. A method according to claim 27 wherein the retracting step comprises retracting the needle through a hole in the container approximately the same size as the outside diameter of the needle, thereby substantially retracting the needle into a closed container relative to opportunity for the needle or liquid to escape the container after retraction.

30. A method according to claim 27 wherein the safely retracting step comprises elastically compacting a elastic tube previously stretched in the extending step, the stretched tube providing both storage of retractive energy and a pathway for biological fluid flow.

31. A method according to claim 30 wherein the extending and retracting steps, in combination, limit the internal volume of the elastic tube when stretched to be less than the elastic tube when compacted.

32. A method according to claim 27 wherein the performing step comprises utilizing means for drawing blood using an evacuated blood collection tube.

33. A method according to claim 27 wherein the performing step comprises utilizing means for introducing an IV (intravenous) catheter into the patient.

34. A method according to claim 27 wherein the introducing and performing steps, in combination, comprise employing a luer fitting to attach the apparatus to a syringe.

35. A method according to claim 27 wherein the accessing step comprises using pressure from a single finger to cause the needle to be retracted from the patient.

36. Apparatus for transporting and using and then safely retracting a medical needle directly from a patient into a container after use, said apparatus comprising:

the container comprising:

one end through which the medical needle passes when retracted;

another end which is moved apart from the medical needle to permit extension of said apparatus whereby the apparatus and the medical needle are configured for use in a medical procedure;

at least one container based catch for an associated latch whereby said apparatus is securely affixed in the extended configuration;

a portion of the container comprising force communicating means through which a trigger is activated in combination with a releasable latch, to cause the needle to be released for safe retraction into the container;

a needle cover releasibly coupled to the container at the one end, the needle cover in combination with the container providing a protective barrier for contents of the cover and container prior to extending the apparatus;

a medical needle assembly disposed for transport and storage within said cover and container, said assembly comprising:

the medical needle comprising a sharpened point for entry into a patient and a pathway for flow of medical and physiological fluids;

connector hub means comprising:

a secure attachment to the medical needle;

the releasable latch which is integrally joined to the attachment and which is affixed to the needle support catch when the apparatus is extended to secure the medical needle for use in the medical procedure;

the trigger means for releasing the medical needle from being affixed by the needle support catch and releasable latch when acted upon via force through the communicating means of the container portion; and a connecting hub which is integral with said attachment and which affixes said assembly to a linear motion energy storage member;

the needle support catch which is disposed in a predetermined position to thereat be engaged with the releasable latch when the apparatus is extended;

the linear motion energy storage member comprising an elastic tube having a first end which is proximal to the connecting hub and a second end which is distal from the connecting hub, said member being attached to the connecting hub at the first end for storing medical needle retraction energy in the elastic tube as the other end of the container and needle are moved apart as the apparatus is extended, said tube also providing a lumen which acts as a pathway for medical and physiological fluids which pass through said needle.

37. Apparatus according to claim 36 wherein said energy communicating means comprise a deformable portion of said container.

38. Apparatus according to claim 36 wherein said elastic tube is made from silicone rubber.

39. Apparatus according to claim 36 wherein said elastic tube is made from medical grade latex.

40. Apparatus according to claim 36 wherein said connecting hub comprises a barbed fitting for the elastic tube.

41. Apparatus according to claim 36 wherein said connecting hub comprises a fitting for said elastic tube which is substantially the same outside diameter as the inside diameter of the elastic tube to limit increase in internal volume of the elastic tube as the tube is stretched.

42. Apparatus according to claim 36 wherein, in combination, said container and connector hub means comprise means for causing the internal volume of the stretched elastic tube to be smaller than the internal volume of the elastic tube during and after retraction of the needle to eliminate regurgitant flow from the needle as a result of retraction.

43. Apparatus according to claim 36 wherein the elastic tube means further comprise volume restricting means in restrictive communication with the elastic tube which, as the tube is stretched, compressibly reduce the internal volume of the elastic tube to a volume which is less than the elastic tube when unstretched to eliminate liquid regurgitation when the needle is retracted.

44. Apparatus according to claim 43 wherein the volume restricting means is made from the same material as the elastic tube.

45. Apparatus according to claim 36 further comprising a barrel part integrally affixed at the other end of the container and an elastic tube connection, said barrel part receiving biological fluid through the connection to the elastic tube and being instrumental in delivering biological fluid from a patient to an evacuated blood collection tube, an example of which is a Vacutainer® by Becton Dickenson.

46. Apparatus according to claim 36 further comprising a luer fitting integrally affixed at the other end of the container and a connection between the fitting and the elastic tube, said fitting receiving fluid through the connection to the elastic tube.

47. Apparatus according to claim 36 wherein said needle is a catheter insertion needle.

48. Apparatus according to claim 47 further comprising a catheter initially disposed about said catheter insertion needle and slidably removable therefrom as the catheter insertion needle is retracted.

49. Apparatus according to claim 47 further comprising a filter which discriminately passes gasses but is impervious to liquids and a user viewable blood flash part which provides a visual indication of blood received through the needle.

50. Apparatus according to claim 36 wherein the container-based catch and needle support catch are the same part and the associated latch and releasable latch are the same part.

51. Apparatus according to claim 36 wherein said needle support catch comprises a slidable connection to said needle wherethrough the needle passes during retraction.

52. Apparatus according to claim 51 wherein said connection comprises a plug which substantially voids access to the container following retraction of the needle.

53. Apparatus according to claim 51 wherein said needle support catch and releasable latch are a single part joined by a frangible bridge which is broken through action of the trigger means.

54. Apparatus according to claim 36 wherein said needle support catch comprises a slidable connection to said needle and a plug which closes all of the one end except for the slidable connection which comprises a small longitudinal hole substantially the diameter of the needle.

55. Apparatus according to claim 54 wherein said needle support catch is made from hydrophobic material to substantially eliminate blood flow through the slidable connection hole.

56. Apparatus according to claim 36 wherein said needle support catch comprises a needle cover connector and said needle cover comprises a complementary catch connector whereby the needle cover is releasibly connected to cover and protect the needle assembly.

57. Apparatus according to claim 36 wherein said needle cover and said container, in combination, comprise a frangible part which connects the needle cover to the container for transport and storage prior to use and which is frangibly broken to permit apparatus extension, said needle cover and said container providing a sterile protective barrier for the medical needle assembly while joined and said frangible part providing a indicator for detection of tampering.

58. Apparatus according to claim 36 wherein said container comprises an exterior shield which, until removed, protects the force communicating means and therefore the trigger from inadvertent triggering during the medical procedure and which is facilely removed for access to the deformable portion and therethrough to the trigger means.

59. Apparatus for transporting and using and then safely retracting a medical needle directly from a patient into a container after use, said apparatus comprising:

the container into which the needle is retracted;

the medical needle through which medical and physiological fluids flow;

an elastic tube is which is directly joined to said medical needle, stretched to store energy required for retraction of the medical needle and which comprises a lumen which serves as a pathway for the medical and physiological fluids;

at least one member which compresses the elastic tube when stretched to assure a smaller internal volume of the elastic tube lumen when the elastic tube is stretched and a larger internal volume of the elastic tube lumen when the elastic tube is unstretched.

60. Apparatus as in claim 59 wherein said at least one member is made from the same material as the elastic tube.

61. Apparatus as in claim 59 wherein said at least one member is integrally joined to said elastic tube.

62. A method for retracting a medical needle into a container for safe containment without regurgitating fluid outwardly from said needle comprising the steps of:

providing the container into which the needle is retracted;

providing the medical needle which is disposed outside the container for use in a medical procedure and which is retracted into said container at the end of the procedure;

providing an elastic tube which is securely affixed to the needle, stretched to provide retraction energy for the needle and which inherently comprises a lumen which provides a pathway for fluids passing through said needle, said lumen comprising a rest volume when the elastic tube is in an unstretched state;

compressing the exterior of the elastic tube when stretched to reduce the volume of the lumen without closure of the lumen to a volume which is less than the rest volume; and retracting the needle as the elastic tube is elastically relaxed substantially to the unstretched state without compressing the exterior of the elastic tube thereby permitting the lumen of the elastic tube when relaxed to be greater than the lumen of the elastic tube when stretched, said larger volume of the relaxed tube being the result of forces inherent in the tube which assure retention of fluid within the lumen as the tube is shortened.

\* \* \* \* \*